(12) United States Patent
Guerinot et al.

(10) Patent No.: US 6,590,140 B1
(45) Date of Patent: Jul. 8, 2003

(54) METAL-REGULATED TRANSPORTERS AND USES THEREFOR

(75) Inventors: Mary Lou Guerinot, Etna, NH (US); David J. Eide, Columbia, MO (US)

(73) Assignees: Trustees of Dartmouth College, Hanover, NH (US); Regents of the University of Minnesota, Minneapolis, MN (US)

(*) Notice: Subject to any disclaimer, the term of this patent is extended or adjusted under 35 U.S.C. 154(b) by 0 days.

(21) Appl. No.: 09/579,174

(22) Filed: May 25, 2000

Related U.S. Application Data

(62) Division of application No. 09/107,858, filed on Jun. 30, 1998, now Pat. No. 6,162,900, which is a division of application No. 08/758,621, filed on Nov. 27, 1996, now Pat. No. 5,846,821.
(60) Provisional application No. 60/018,578, filed on May 29, 1996.

(30) Foreign Application Priority Data

Oct. 11, 1996 (CA) .............................................. 2187728

(51) Int. Cl.$^7$ ........................ A01H 1/00; A61K 38/43; C07H 21/04; C07K 14/415; C12N 5/14
(52) U.S. Cl. .................. 800/278; 424/58; 424/195.1; 435/183; 435/410; 435/419; 435/320.1; 530/350; 530/370; 536/23.1; 536/23.2; 536/23.6; 800/295
(58) Field of Search ............................... 424/58, 195.1; 435/183, 410, 419, 320.1; 530/350, 370; 536/23.1, 23.2, 23.6; 800/278, 295

(56) References Cited

U.S. PATENT DOCUMENTS 5,364,451 A    11/1994  Raskin et al.

OTHER PUBLICATIONS

Dancis, A. et al., "Molecular Characterization of a Copper Transport Protein in S. cerevisiae: An Unexpected Role for Copper in Iron Transport," *Cell*, vol. 76, 393–402 (1994).
Dix, D. et al., "The FET4 Gene Encodes the Low Affinity Fe(II) Transport Protein of *Saccharomyces cerevisiae*," *The Journal of Biological Chemistry*, vol. 269, No. 42, 26092–26099 (1994).
Eide, D. et al., "A Novel Iron–Regulated Metal Transporter from Plants Identified by Functional Expression in Yeast," *Proc. Natl. Acad. Sci. USA*, vol. 93, 5624–5628 (1996).
Evans, K. et al., "Expression of the Pea Metallothionein–like Gene PsMT$_A$ in *Escherichia coli* and *Arabidopsis thaliana* and Analysis of Trace Metal Ion Accumulation: Implications for PsMT$_A$ Function," *Plant Molecular Biology*, vol. 20, 1019–1028 (1992).
Fawaz, F., "Zinc Deficiency in Surgical Patients: A Clinical Study," *Journal of Parenteral and Enteral Nutrition*, vol. 9, No. 3, 364–369 (1985).
Karin, M. and Richards, R.; "Human Metallothionein Genes—Primary Structure of the Metallothionein–II Gene and a Related Processed Gene," *Nature*, vol. 299, 797–802 (1982).

Levander, O., "Nutritional Factors in Relation to Heavy Metal Toxicants," *Federation Proceedings*, vol. 36, No. 5, 1683–1687 (1977).
New England Biolabs Catalog [New England Biolabs, Beverly, Massachusetts, USA (1987/87)] 60–2.
Odne, M. et al., "Rationale for Adding Trace Elements to Total Parenteral Nutrient Solutions—A Brief Review," *Am J Hosp Pharm*, vol. 35, 1057–1059 (1978).
Repke, J., "Calcium, Magnesium, and Zinc Supplementation and Perinatal Outcome," *Clinical Obstetrics and Gynecology*, vol. 34, No.2, 262–267 (1991).
Rugh, C. et al., "Mercuric Ion Reduction and Resistance in Transgenic Arabidopsis Thaliana Plants Expressing a Modified Bacterial merA Gene," *Proc. Natl. Acad. Sci. USA*, vol. 93, 3182–3187 (1996).
Shakman, R., "Nutritional Influences on the Toxicity of Environmental Pollutants," *Arch Environ Health*, vol. 28, 105–113 (1974).
Strobel, C. et al., "A Zinc–Deficiency Dermatitis in Patients on Total Parenteral Nutrition," *International Journal of Dermatology*, vol. 1, 575–581 (1978).
Valdes–Ramos, R., "Zinc: A Perinatal Point of View," *Progress in Food and Nutrition Science*, vol. 16, 279–306 (1992).
Walsh, C. et al., "Zinc: Health Effects and Research Priorities for the 1990s," *Environ Health Perspect*, vol. 102, suppl. 2, 5–46 (1994).
Yip, R., "Iron Deficiency: Contemporary Scientific Issues and International Programmatic Approaches," *J Nutr.*, vol. 124, 1479S–1490S (1994).
Zhao, H. and Eide, D., "The Yeast ZRT1 Gene Encodes the Zinc Transporter Protein of a High–Affinity Uptake System Induced by Zinc Limitation," *Proc. Natl. Acad. Sci. USA*, vol. 93, 2454–2458 (1996).
Zhao, H. and Eide, D., "The ZRT2 Gene Encodes the Low Affinity Zinc Transporter in *Saccharomyces cerevisiae*," *The Journal of Biological Chemistry*, vol. 271, No. 38, 23203–23210 (1996).

Primary Examiner—Phuong T. Bui
(74) *Attorney, Agent, or Firm*—Lahive & Cockfield, LLP

(57) ABSTRACT

Isolated nucleic acid molecules encoding members of the MRT family of polypeptides which include, in a preferred embodiment, at least one transmembrane domain having at least about 30%, more preferably at least about 50%, 55%, 60%, 70%, 80% or 90% amino acid sequence identity with SEQ ID NO:2, SEQ ID NO:4, SEQ ID NO:6, SEQ ID NO:8 or SEQ ID NO:14 and/or at least one histidine rich domain, are described. The MRT polypeptides of the invention are capable of transporting metals such as Fe(II), Cd, Co, Mn, Pb, Hg and Zn. Transgenic plants in which expression of an MRT polypeptide of the invention is altered are also described. These transgenic plants can be used to remove pollutants from soil or as nutritional supplements to treat iron- or zinc-deficiency. Antisense nucleic acid molecules, recombinant expression vectors containing nucleic acid molecules of the invention, and host cells into which the expression vectors have been introduced are also described. The invention further provides isolated MRT polypeptides, fusion polypeptides and active fragments thereof. Therapeutic methods utilizing compositions of the invention are also provided.

8 Claims, 25 Drawing Sheets

A

```
1    MKTIFLVLIFVSFAISPATSTAPEECGSESANPCVNKAKALPLK VIAIFV
         Signal Sequence
51   ILIASMIGVGAPLFS RNVSFLQPDGN IFTIIKCFASGIILGTGFM HVLPD
             I                      II
101  SFEMLSSICLEENPWHK FPFSGFLAMLSGLITLAI DSMATSLYTSKNAVG
                           III
151  IMP HGHGHGHG PANDVTLPIKEDDSSNAQLLRYR VIAMVLELGIIVHS
                                              IV
199  VVIGLSLGAT SDTCTIK GLIAALCFHQMFEGMGLGGCILQA EYTNMKK FV
                              V
249  MAFFFAVTTPFGIALGIALSTVY QDNSPK ALITVGLLNACSAGLLIYMAL
            VI                        VII
299  VDLLAAEFMGPKLQGSIK MQFKCLIAALLGCGGMSIIA KWA
                          VIII
```

B

```
IRT1   8 LIFVSFAISPATSTAPEECGSESANPCVNKAKALPLKVIAIFVILIASMIGVGAPLFSRN 67
         ||  :|::||| ||||| | |   |||:|||||||||::||  || :|:|||::|||||
IRT2     LILFTFTVSPAISTAPEHCDSGFDNPCINKAKALPLKIVAIVAILTTSLIGVTSPLFSRY

IRT1  68 VSFLQPDGNIFTIIKCFASGIILGTGFMHVLPDSFEMLSSICLEENPWHKFPFSGFLAML 127
         :||| |||| | |:|||:||||||||||||||||||||||||| ||| :|||||||:||:||:
IRT2     ISFLRPDGNGFMIVKCFSSGIILGTGFMHVLPDSFEMLSSKCLSDNPWHKFPFAGFVAMM

IRT1 292 LLIYMALVDLLAAEFMGPKLQGSIKMQFKCLIAALLGCGGMSIIAKWA 339
         :|:|||||||:||:|:::|:   ::|   :   || | || :| ||
IRT3     ILVYMALVDLIAADFLSTKMRCNFRLQIVSYVMLFLGAGLMSSLAIWA

IRT1 191 ELGIIVHSVVIGLSLGATSDTCTIKGLIAALCFHQMFEGMGLGGCILQAEYTNMKKFVMA 250
         :||:|||||||||::||:  :|||::|:|||||| |||||||||||||||||| |:  : :
Rice     KMGIVVHSVVIGLGMASQNVCTIRPLVAALCFH?MFEGMGLGGCILQAGYGGRTRSALV IRT1 251 FFFAVTTPFGIALGIALSTVYQDNS 275
         |||: ||||||||||:||: || | :
Rice     FFFSTTTPFGIALGLALTRVYSDTA
```

*Fig. 1*

Nucleotide sequence of IRT1:

```
   1 caaattcagc acttctcatg aaaacaatct tcctcgtact catttttgtc tcttttgcaa
  61 tctctccagc aacttcaact gcgccggaag aatgtggaag cgagtcagcg aacccgtgcg
 121 tcaacaaagc taaagctttg cctctcaaag tcatagcaat cttcgtaatc ctcattgcaa
 181 gcatgattgg tgttggagct cctctcttta gccgtaacgt ttcgttcctc caaccagacg
 241 gaaacatctt cactatcatt aagtgtttcg cctccgggat catccttgga accggttta
 301 tgcacgtttt acctgattct ttcgaaatgt tgtcatctat atgtcttgaa gagaacccgt
 361 ggcataaaatt tccttctcc ggatttctcg ctatgttatc gggtctaatc actctagcca
 421 ttgactccat ggccacgagc ctatacacca gcaagaacgc agttggtatc atgccccatg
 481 gtcatggtca tggtcacggc cccgcaaatg atgttacctt accaataaaa gaagatgatt
 541 cgtcaaatgc acagctcttg cgataccgag tcattgccat ggtcttggaa cttgggatca
 601 tagttcactc ggtggtcatt ggattatctc taggagcaac tagtgacact tgcaccatta
 661 aaggacttat agcagctctt tgcttccatc aaatgttcga aggcatgggt cttggcggtt
 721 gtatcctcca ggctgagtat acaaatatga agaaatttgt tatggcgttc ttttcgcgg
 781 taacaacacc attcggaata gcgttaggga tcgctctatc aactgtttac caagataata
 841 gcccaaaagc tttgatcacg gttggacttc taaatgcatg ctccgctgga ttgctcattt
 901 acatggcact cgtggatctt ctagctgcgg agttcatggg acctaagctt caaggtagca
 961 tcaaaatgca gttcaagtgt ttaatcgcgg ctcttctcgg gtgcggtgga atgtcgatta
1021 tcgccaaatg gcttaacta atactccaga tattgcggaa ttgaaatcat gtggatttca
1081 ttatcgaact aaaaccgttt taggtttacg tctcgattct ctatcggttt tttatcttct
1141 cttacaaaag atttgcgtgg atctatcaca ttttaaggaa catgtctttt ggtagatatg
1201 taaatgtgat aggcccacg attcatagtt ttcttttgta tcttcctta ttttgtcaag
1261 gcagtatagt tcatatcgtg taatgttttt gcatctcata taaataaata aaacttttgc
1321 tgcttttc
```

Fig. 4

Protein sequence:

MKTIF LVLIFVSFAI SPATSTAPEE CGSESANPCV NKAKALPLKV

IAIFVILIAS MIGVGAPLFS RNVSFLQPDG NIFTIIKCFA SGIILGTGFM

HVLPDSFEML SSICLEENPW HKFPFSGFLA MLSGLITLAI DSMATSLYTS

KNAVGIMPHG HGHGHGPAND VTLPIKEDDS SNAQLLRYRV IAMVLELGII

VHSVVIGLSL GATSDTCTIK GLIAALCFHQ MFEGMGLGGC ILQAEYTNMK

KFVMAFFFAV TTPFGIALGI ALSTVYQDNS PKALITVGLL NACSAGLLIY

MALVDLLAAE FMGPKLQGSI KMQFKCLIAA LLGCGGMSII AKWA

```
ZRT2  266  VFILEFGILIFHSVFVGLSLSVAGE..EFETLFIVLTFHQMFEGLGTRVAETNWPESKK
ZRT1  222  FLIEFGVIIFHSVMIGLNLGSVGD..EFSSLYPVLVFHQSFEGGTGARLSAIEFPRSKR
IRT1  187  AMVLELGIVHSVVIGLSLGATSDTCTIKGLIAALCFHQMFEGMGIGGCILQAEYTNMKK
                        IV                        V

ZRT2  324  YMPWLMGLAFTLTSPIAVAVGIGVRHSWIPGSRRALANGVFDSISSGLLYTGLVSLMA
ZRT1  280  WWPWALCVAYGLITPICVAIGLGVRTRYVSGSYTALVISGVLDAISAGLLYTGLVLLA
IRT1  247  F...VMAFFEAVITPFGIALGTALSTVYQDNSPKALITVGLLNACSAGLLYMALVDLLA
                        VI                        VII

ZRT2  384  HEFLYSNQFKGPDGLKKMLSAYLIMCCGAALMALLGKWA
ZRT1  340  RDFIFNPQ..RTKDLRELSFNVICTLFGAGIMALIGKWA
IRT1  304  AEFM...GPKLQGSIKMQFKCLIAALLGCGGMSIIAKWA
                        VIII
```

*Fig. 13* (continued)

FIG.15A
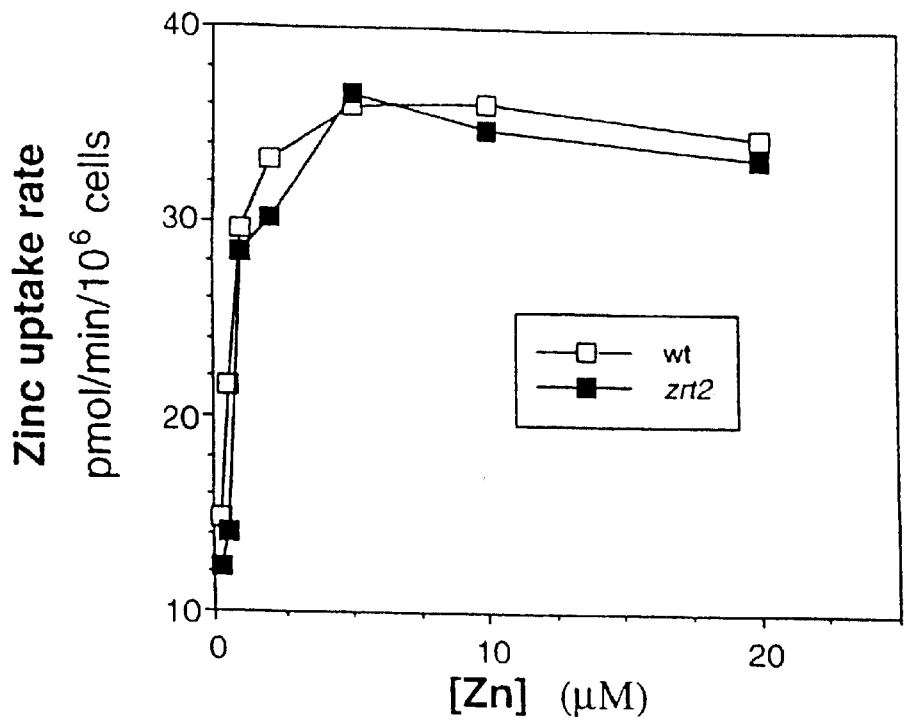
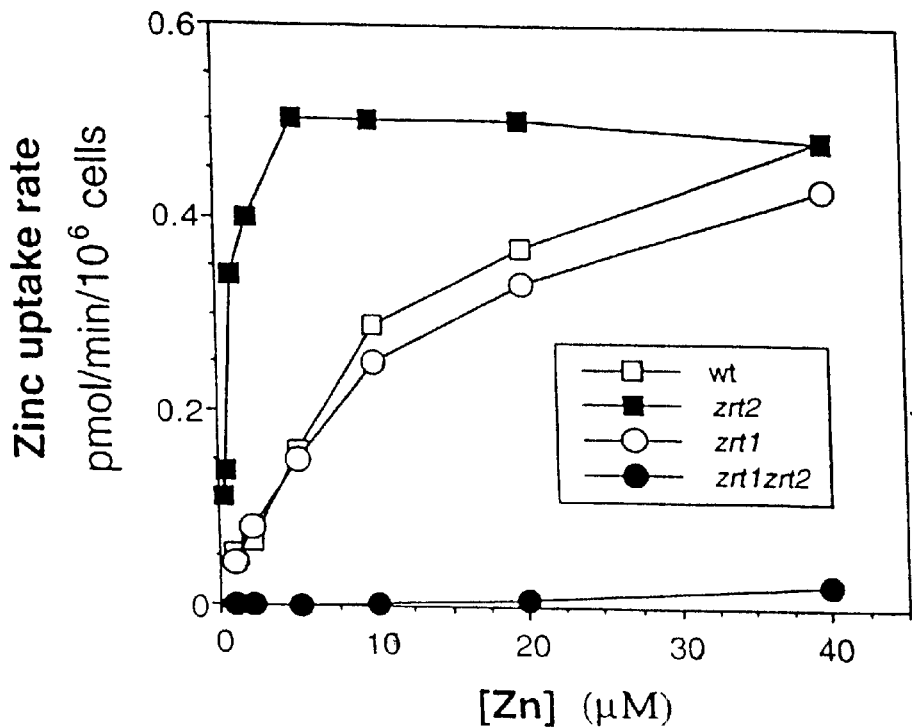
FIG.15B

FIG.16A
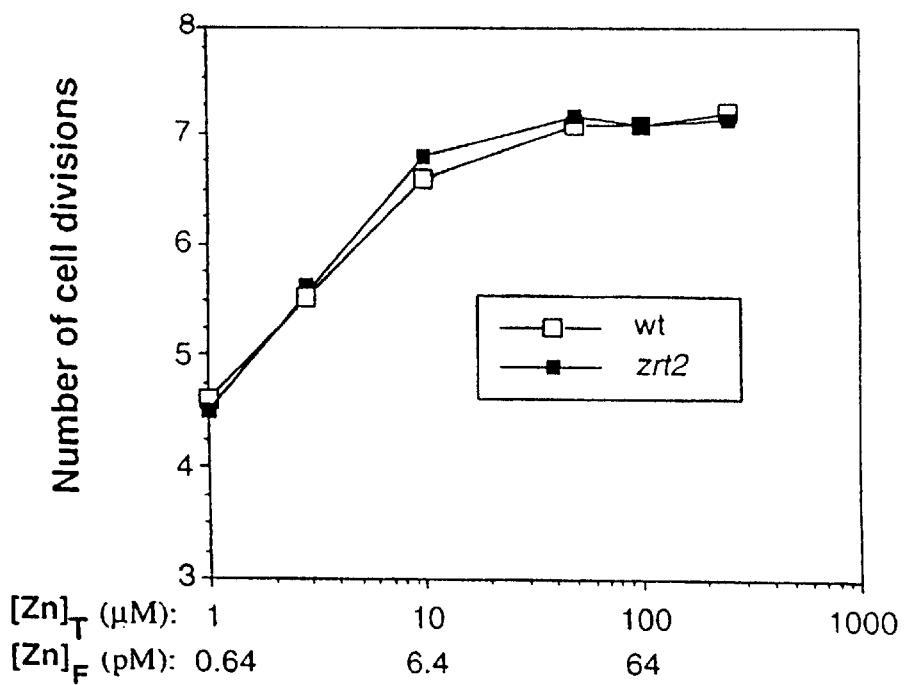
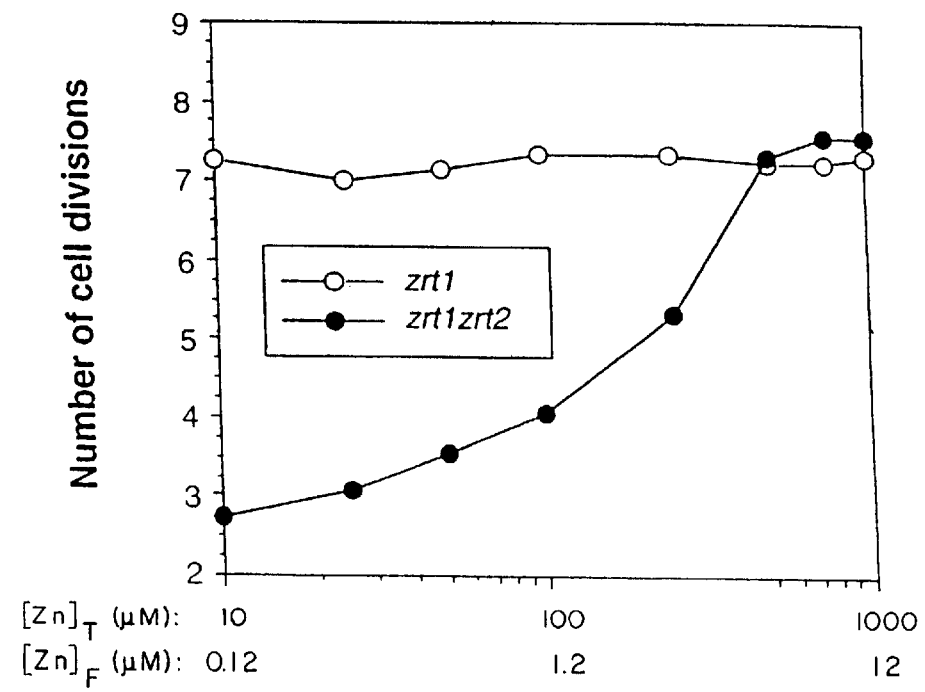
FIG.16B

ZIP1 protein sequence

MSECGCFSATTMLRICVVLIICLHMCCASSDCTSHDDPVSQDEAEKATKLKLGSIALLLV
AGGVGVSLPLIGKRIPALQPENDIFFMVKAFAAGVILCTGFVHILPDAFERLSSPCLEDT
TAGKFPFAGFVAMLSAMGTLMIDTFATGYYKRQHFSNNHGSKQVNVVDEEEHAGHVHIH
THASHGHTHGSTELIRRRIVSQVLEIGIVVHSVIIGISLGASQSIDTIKPLMAALSFHQF
FEGLGLGGCISLADMKSKSTVLMATFFSVTAPLGIGIGLGMSSGLGYRKESKEAIMVEGM
LNAASAGILIYMSLVDLLATDFMNPRLQSNLWLHLAAYLSLVLGAGSMSLLAIWA

ZIP1 nucleotide sequence

CAGTGTGAGTAATTTAGCAAGAACATAAATATCTTAAACTCATGTCTGAATGTGGATGTT
TTCGGCAACAACTATGTTGAGAATTTGTGTAGTATTGATAATATGTTGCATATGTGTT
GTGCCTCGAGTGATTGTACAAGTCACGATGCTTACTTCTTGTAGCCGGAGGAGTCGGCGTGA
CGACGAAGCTAAAGCTTGGTTCGATAGCTTCGATAGCTTCAACCGGAAATGATATCTTCTTCA
GTCTACCGTTGAATCGGGAAAGGATTCCGGCGTTACAACCGGAAATGATATCTTCTTCA
TGGTGAAAGCTTTGCTGCAGGAGTGAGCTCTCCATGTCTGTCTTGAGGACACTACAGCTGGGAAGTTCCCGT
ACGCGTTCGAGAGATTGAGCTCTGATGCGATGCGGCAACATTTAGCAACAATAACCATGGGAGCAAGCAAGTGAACGTAG
CAGGGTATTACAAGAGAAGAGCATGCGGGTCATGTCAGAGAGACGTATAGTGTCGCAGGTGCTTGAGATTG
TAGTAGATGAAGAAGAGACCGAGTTGATCAGAAGACGTATAGTGTCGCAGGTGCTTGAGATTG
ACACACATGGTTGTGCATTCGGTTATTATAGGGATATCACTTGGAGCTTCACAGAGCATAGACA
CCATAAAGCCACTCATGGCTGCGGGATCATCCCTGAAATCGAAGTGCTAATGGCGACATTT
GTGGATGCATCCCTGACGGCGCCACTTGGGATAGGAGGAATAATGGTGAAGGAATGTTGAATGCTGCTCTGCTG
TCTCGGTGACGGCGCCACTTGGGATAGGAGGAATAATGGTGAAGGAATGTTGAATGCTGCTCTGCTG
ACAGGAAAGAAGAGCAAAGCAAGCTCACTTGGCTTCACTCTTGCTACTGCTGCTACTTCTCTCGTCCTAGGCGCAGGTT
GGATACTCATATACAATCTCTGGCTTCACTTGGCTACTGCTGCTACTTCTCTCGTCCTAGGCGCAGGTT
TGCAATCCAATCTCTGCGTCTGGCCTGGCCTGATTCTTGATCTGAAACTAACAACAACAAAC
CCATGTCTCTCCTGCCATCTCGGCCCTGATTCTTGATCTGAAACTAACAACAACAAAC
CAAATGCCGCTCTTTTCTCAAATCTGTAATGGTGTTCTAATCTCAGAATCAATACTA
TTCTATCTTGAACAC

*Fig. 18*

ZIP2 protein sequence

```
  1 MALSSKTLKS TLVFLSIIFL CFSLILAHGG IDDGDEEEET NQPPPATGTT
 51 TVVNLRSKGL VLVKIYCIII LFFSTFLAGI SPYFYRWNES FLLLGTQFSG
101 GIFLATALIH FLSDANETFR GLKHKEYPYA FMLAAAGYCL TMLADVAVAF
151 VAAGSNNNHV GASVGESRED DDVAVKEEGR REIKSGVDVS QALIRTSGFG
201 DTALLIFALC FHSIFEGIAI GLSDTKSDAW RNLWTISLHK VFAAVAMGIA
251 LLKLIPKRPF FLTVVYSFAF GISSPIGVGI GIGINATSQG AGGDWTYAIS
301 MGLACGVFVY VAVNHLISKG YKPLEECYFD KPIYKFIAVF LGVALLSVVM
```

ZIP2 nucleotide sequence

```
   1 ATGGCTTTGT CTTCCAAAAC CCTAAAGTCA ACTCTCGTCT TCCTCTCTAT
  51 TATTTTCCTC TGTTTCTCCT TGATCCTAGC TCACGGCGGC ATAGACGACG
 101 GCGACGAAGA AGAGGAGACC AACCAGCCAC CTCCGGCCAC CGGAACAACC
 151 ACCGTCGTGA ATCTCCGATC CAAAGGCTTG GTGCTTGTGA AGATCTACTG
 201 TATTATAATA CTCTTCTTTA GCACATTCTT AGCCGGAATT TCACCTTACT
 251 TTTACCGATG GAACGAGTCG TTTCTCCTCC TAGGAACTCA ATTCTCCGGT
 301 GGTATATTCC TCGCGACCGC TCTAATCCAt TTCCTCAGCG ACGCTAACGA
 351 GACTTTCCGA GGGTTAAAAC ACAAAGAGTA TCCTTACGCT TTCATGTTAG
 401 CAGCCGCTGG ATATTGCCTT ACAATGCTGG CAGATGTGGC GGtGCGTTT
 451 GTaGCGGCTG GGAgTAATAA CAACCACgTC GGAGcTAGCg TCGGAGAGTC
 501 GAGGGAGGAT GAtGACGTGG CAGtGAAAGA GGAAGGACgT CGTGAGATAA
 551 AGAGTGGTGT TGATGTGAGT CAAGCGcTTA TACGAACTAG TGGATTTGGA
 601 GACACAGCTT TGCTGATTTT TGCTCTTTGT TTTCACTCCA TCTTTGAGGG
 651 AATCGCCATT GGTCTCTCAG ACACTAAAAG CGACGCTTGG AGAAACCTAT
 701 GGACAATATC GTTGCACAAG GTCTTTGCGG CCGTAGCAAT GGGAATAGCT
 751 CTTCTCAAGC TAATCCCTAA ACGTCCATTC TTCCTCACTG TCGTCtACTC
 801 CTTCGCCtTT GGGAtATCGA GTCCCATAGG TGTCGGGATT GGCATTGGAA
 851 TCaATGCCac TAGCCAAGGA GCTGGTGGTG ACTGGACCtA CGCgATcTcT
 901 ATGGGGCTTG CGtGTGGAGT TTTtGTGTAC GTTGCGGTTA ACCAtCTCAT
 951 cTCAAAAGGG TATAAGCCTC TTGAGGAATG TtAcTTCGAC AAGCCAAtct
1001 ACAAGTTTAT TGcCGtCTtC CtCGGTGTTG CTTTGCtctC TGTTGTAAtG
1051 ATTTGGGATT G
```

*Fig. 19*

ZIP3 protein sequence

MKTKSVKLLFFFFSVSLLLIAVVNAAEGHSHGGPKCECSHEDDHENKAGARKYKIAAIPT
VLIAGIIGVLFPLLGKVFPSLRPETCFFFVTKAFAAGVILATGFMHVLPEAYEMLNSPCL
ISEAWEFPFTGFIAMIAAILTLSVDTFATSSFYKSHCKASKRVSDGETGESSVDSEKVQI
LRTRVIAQVLELGIIVHSVVIGISLGASQSPDAAKALFIALMFHQCFEGLGLGGCIAQGK
FKCLSVTIMSTFFAITTPIGIVVGMGIANSYDESSPTALIVQGVLNAASAGILIYMSLVD
LLAADFTHPKMQSNTGLQIMAHIALLLGAGLMSLLAKWA

ZIP3 nucleotide sequence

GTGTGAGTAATTTAGAAAGCCCTAATTTTAAATAAGATAGAGATTATGAAGACTAAGA
GCGTGAAACTCTTATTCTCTCCGTCTCCCTCTTCATCGCCGTCGTCAACG
CCGCCGAAGGCCATTCACATGGTGGACCAAATGTGAATGCTCACACGAAGACGACCATG
AAAACAAAGCCGGAGCTCGGAAATACAAGATCGCCGCAATTCCTACAGTTCTAATAGCCG
GCATAATCGGAGTTCTTTCTCGTCAAGTCTTCCCTTCTTGCGTCCAGAA
CATGTTTCTTCTTGCCTGAGCTTCGCAGCGGAGTTATCTTGGCTACCGGATTA
TGCATGTCTGAGGCTTACGAGATGCTTAACTCTCGAGATGCTTGATATCTGAAGCAT
GGGAATTTCCGTTCACGGATTATTGCGATCTTGACGTTATCCGTTG
ATACATTGCCACTTCGAGTTCTATAAATCGCATTGCAAAGCGTCTAAGAGGGTCAGTG
ATGGAGAAACCGGAGTCCTCCGTTGACTCGACTAATAGTACACTCAGTAGGTAATAGGAATATCAC
TTATTGCACAGGTATTGGAGTGGGAATAATGCTGCAAAAGCTCTGTTTATTGCCTTAATGTTTCATC
TAGGAGCTTCACAGAGCCCAGATGCTTGGTGGTTGTATTGCTCAGGGAAAATTCAAGTGTTGT
AATGCTTCGAAGGTCTAGGCCTTGACGTTCTTGTTATTGCTCAGGGAAAATTCAAGTGTTGT
CAGTAACAATCATGTCGACGTTCTTCGCAATAACGACACCGATAGGAATCGTTGTGGAA
TGGGAATAGCAAATTCTTACGAGTCTTCACCAAGCTCTGATCGTTCAAGGAGTTT
TGAACGCTGCATCCGCAGGCATTCTCATCTACATGTCTTTGGTTGACCTTCTCGCAGCAG
ATTTCACGCACCCTAAAATGCAATCCAATACTGGGCTTCAAATTATGGCCATATTGCTC
TCCTTCTTGGCTGGCCTCATGTTTTGCTCATGCCTTTATGCCACCTTGAATTCGAATTATTGTT
CAACTCTTCTAGTTTTCCCCTTTAACATTATACAATTGTGTATATTACTCACACTTCATGT
CTTATTTCCCCTTTAACATTATACAATTGTGTATATTACTCACACTTCATGT
ACTCATGTTTAACATTATACAATTACTAAATTACTCACACTCTGAAACACTTCATGT
AAAAAAAAAAAAAAAAAAAACTAAATTACTCACACTCTGAAACACTTCATGT
CTCCAGCTTTGTTCCCTTAGTGAGGGTAATTTCGAGCTTGGCGTAATCATA

*Fig. 20*

ZRT1 Nucleotide Sequence

```
   1 atgagcaacg ttactacgcc gtggtggaaa caatgggacc cttctgaagt
  51 tacacttgcc gataaaaccc ctgatgatgt gtggaagacc tgtgttttgc
 101 aaggtgttta ctttggtgga aacgagtaca atggtaactt aggtgccaga
 151 atatcttccg tctttgttat tcttttcgtg agtactttt tcaccatgtt
 201 cccattaatc tcaacaaaag tgaaaagatt gagaattcct ctatatgttt
 251 accttttcgc aaagtatttt ggttccggtg ttattgttgc aaccgcattt
 301 atccacttaa tggaccctgc ttatggtgcg attggtggta ccacttgtgt
 351 aggacaaacc ggtaactggg gtctttattc atggtgtcct gccattatgc
 401 taacgagttt gaccttcact ttccttactg atctattcag tagcgtctgg
 451 gttgaaagaa agtatggtct ttcccatgac catacccacg atgaaattaa
 501 agacactgtt gtgagaaaca ctgcagctgt ttcaagtgag aatgacaatg
 551 agaatggtac tgcaaatgga tctcatgaca ccaagaacgg agtagagtat
 601 tatgaagatt cagacgctac atccatggat gttgttcaat catttcaagc
 651 acaattttat gccttttaa ttttagaatt cggtgtgatt ttccactccg
 701 ttatgatcgg tctaaacctg ggaagtgttg gtgatgagtt ctcctcccta
 751 tacccctgtct tagtgttcca tcaatcattt gaaggtttag gtattggtgc
 801 aagattgtca gccattgaat tccctagatc aaagagatgg tggccatggg
 851 ccctatgtgt tgcgtatggg ttaaccacac caatctgtgt ggccatcggt
 901 ttgggtgttc gtaccagata cgtcagcggt tcttacactg cgcttgttat
 951 ctctggtgtt tggatgcca tttctgctgg tatcttattg tacactggtt
1001 tggttgaact actagcaaga gactttatat tcaatcctca agaacaaag
1051 gatctaagag aattgtcctt caacgttata tgcactcttt tcggtgctgg
1101 tatcatggct ttgatcggta agtgggctta a
```

ZRT1 Amino Acid Sequence

```
   1 MSNVTTPWWK QWDPSEVTLA DKTPDDVWKT CVLQGVYFGG NEYNGNLGAR
  51 ISSVFVILFV STFFTMFPLI STKVKRLRIP LYVYLFAKYF GSGVIVATAF
 101 IHLMDPAYGA IGGTTCVGQT GNWGLYSWCP AIMLTSLTFT FLTDLFSSVW
 151 VERKYGLSHD HTHDEIKDTV VRNTAAVSSE NDNENGTANG SHDTKNGVEY
 201 YEDSDATSMD VVQSFQAQFY AFLILEFGVI FHSVMIGLNL GSVGDEFSSL
 251 YPVLVFHQSF EGLGIGARLS AIEFPRSKRW WPWALCVAYG LTTPICVAIG
 301 LGVRTRYVSG SYTALVISGV LDAISAGILL YTGLVELLAR DFIFNPQRTK
 351 DLRELSFNVI CTLFGAGIMA LIGKWA
```

*Fig. 21*

ZRT2 Nucleotide Sequence

```
   1 atggttgatc ttatagcgag ggatgactcc gtagatactt gccaagcttc
  51 taacggctac aatgggcacg caggtcttag aattctggca gtattcatta
 101 tactgatatc gtcaggattg ggagtttatt tcccaatttt gtcatcacgg
 151 tattcgttta taaggctacc aaattggtgc tttttcatag cgaagttctt
 201 cggttctggt gtcattgttg ccacagcgtt cgttcatctt ctacagcccg
 251 cagccgaagc tctgggagat gaatgtcttg gtggcacatt tgccgaatat
 301 ccatgggctt tgggatctg tttaatgtcg cttttcttac ttttcttcac
 351 tgaaatcatc acgcattatt ttgtagcgaa aacgctggga cacgatcatg
 401 gggaccatgg ggaagttacc agtattgatg ttgatgctcc cagttcggga
 451 tttgtcatca gaaatatgga ctcggatcct gtatctttca ataacgaagc
 501 tgcctactcc atccataatg acaaaactcc gtacactact agaaatgaag
 551 agattgtcgc tactcctata aaggaaaaag aacccggctc aaatgttact
 601 aattatgatc tggaaccggg aaaaacagag tcactagcta atgaactagt
 651 tccaaccagt tcccatgcga caaatctcgc ttctgtacct ggaaaagatc
 701 attattctca cgaaaatgac catcaagatg tctcccagtt ggccacacgt
 751 atcgaggagg aagataaaga gcagtatctc aatcagatac tagctgtttt
 801 tattctagaa tttggcatca tctttcactc tgtatttgtg ggtctttcgc
 851 tatctgtcgc gggtgaagaa ttcgaaacct tatttatcgt tttaactttc
 901 caccaaatgt tcgaaggttt gggtctaggc acaagagttg ccgaaacgaa
 951 ttggccagaa agtaagaagt acatgccttg gttaatggga ttagccttca
1001 ctttaacgtc acccatagca gtcgcggtag gtattggtgt cagacactct
1051 tggataccctg gctctagaag agcattaatt gctaatggtg tttttgactc
1101 gatatcatca ggaattctta tttatactgg actagtcgaa ttaatggctc
1151 atgaattctt atactctaat caattcaaag gacctgatgg cctcaaaaaa
1201 atgcttagtg catatctcat catgtgttgt ggagctgctt taatggctct
1251 tctagggaaa tgggcatag
```

FIG.22A

ZRT2 Amino Acid Sequence

```
  1 MVDLIARDDS VDTCQASNGY NGHAGLRILA VFIILISSGL GVYFPILSSR
 51 YSFIRLPNWC FFIAKFFGSG VIVATAFVHL LQPAAEALGD ECLGGTFAEY
101 PWAFGICLMS LFLLFFTEII THYFVAKTLG HDHGDHGEVT SIDVDAPSSG
151 FVIRNMDSDP VSFNNEAAYS IHNDKTPYTT RNEEIVATPI KEKEPGSNVT
201 NYDLEPGKTE SLANELVPTS SHATNLASVP GKDHYSHEND HQDVSQLATR
251 IEEEDKEQYL NQILAVFILE FGIIFHSVFV GLSLSVAGEE FETLFIVLTF
301 HQMFEGLGLG TRVAETNWPE SKKYMPWLMG LAFTLTSPIA VAVGIGVRHS
351 WIPGSRRALI ANGVFDSISS GILIYTGLVE LMAHEFLYSN QFKGPDGLKK
401 MLSAYLIMCC GAALMALLGK WA
```

FIG.22B

IRT2 peptide sequence (345 aa)

```
  1 DPRVRLILFT FTVSPAISTA PEHCDSGFDN PCINKAKALP LKIVAIVAIL
 51 TTSLIGVTSP LFSRYISFLR PDGNGFMIVK CFSSGIILGT GFMHVLPDSF
101 EMLSSKCLSD NPRHKFPSGG LVAMMSGLVT LAIDSITTSL YTGKNSVGPV
151 PDEEYGIDQE KAIHMVGHNH SHGHGVVLAT KDDGQLLRYQ VIAMVLEVGI
201 LFHSVVIGLS LGATNDSCTI KGLIIALCFH HLFEGIGLGG CILQADFTNV
251 KKFLMAFFFT GTTPCGIFLG IALSSIYRDN SPTALITIGL LNACSAGMLI
301 YMALVDLLAT EFMGSMLQGS IKLQIKCFTA ALLGCAVMSV VAVWA
```

·····

IRT2 nucleotide sequence

```
   1 TCGACCCACG CGTCCGCCTC ATCCTATTCA CCTTCACCGT ATCTCCGGCG
  51 ATCTCAACGG CCCCGGAACA TTGTGATAGC GGCTTTGATA ACCCGTGCAT
 101 CAACAAAGCT AAGGCTTTAC CACTCAAAAT CGTAGCCATT GTTGCCATAC
 151 TTACAACAAG CTTGATAGGC GTGACCTCTC CTCTTTTCAG CCGTTACATT
 201 TCGTTCCTCC GTCCCGATGG CAATGGTTTC ATGATCGTCA ATGTTTTTC
 251 TTCTGGAATC ATCCTTGGAA CCGGTTTCAT GCACGTCTTG CCTGACTCTT
 301 TCGAGATGTT GTCATCGAAA TGTCTTAGTG ATAATCCGCG GCATAAGTTC
 351 CCTTCTGGGG GTTTAGTCGC TATGATGTCC GGTCTAGTCA CTCTAGCCAT
 401 TGACTCCATT ACCACCAGCC TTTATACCGG TAAGAACTCA GTCGGACCAG
 451 TGCCTGATGA AGAGTATGGC ATTGATCAAG AGAAAGCGAT TCACATGGTA
 501 GGCCACAATC ATAGTCACGG TCATGGTGTA GTGCTAGCAA CTAAAGATGA
 551 TGGACAGCTT TTGCGCTACC AAGTCATTGC CATGGTATTG GAGGTTGGGA
 601 TTTTATTTCA TTCTGTGGTC ATTGGACTAT CTCTAGGAGC AACTAATGAT
 651 TCATGTACCA TTAAAGGACT CATCATAGCT CTTTGCTTCC ATCACTTGTT
 701 CGAAGGCATA GGTCTTGGTG GCTGCATCCT CCAGGCAGAT TTTACAAATG
 751 TGAAGAAGTT CTTGATGGCA TTCTTTTTCA CTGGAACAAC ACCTTGTGGT
 801 ATCTTTCTTG GAATCGCATT GTCGAGTATC TATAGAGATA ACAGTCCAAC
 851 CGCGTTGATT ACGATTGGAC TGTTAAATGC TTGCTCGGCC GGAATGCTCA
 901 TCTACATGGC CCTCGTCGAC CTTCTAGCTA CCGAGTTCAT GGGGTCAATG
 951 CTCCAAGGTA GCATCAAACT TCAGATCAAG TGCTTCACGG CGGCTTTGCT
1001 TGGCTGCGCC GTAATGTCGG TCGTCGCCGT GTGGGCTTAA ACACTCTTTC
1051 AACATAATCA ATAAATTATT TGATTTATTA ATCCAGGCGA CCAATACTTT
1101 CGCCTTTGGA AAATTGAGTT TTTGTTTTTA AGTTTGAATC ATTTATTAGT
1151 TTGTATAGTG CATGTAAGCG TTTGAAAGAA ATTTCTTTTT ATGACATTGT
1201 AAATTTATTT TTATGGATGC GATGTTTACT TTCTTAAAAA AAAAAAAAA
1251 AAAAAAAAAA AAAAA
```

*Fig. 23*

METAL-REGULATED TRANSPORTERS AND USES THEREFOR

RELATED APPLICATIONS

This application is a divisional application of Ser. No. 09/107,858 filed on Jun. 30, 1998, now U.S. Pat. No. 6,162,900, which in turn is a divisional application of Ser. No. 08/758,621 filed on Nov. 27, 1996, U.S. Pat. No. 5,846,821, which is in turn a CIP of 60/018,578 filed on May 29, 1996.

This application claims the benefit of the previously filed U.S. Provisional Application Ser. No. 60/018,578, filed May 29, 1996, the contents of which are hereby incorporated by reference.

This invention was made with government support under MCB-94056200 awarded by the National Science Foundation and GM48139 awarded by the National Institutes of Health. The government has certain rights in this invention.

BACKGROUND OF THE INVENTION

Iron deficiency is one of the most common human nutritional disorders in the world today (Yip, R. (1994) *J. Nutr.* 124: 1479S–1490S). Indeed, iron is an essential nutrient for virtually all organisms because it plays a critical role in important biochemical processes such as respiration and photosynthesis. Although abundant in nature, iron is often available in limited amounts because the oxidized form, Fe(III), is extremely insoluble at neutral or basic pH. This fact is of particular importance to agriculture because approximately one-third of the world's soils are classified as iron-deficient (Yi, Y. et al. (1994) *Plant Physiol.* 104: 815–820). Many "iron-efficient" plant varieties have iron uptake strategies (designated strategy I or strategy II) that, not surprisingly, are directed at solubilizing iron (Römheld, V. (1987) *Physiol. Plant.* 70: 231–234). Strategy II plants, which include all of the grasses, release Fe(III) compounds called "phytosiderophores" into the surrounding soil that bind iron and are then taken up into the roots. Most other iron-efficient plants use strategy I and respond to iron deprivation by inducing the activity of membrane-bound Fe(III) chelate reductases that reduce Fe(III) to the more soluble Fe(II) form. The Fe(II) product is then taken up into the roots by an Fe(II) specific transport system that is also induced by iron-limiting growth conditions. Furthermore, the roots or strategy I plants release more protons when iron-deficient, lowering the rhizosphere pH and thereby increasing the solubility of Fe(III). Thus, it would be desirable to take advantage of this understanding of iron-uptake strategies to produce plants which have increased iron-uptake capabilities.

Furthermore, another metal, zinc, is an integral cofactor of many proteins and is indispensable to their catalytic activity and/or structural stability (Vallee and Auld (1990) *Biochemistry* 9:5647–5659). Moreover, zinc is a ubiquitous component of enzymes involved in transcription and of accessory transcription factors, the zinc finger proteins, that regulate gene expression (Rhodes and Klug (1993) *Sci. Am.* 268(2): 56–65). Because of the many roles this metal plays in cellular biochemistry, zinc is an essential nutrient for all organisms. Despite this importance, very little is known about the molecular mechanisms cells use to obtain zinc. No transporter genes involved in zinc uptake (i.e. influx transporters) have been isolated from any organism. Recently, genes have been identified whose products are responsible for detoxifying intracellular zinc by transporting the metal from the cytoplasm to the cell exterior or into intracellular compartments (i.e. efflux transporters). These genes include the closely related eukaryotic genes, COT1, ZRC1, and Znt-1 (Conklin et al. (1992) *Mol. Cell Biol.* 12:3678–3688; Kamizono et al. (1989) *Mol. Gen. Genet.* 219:161–167; Palmiter and Findley (1995) *EMBO J.* 14:639–649). While important for zinc detoxification, these genes do not appear to play a role in zinc uptake.

In addition, metal ion pollution is perhaps one of the most difficult environmental problems facing the industrial world today. Unlike the organic and even halogenated organic pollutants, which can be degraded in the soil, metals are essentially nonmutable. The electrolytic, in situ immobilization and chemical leaching technologies for cleaning polluted sites are all very expensive, particularly in light of how vast some of these sites are. With the exception of approaches like vitrification, most in situ metal ion remediation schemes require some mechanism for increased mobilization of the metal ion. This raises the possibility of further endangering local wildlife or adjacent ecosystems not already affected. Thus, a need still exists for better methods for removing toxic pollutants from the soil.

Accordingly, an object of the invention is to generate transgenic plants in which expression of an MRT polypeptide is altered such that metal-uptake is increased.

Another object of the invention to provide methods for removing toxic pollutants, such as heavy metals, from the environment.

Yet another object of the invention is to provide methods for improving human or animal nutrition, e.g., for treating metal-deficiency, e.g., iron-deficiency or zinc-deficiency.

SUMMARY OF THE INVENTION

This invention is based, at least in part, on the discovery of a family of polypeptides, designated herein as metal-regulated transporter, MRT, polypeptides, which share several structural/functional properties, at least one of which is related to metal transport. Structurally, the MRT polypeptides include, for example, at least one transmembrane binding domain which has at least about 40%, more preferably at least about 50%, 55%, 60%, 70%, 80% or 90% amino acid sequence identity with an amino acid sequence shown in SEQ ID NO:2, SEQ ID NO:4, SEQ ID NO:6, SEQ ID NO:8 or SEQ ID NO:14 and/or at least one histidine rich domain. Functionally, the MRT polypeptides are capable of, for example, transporting metals, e.g., Fe, e.g., Fe(II), Cd, Co, Mn, Pb, Hg and/or Zn.

Preferred MRT polypeptides have an overall amino acid sequence identity of at least about 40%, preferably at least about 42%, 45%, 47%, 50%, more preferably at least about 55%, 60%, 70%, 80%, 90%, or 95% with an amino acid sequence of SEQ ID NO:2, SEQ ID NO:4, SEQ ID NO:6, SEQ ID NO:8 or SEQ ID NO:14; it has eight transmembrane domains; it has four histidine rich domains; or it can be isolated from the Arabidopsis family of plants.

Accordingly, this invention pertains to isolated nucleic acid molecules encoding an MRT polypeptide. Such nucleic acid molecules (e.g., cDNAs) have a nucleotide sequence encoding an MRT polypeptide (e.g., an *A. thaliana* IRT1 polypeptide, an *A. thaliana* IRT2 polypeptide, an *A. thaliana* ZIP1 polypeptide, an *A. thaliana* ZIP2 polypeptide, or an *A. thaliana* ZIP3 polypeptide) or biologically active portions or fragments thereof, such as a polypeptide having an MRT bioactivity. In a preferred embodiment, the isolated nucleic acid molecule has a nucleotide sequence shown in SEQ ID NO:1, SEQ ID NO:3, SEQ ID NO:5, SEQ ID NO:7 or SEQ ID NO:13, or a portion or fragment thereof. Preferred regions of these nucteotide sequences are the coding regions. Other preferred nucleic acid molecules are those which have at least about 45%, preferably at least about 48%, more preferably at least about 50%, and most preferably at least about 55%, 60%, 70%, 80%, 90%, 95%, 97% or 98% or more nucleotide sequence identity over the entire sequence with a nucleotide sequence shown in SEQ ID NO:1, SEQ ID NO:3, SEQ ID NO:5, SEQ ID NO:7 or SEQ ID NO:13, or a portion or fragment thereof. Nucleic acid molecules which hybridize under stringent conditions to the nucleotide sequence shown in SEQ ID NO:1, SEQ ID NO:3, SEQ ID NO:5, SEQ ID NO:7 or SEQ ID NO:13, e.g., nucleic acid molecules which hybridize to at least 6 consecutive nucleotides of the nucleotide sequence shown in SEQ ID NO:1, SEQ ID NO:3, SEQ ID NO:5, SEQ ID NO:7 or SEQ ID NO:13, are also within the scope of the invention. Such portions or fragments include nucleotide sequences which encode, for example, polypeptide domains having an MRT bioactivity. Examples of portions or fragments of nucleic acid molecules which encode such domains include portions or fragments of nucleotide sequences of SEQ ID NO:1, SEQ ID NO:3, SEQ ID NO:5, SEQ ID NO:7 or SEQ ID NO:13 which encode one or more of the following: at least one transmembrane domain which has at least about 40%, more preferably at least about 50%, 55%, 60%, 70%, 80% or 90% amino acid sequence identity with an amino acid sequence shown in SEQ ID NO:2, SEQ ID NO:4, SEQ ID NO:6, SEQ ID NO:8 or SEQ ID NO:14 or at least one histidine rich domain. Nucleic acid molecules of the present invention which further comprise a label are also within the scope of the invention. Complements of the nucleic acid molecules of the present invention are also specifically contemplated.

In another embodiment, the nucleic acid molecules of the invention encode a polypeptide having an amino acid sequence shown in SEQ ID NO:2, SEQ ID NO:4, SEQ ID NO:6, SEQ ID NO:8 or SEQ ID NO:14, or a portion or fragment thereof having a biological activity, e.g., an MRT bioactivity. Nucleic acid molecules encoding a polypeptide having at least about 40%, preferably at least about 42%, 45%, 47%, 50%, more preferably at least about 52%, and most preferably at least about 55%, 60%, 70%, 80%, 90%, 95%, 97% or 98% amino acid sequence identity over the entire sequence with an amino acid sequence shown in SEQ ID NO:2, SEQ ID NO:4, SEQ ID NO:6, SEQ ID NO:8 or SEQ ID NO:14, or a portion or fragment thereof having a biological activity, e.g., an MRT bioactivity, are also within the scope of the invention.

Another aspect of the invention pertains to nucleic acid molecules which encode polypeptides which are fragments of at least about 20 amino acid residues in length, more preferably at least about 30 amino acid residues in length or more, of an amino acid sequence shown in SEQ ID NO:2, SEQ ID NO:4, SEQ ID NO:6, SEQ ID NO:8 or SEQ ID NO:14. Other aspects of the invention pertain to nucleic acid molecules which encode polypeptides which are fragments of at least about 20 amino acid residues in length, more preferably at least about 30 amino acid residues in length which have at least about 40%, more preferably at least about 42%, 45%, 47%, 50%, and most preferably at least about 55%, 60%, 70%, 80%, 90% or more (e.g., 95%, 97–98%) amino acid sequence identity over the entire sequence with an amino acid sequence shown in SEQ ID NO:2, SEQ ID NO:4, SEQ ID NO:6, SEQ ID NO:8 or SEQ ID NO:14, or a portion or fragment thereof having a biological activity, e.g., an MRT bioactivity. Portions or fragments of the polypeptides encoded by the nucleic acids of the invention include polypeptide regions which comprise, for example, various structural and/or functional domains of MRT family members. Such domains include portions or fragments of nucleotide sequences of SEQ ID NO:1, SEQ ID NO:3, SEQ ID NO:5, SEQ ID NO:7 or SEQ ID NO:13 which encode one or more of the following: at least one transmembrane domain which has at least about 40%, more preferably at least about 50%, 55%, 60%, 70%, 80% or 90% amino acid sequence identity with an amino acid sequence shown in SEQ ID NO:2, SEQ ID NO:4, SEQ ID NO:6, SEQ ID NO:8 or SEQ ID NO:14, or at least one histidine rich domain. Nucleic acid molecules which are antisense to the nucleic acid molecules described herein are also within the scope of the invention.

Another aspect of the invention pertains to vectors, e.g., recombinant expression vectors, containing the nucleic acid molecules of the invention and host cells into which such recombinant expression vectors have been introduced. In one embodiment, such a host cell is used to produce an MRT polypeptide by culturing the host cell in a suitable medium. An MRT polypeptide protein can be then isolated from the medium or the host cell.

Still another aspect of the invention pertains to isolated MRT polypeptides (e.g., isolated *A. thaliana* IRT1 polypeptides) and active fragments thereof, such as peptides having an activity of an MRT polypeptide (e.g., at least one biological activity of an IRT1 polypeptide as described herein). The invention also provides an isolated or purified preparation of an MRT polypeptide. In preferred embodiments, an MRT polypeptide comprises an amino acid sequence of SEQ ID NO:2, SEQ ID NO:4, SEQ ID NO:6, SEQ ID NO:8 or SEQ ID NO:14. In other embodiments, the isolated MRT polypeptide comprises an amino acid sequence having at least about 40%, more preferably at least about 42%, 45%, 47%, 50%, and most preferably at least about 55%, 60%, 70%, 80%, 90% (e.g., 95%, 97%–98%) or more amino acid sequence identity over the entire sequence with an amino acid sequence of SEQ ID NO:2, SEQ ID NO:4, SEQ ID NO:6, SEQ ID NO:8 or SEQ ID NO:14, and, preferably has an activity of an MRT polypeptide (e.g., at least one biological activity of MRT). Preferred MRT polypeptides include, for example, at least one transmembrane binding domain which has at least about 40%, more preferably at least about 50%, 55%, 60%, 70%, 80% or 90% amino acid sequence identity with an amino acid sequence shown in SEQ ID NO:2, SEQ ID NO:4, SEQ ID NO:6, SEQ ID NO:8 or SEQ ID NO:14, and/or at least one histidine rich domain. Preferred MRT polypeptides are capable of, for example, transporting metals, e.g., Fe, e.g., Fe(II), Cd, Co, Mn, Pb, Hg and/or Zn.

Fragments of the MRT polypeptides of the invention can include portions or fragments of the amino acid sequences shown in SEQ ID NO:2, SEQ ID NO:4, SEQ ID NO:6, SEQ ID NO:8 or SEQ ID NO:14, which are at least about 20 amino acid residues, at least about 30, or at least about 40 or more amino acid residues in length. The MRT polypeptide portions or fragments described herein can have an MRT bioactivity, e.g., one or more, in any combination, of the MRT biological activities described herein. Portions or fragments of the polypeptides of the invention can include polypeptide regions which comprise, for example, various structural and/or functional domains. Such domains include portions or fragments of amino acid sequences of SEQ ID NO:2, SEQ ID NO:4, SEQ ID NO:6, SEQ ID NO:8 or SEQ ID NO:14, which include at least one of the following: a transmembrane domain which has at least about 40%, more preferably at least about 50%, 55%, 60%, 70%, 80% or 90% amino acid sequence identity with an amino acid sequence shown in SEQ ID NO:2, SEQ ID NO:4, SEQ ID NO:6, SEQ ID NO:8 or SEQ ID NO:14, or a histidine rich domain. Preferred amino acid sequences of each of these domains are described herein. The peptide fragments can be modified to alter MRT bioactivity, e.g., impart a non-wild type activity on MRT polypeptides, or to impart desired characteristics thereon, e.g., increased solubility, enhanced therapeutic or prophylactic efficacy, or stability. Such modified peptides are considered functional equivalents of peptides having an activity of MRT as defined herein. A modified peptide can be produced in which the amino acid sequence has been altered, such as by amino acid substitution, deletion, or addition. In another embodiment, a component which imparts a desired characteristic on a peptide can be linked to the peptide to form a modified peptide.

The invention also provides for an MRT fusion polypeptide comprising an MRT polypeptide and a second polypeptide portion having an amino acid sequence from a protein unrelated to an amino acid sequence which has at least about 40% or more amino acid sequence identity with an amino acid sequence shown in SEQ ID NO:2, SEQ ID NO:4, SEQ ID NO:6, SEQ ID NO:8 or SEQ ID NO:14.

The invention also provides transgenic plants in which the expression of an MRT polypeptide is altered, as well as seeds and cells derived from such plants. For example, the invention includes a method for evaluating the effect of the expression or misexpression of an MRT gene on a parameter related to metal transport. The method includes providing a transgenic plant having an MRT transgene, or which otherwise misexpresses an MRT gene, contacting the transgenic plant with an agent, and evaluating the effect of the transgene or misexpression of the MRT gene on the parameter related to metal transport (e.g., by comparing the value of the parameter for a transgenic plant with the value for a control, e.g., a wild-type plant).

In addition, the transgenic plant, e.g., rice, beans, peas and maize, in which expression of an MRT polypeptide is altered can be incorporated into a pharmaceutical composition which includes the transgenic plant, or a portion thereof, and a pharmaceutically acceptable carrier. Such compositions can be used as human or animal nutritional supplements to provide, for example, iron to a subject with iron-deficiency or zinc to a subject with zinc-deficiency. Antibodies, e.g., monoclonal or polyclonal antibodies, which bind to an epitope of or are specifically reactive with an MRT polypeptide or fragment thereof are also specifically contemplated in the present invention.

Methods for identifying an agent which inhibits or activates/stimulates an MRT polypeptide are also within the scope of the invention. These methods include contacting a first polypeptide comprising a naturally occurring ligand of MRT, with a second polypeptide comprising an MRT polypeptide and an agent to be tested and determining binding of the second polypeptide to the first polypeptide. Inhibition of binding of the first polypeptide to the second polypeptide indicates that the agent is an inhibitor of an MRT polypeptide while activation/stimulation of binding of the first polypeptide to the second polypeptide indicates that the agent is an activator/stimulator or an MRT polypeptide.

In another aspect, the invention features a method for evaluating a candidate compound for the ability to interact with an MRT polypeptide. This method includes contacting the compound with the MRT polypeptide and evaluating the ability of the compound to interact with the MRT polypeptide. This method can be performed in vitro or in vivo.

The MRT polypeptides of the invention can be used to modulate metal concentrations in vitro or in vivo. In one aspect, the invention provides a method for modulating metal concentration in a biological sample containing the metal. This method includes providing a transgenic plant in which expression of an MRT polypeptide is altered and contacting the transgenic plant with the biological sample such that the metal concentration in the biological sample is modulated.

The invention further provides methods for removing a pollutant from soil. These methods include contacting a transgenic plant in which expression of an MRT polypeptide is altered with the soil such that the pollutant is removed from the soil. In a preferred embodiment, the pollutant is a metal, e.g., a metal selected from the group consisting of Pb, As, Co, Cu, Zn, Cd and/or Hg.

Additional methods of the invention include methods for treating a disorder associated with metal-deficiency, e.g., iron-deficiency or zinc-deficiency, in a subject. These methods include administering to a subject a therapeutically effective amount of a composition comprising a transgenic plant, or a portion thereof, in which expression of an MRT polypeptide is altered. In a preferred embodiment, the composition is administered in combination with a pharmaceutically acceptable carrier. In other preferred embodiments, the MRT polypeptide in the transgenic plant is overexpressed. In yet other preferred embodiments, the disorder associated with iron-deficiency is anemia.

Still additional methods of the invention include methods for promoting plant growth and/or survival. These methods include introducing into a plant a nucleic acid encoding an MRT polypeptide.

BRIEF DESCRIPTION OF THE DRAWINGS

FIG. 1A depicts the predicted amino acid sequence of the IRT1 protein. Amino acids are numbered on the left beginning with the initiator methionine residue. The signal sequence is underlined, the histidine-glycine repeats that form a metal-binding domain are in boldface and italic, and the putative membrane-spanning domains detected by the TOP PRED II program (Claros, M. G. et al. (1994) Comput. Appl. Biol. Sci. 10: 685–686) are boxed and numbered I–VIII.

FIG. 1B depicts the similarity of the IRT1 amino acid sequence to other plant sequences in the current sequence databases.

FIG. 4 depicts the nucleotide sequence of IRT1.

FIG. 5 depicts the amino acid sequence of IRT1.

Shown are the mean values of two experiments each performed in duplicate; error bars indicate±one standard deviation.

FIGS. 9A and 9B are bar graphs depicting regulation of the ZRT1 gene and zinc uptake. Shown are the mean values of two experiments each performed in duplicate. The standard deviation within each experiment was less than 10% of the corresponding mean.

Figure 10:
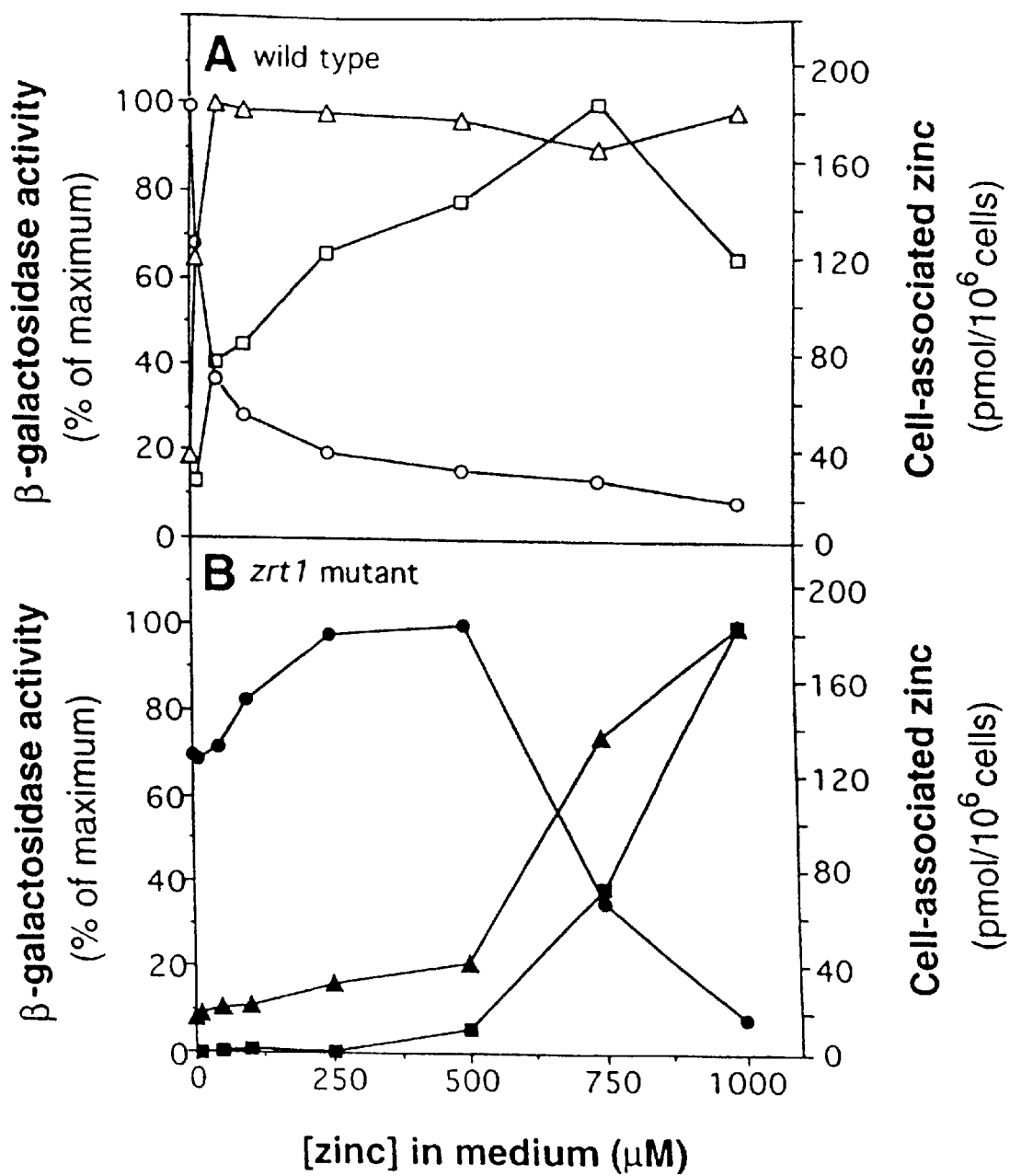

FIGS. 10A and 10B are graphs depicting effects of the zrt1 mutation on ZRT1 regulation and cell-associated zinc levels. Shown are the mean values of two experiments each performed in duplicate. The standard deviation within each experiment was less than 10% of the corresponding mean.

Figure 11A:
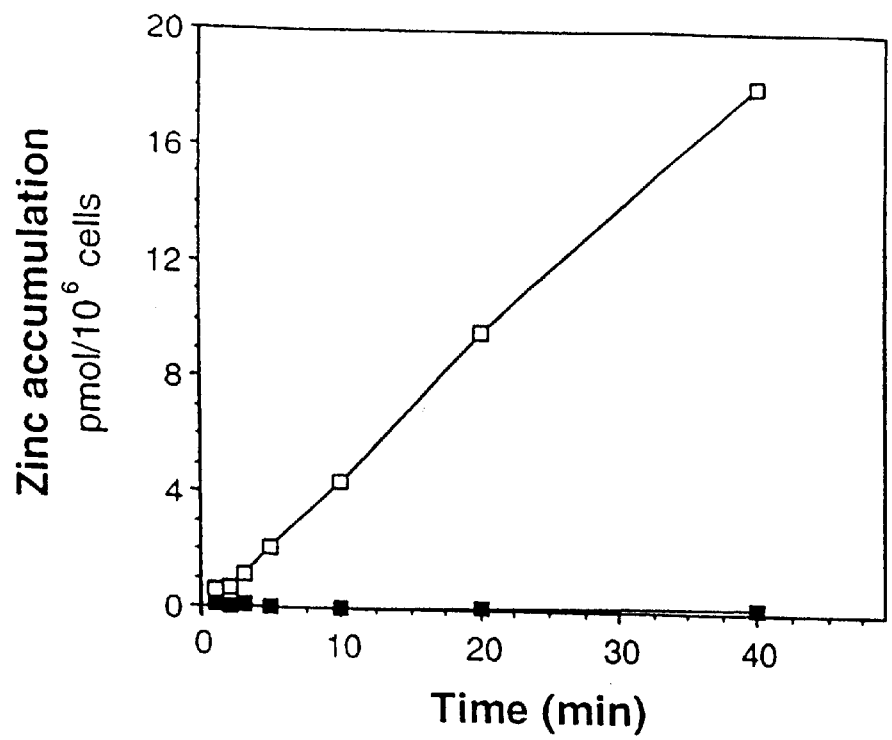
Figure 11B:
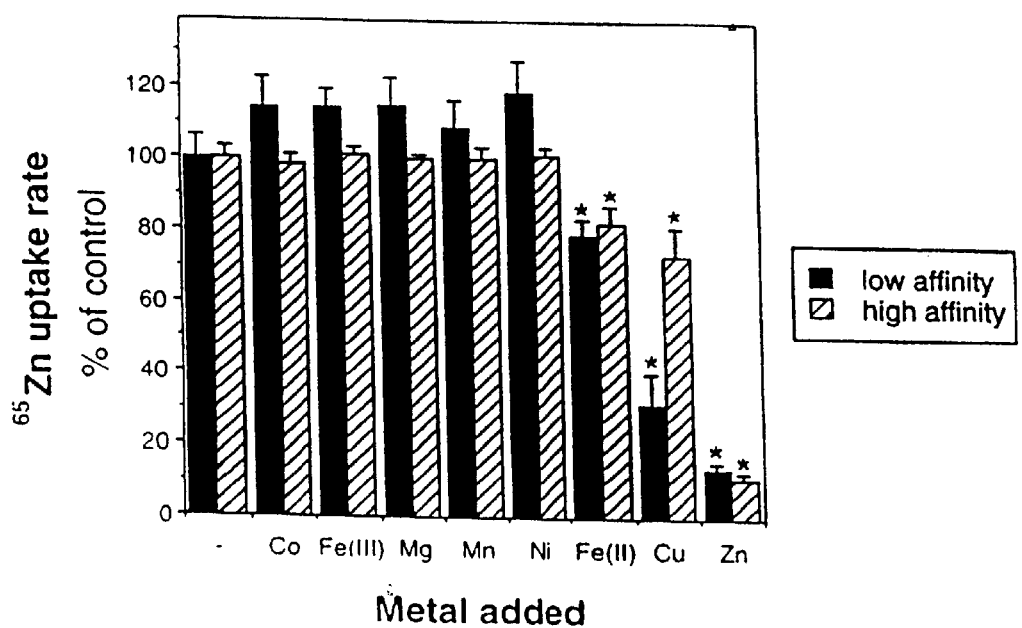

FIGS. 11A and 11B are graphs depicting biochemical properties of the low affinity zinc uptake system. Each value represents the mean of two separate experiments each performed in duplicate.

Figure 12:
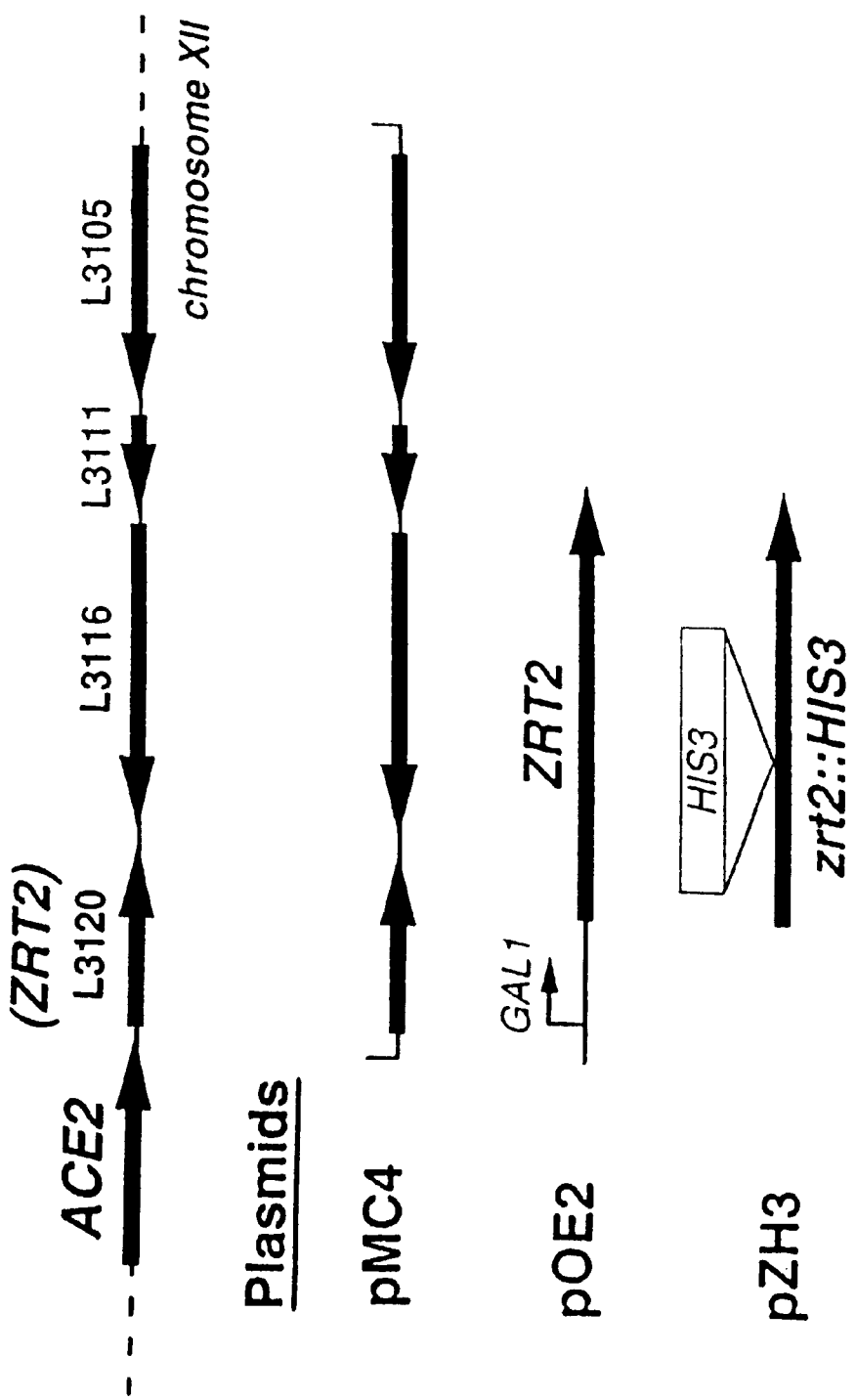

FIG. 12 depicts the chromosomal region of the ZRT2 gene and the plasmids used herein. The top line depicts a segment of yeast chromosome XII with open reading frames indicated by the arrows. The plasmids (pMC4, pOE2, and pZH3) are depicted below and the heterologous promoter in pOE2 is indicated by the arrow labeled GAL1.

Figure 13:
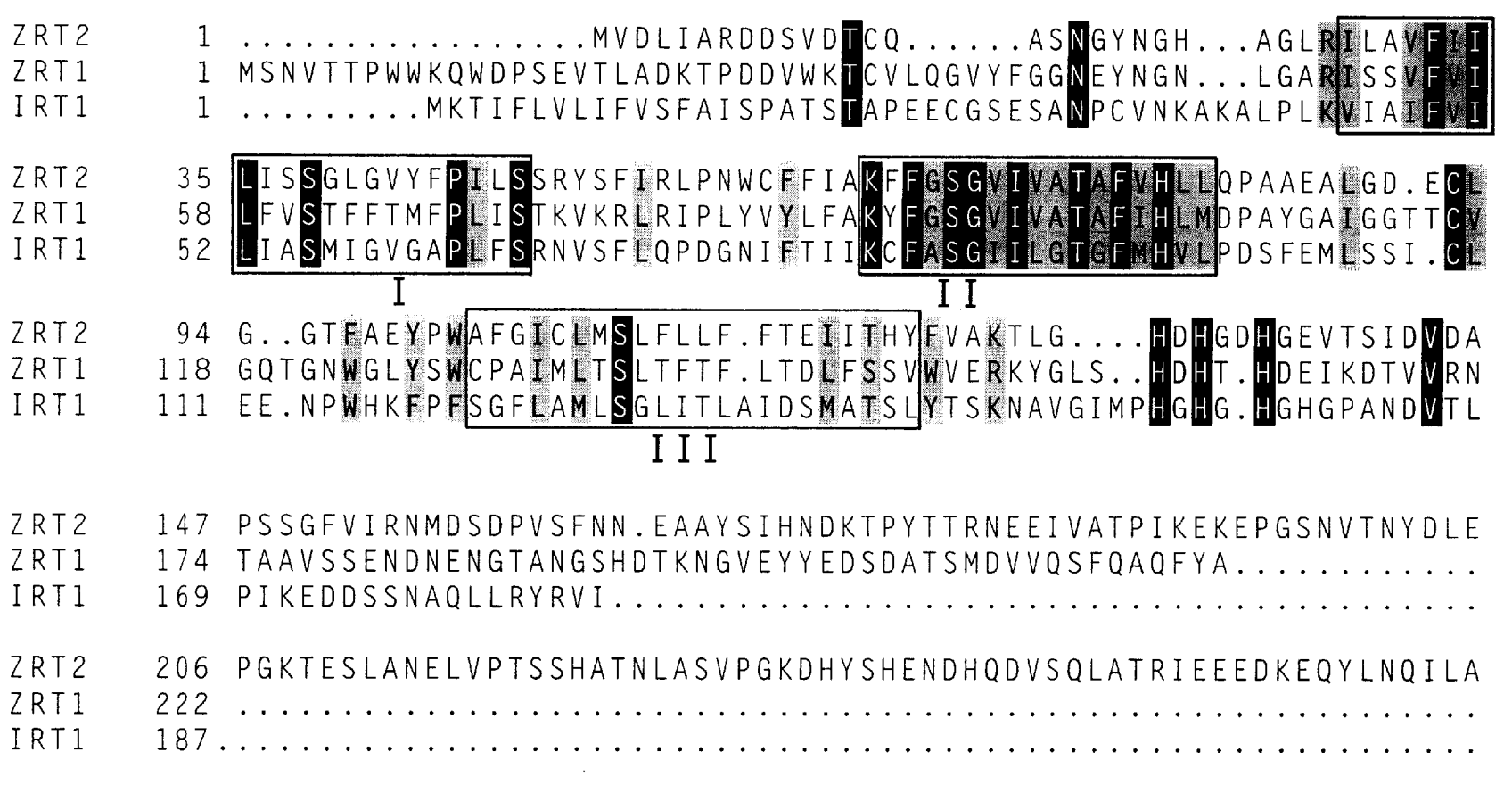

FIG. 13 depicts the predicted amino acid sequence of Zrt2p and its similarity to the amino acid sequences of Zrt1p and Irt1p. The black shading indicates positions of amino acid identity and the gray shading indicates conservative substitutions. The regions of Zrt2p that are predicted to be transmembrane domains are boxed and numbered I through VIII. The predicted transmembrane domains for Zrt1p and Irt1p are similarly located. The black circles indicate the amino acids comprising the putative metal-binding domain and the triangle indicates the position of the HIS3 insertion in the zrt2::HIS3 allele.

Figures 14A, 14B:
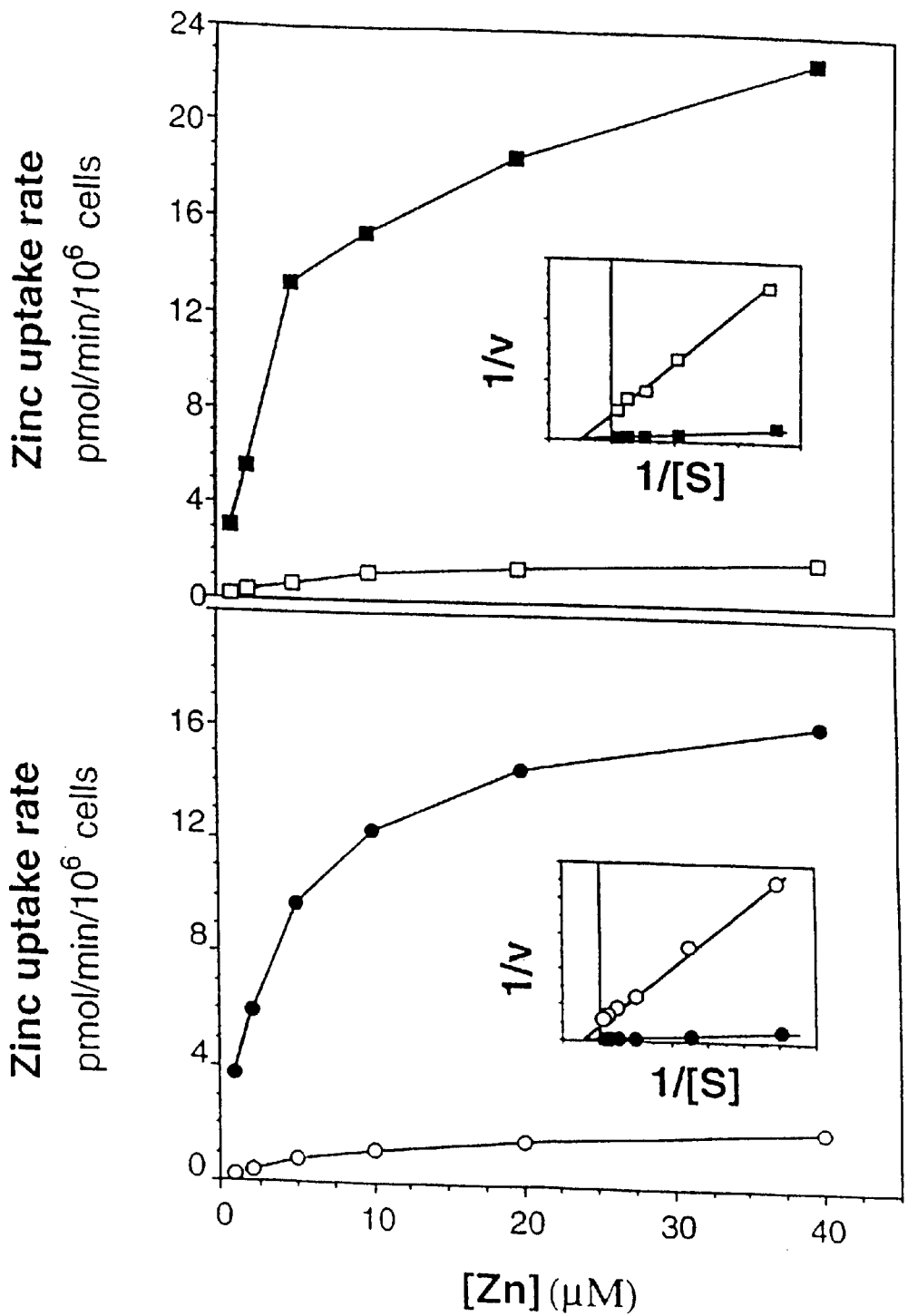

FIGS. 14A and 14B are graphs depicting data which demonstrates that ZRT2 overexpression increases the zinc uptake rate. The inset in each frame shows a Lineweaver-Burk reciprocal plot of the corresponding data. Each point represents the mean of two separate experiments each performed in duplicate. The standard deviation of each point was less than 15% of the corresponding mean.

FIGS. 15A and 15B are graphs depicting data which demonstrates that the ZRT2 gene is required for low but not high affinity uptake. Each point represents the mean of two separate experiments each performed in duplicate. The standard deviation of each point was less than 20% of the corresponding mean.

FIGS. 16A and 16B are graphs depicting effects of the zrt2 mutation on zinc levels required for growth. A representative experiment is shown.

Figure 17:
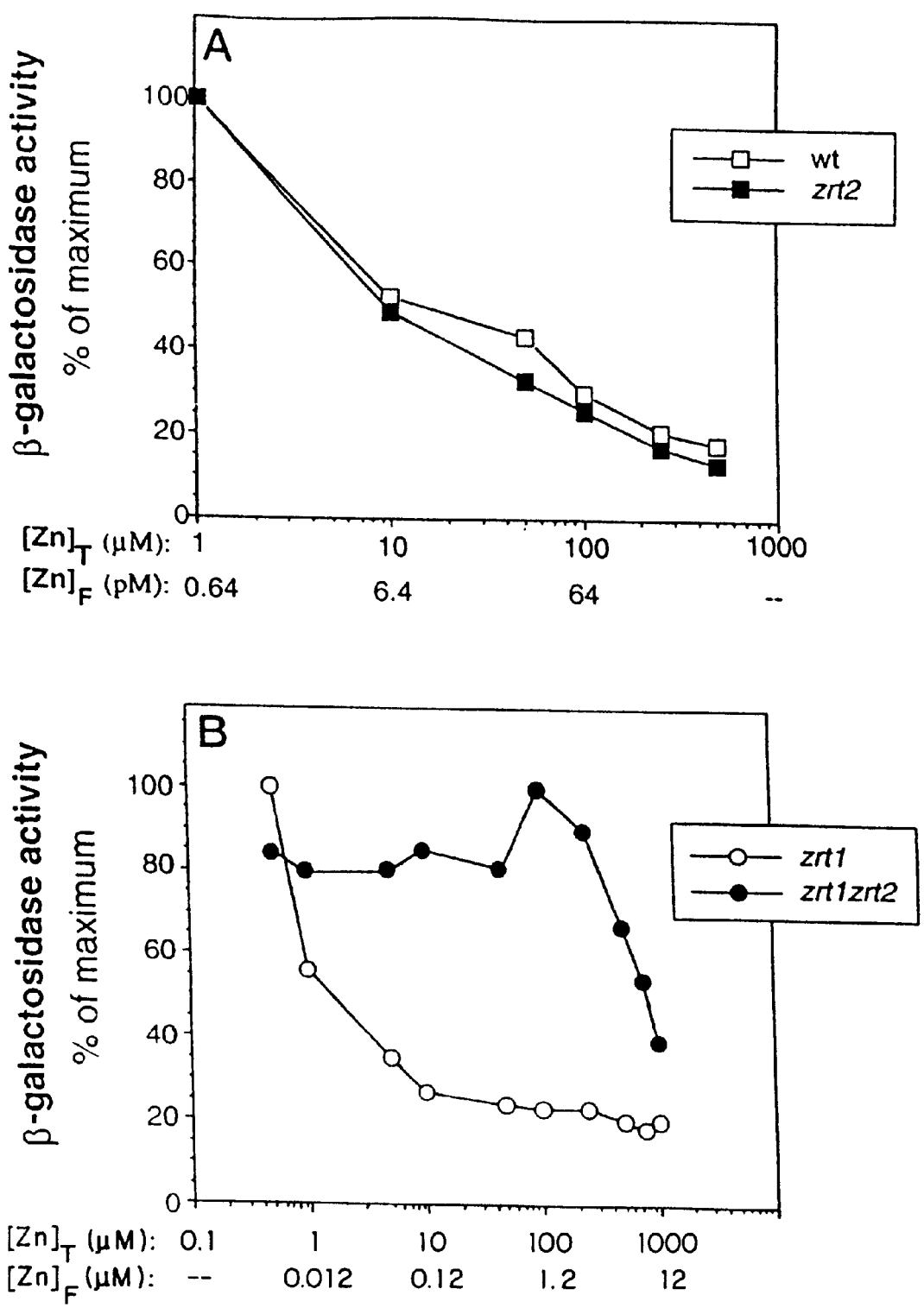

FIGS. 17A and 17B are graphs depicting the effect of the zrt2 mutation on the regulation of the ZRT1 promoter. Each point represents the mean of three separate experiments and the standard deviation of each point was less than 20% of the corresponding mean.

FIG. 18 depicts the nucleotide sequence and the corresponding amino acid sequence of ZIP1.

FIG. 19 depicts the nucleotide sequence and the corresponding amino acid sequence of ZIP2.

FIG. 20 depicts the nucleotide sequence and the corresponding amino acid sequence of ZIP3.

FIG. 21 depicts the nucleotide sequence and the corresponding amino acid sequence of ZRT1.

FIGS. 22A and 22B depict the nucleotide sequence and the corresponding amino acid sequence of ZRT2.

FIG. 23 depicts the nucleotide sequence and the corresponding amino acid sequence of IRT2.

Figure 24:
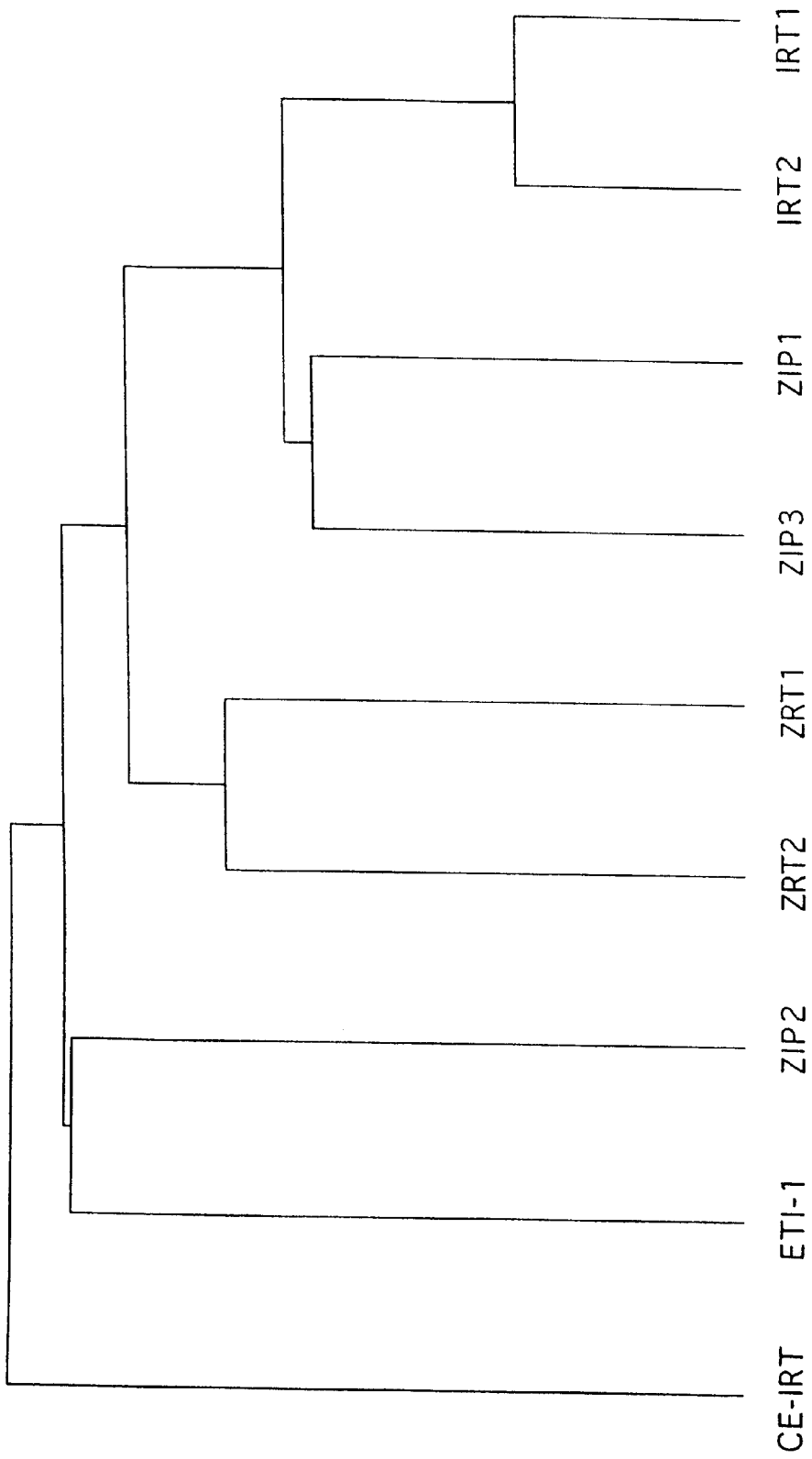

FIG. 24 depicts a dendogram showing total inferred sequence similarities among the deduced amino acid sequences of MRT family members. The tree was constructed using the GCG program PILEUP (Program Manual for the Wisconsin Package, version 8, 1994, Genetics Computer Group, Madison, Wis.). Several sub-families are apparent as groups in the dendogram.

DETAILED DESCRIPTION OF THE INVENTION

The IRT1, iron-regulated transporter, gene of the plant *Arabidopsis thaliana*, encoding an Fe(II) transporter, was cloned by functional expression in a yeast strain defective for iron uptake (GenBank™ accession #U27590). *Arabidopsis thaliana*, a common wall cress, is a small member of the mustard or crucifer family. Yeast expressing IRT1 posses a novel Fe(II) uptake activity that is strongly inhibited by Cd. IRT1 is an integral membrane protein with a metal-binding domain. Data base comparisons and Southern blot analysis indicated that IR1T is a member of a gene family in Arabidopsis. Related sequences were also found in the genomes of rice, yeast, nematodes, and humans. In Arabidopsis, IRT1 is expressed in roots, is induced by iron deficiency, and has altered regulation in plant lines bearing mutations that affect the iron uptake system. These results provide the first molecular insight into iron transport by plants.

Functional expression in yeast has been used to identify a gene that encodes an Fe(II) transporter expressed in the roots of the strategy I plant *Arabidopsis thaliana*. There is a striking similarity between iron uptake in strategy I plants and the mechanism of iron uptake in *Saccharomyces cerevisiae* (Yi, Y. et al. (1994) *Plant Physiol*. 104: 815–820). In *S. cerevisiae*, Fe(III) reductases in the plasma membrane reduce extracellular Fe(III) to Fe(II) (Lesuisse, E. et al. (1989) *J. Gen. Microbiol*. 135: 257–263; Dancis, A. et al. (1990) *Mol. Cell. Biol*. 10: 2294–2301; Eide, D. et al. (1992) *J. Biol. Chem*. 267: 20774–20781). The Fe(II) product is then taken up by either of two uptake systems. One system, with low affinity for substrate, requires the Fe(II) transporter encoded by the FET4 gene (Dix, D. R. et al. (1994) *J. Biol. Chem*. 269: 26092–26099). The second system has high affinity for Fe(II) and is induced under conditions of iron limitation. The high affinity system requires the FET3 multicopper oxidase for activity (Askwith, C. et al. (1994) *Cell* 76: 403–410; Dancis, A. et al. (1994) *Cell* 76: 393–402.). It has been proposed that FET3, as one component of a multisubunit transporter complex, is responsible for oxidizing Fe(II) back to Fe(III) during the transport process. Afet3 fet4 double mutant, although viable, is extremely sensitive to iron limitation (Dix, D. R. et al. (1994) *J. Biol. Chem*. 269: 26092–26099). The isolation and characterization of a gene from *A. thaliana*, IRT1, that suppresses the growth defect of a fet3 fet4 strain on iron-limited media is described herein. IRT1 is the first gene encoding an Fe(II) transporter to be cloned from plants or animals.

Comparisons of the IRT1 amino acid sequence with GenBank™, EMBL, and SWISS-PROT databases identified two additional MRT family members in Arabidopsis. Amino acids 8 through 127 of IRT1 are 72% (86 of 119) identical and 86% similar (i.e., identities plus conservative substitutions) to the predicted amino acid sequence of a cDNA partially sequenced as an EST T04324. Because of this high degree of similarity to IRT1, this gene has been designated IRT2 (SEQ ID NO:13). Furthermore, the carboxyl-terminal 47 amino acids of IRT1 are 45% (21 of 47) identical and 68% similar to the sequence of a partially sequenced open reading frame located downstream of the ferrodoxin-encoding FEDA gene (Somers, D. E. et al. (1990) *Plant Physiol.* 93: 572–577). This gene is referred to as IRT3.

Additional members of the MRT family of polypeptides were identified through a study of zinc uptake in *S. cerevisiae*. The yeast *Saccharomyces cerevisiae* provides an excellent model system in which to study zinc uptake in a eukaryotic cell. Biochemical assays of zinc uptake in yeast indicated that this process was transporter-mediated-i.e., uptake was dependent on time, temperature, and concentration and required metabolic energy (Fuhrmann, G. F. & Rothstein, A. (1968) *Biochim. Biophys. Acta* 163:325–330; White, C. & Gadd, G. M. (1987) *J. Gen. Microbiol.* 133:727–737; and Rothstein, A., Hayes, A., Jennings, D. & Hooper, D. (1958) *J. Gen. Physiol.* 41:585–594). Herein, the presence of two separate zinc uptake systems in *S. cerevisiae* is demonstrated. One system has high affinity for zinc, and its activity markedly increases in zinc-limited cells. The second system has a lower affinity for zinc and is not highly regulated by zinc availability. A gene, ZRT1 (for zinc-regulated transporter) (SEQ ID NO:9), has been characterized and identified because of its significant similarity to IRT1. The results described in greater detail herein indicate that Zrt1p is the zinc transporter protein of the high-affinity uptake system. The ZRT1 is the first influx zinc transporter gene from any organism to be characterized at the molecular level, and it is a member of the MRT family of proteins identified in fungi, nematodes, plants, and humans.

The second system for zinc uptake in yeast has a lower affinity for substrate (apparent $K_m=10$ $\mu$M), and it is active in zinc-replete cells. Low affinity uptake was unaffected by the zrt1 mutation, demonstrating that this system is a separate uptake pathway for zinc. Another member of the MRT gene family, ZRT2 (SEQ ID NO:11), was identified in the sequence data bases because of the close sequence similarity of its product to IRT1 and ZRT1. The analysis of ZRT2 demonstrates that this gene encodes the transporter protein of the low affinity system.

Complementation studies using zrt1zrt2 yeast strains allowed for identification of the three additional MRT family members ZIP1 (SEQ ID NO:3), ZIP2 (SEQ ID NO:5) and ZIP3 (SEQ ID NO:7).

Amino acid and nucleotide sequence identities between different MRT family members are outlined in Tables 1 and 2 below.

TABLE 2

Nucleotide Identity Values for MRT Family Members

|  | IRT1 | IRT2 | ZIP1 | ZIP2 | ZIP3 | ZRT1 | ZRT2 | ETI-1 |
|---|---|---|---|---|---|---|---|---|
| IRT1 | — | | | | | | | |
| IRT2 | 73.1 | — | | | | | | |
| ZIP1 | 51.7 | 50.7 | — | | | | | |
| ZIP2 | 41.4 | 41.0 | 41.9 | — | | | | |
| ZIP3 | 54.4 | 53.0 | 57.7 | 42.5 | — | | | |
| ZRT1 | 43.6 | 44.7 | 41.5 | 39.7 | 46.9 | — | | |
| ZRT2 | 44.4 | 45.3 | 44.5 | 40.2 | 43.9 | 44.6 | — | |
| ETI-1 | 40.1 | 40.5 | 43.8 | 41.2 | 40.0 | 42.0 | 40.6 | — |
| | | IDENTITY | | | | | | |

Accordingly, this invention pertains to MRT polypeptides and to active portions or fragments thereof, such as peptides having MRT bioactivity. The phrases "an activity of MRT" or "having an MRT bioactivity" are used interchangeably herein to refer to molecules such as proteins, polypeptides, and peptides which have one or more of the following functional characteristics:

(1) the MRT polypeptide has the ability to transport one or more of the following metals: Fe, e.g., Fe(II), Cd, Co, Mn, Pb, Hg and Zn;

(2) the MRT polypeptide has the ability to bind one or more of the following metals: Fe, e.g., Fe(II), Cd, Co, Mn, Pb, Hg and Zn;

(3) the MRT polypeptide has affinity for one or more of the following metals: Fe, e.g., Fe(II), Cd, Co, Mn, Pb, Hg and Zn;

(4) the MRT polypeptide has the ability to suppress the growth defect of a fet3 fet4 yeast strain;

(5) the MRT polypeptide has the ability to uptake one of the following metals: Fe, e.g., Fe(II), Cd, Co, Mn, Pb, Hg and Zn;

(6) the MRT polypeptide has the ability to modulate metal concentration in a biological sample; and (7) the MRT polypeptide has the ability to suppress the growth defect of a zrt1 zrt2 yeast strain.

Various aspects of the invention are described in further detail in the following subsections:

I. Isolated MRT Nucleic Acid Molecules

One aspect of this invention pertains to isolated nucleic acid molecules that encode a novel MRT polypeptide, such as an *A. thaliana* IRT1 polypeptide, an *A. thaliana* IRT2 polypeptide, an *A. thaliana* ZIP1 polypeptide, an *A. thaliana* ZIP2 polypeptide, an *A. thaliana* ZIP3 polypeptide, portions

TABLE 1

Amino Acid Similarities and Identities Among MRT Family Members

| | | | | | | | SIMILARITY | | |
|---|---|---|---|---|---|---|---|---|---|
| | IRT1 | IRT2 | ZIP1 | ZIP2 | ZIP3 | ZRT1 | ZRT2 | C.E.I RT1 | ETI-1 |
| IRT1 | — | 84.4 | 67.2 | 53.0 | 65.6 | 54.4 | 64.9 | 47.2 | 53.9 |
| IRT2 | 70.3 | — | 62.4 | 49.5 | 64.8 | 51.8 | 60.2 | 49.8 | 52.9 |
| ZIP1 | 43.5 | 41.7 | — | 51.2 | 69.9 | 57.6 | 61.5 | 47.9 | 55.9 |
| ZIP2 | 22.3 | 21.5 | 19.1 | — | 53.9 | 49.6 | 55.2 | 47.5 | 55.2 |
| ZIP3 | 47.7 | 44.3 | 49.1 | 23.9 | — | 55.9 | 60.6 | 45.9 | 53.9 |
| ZRT1 | 29.5 | 26.0 | 28.7 | 20.6 | 30.0 | — | 67.0 | 50.6 | 52.0 |
| ZRT2 | 34.5 | 35.2 | 32.6 | 23.2 | 37.7 | 43.8 | — | 52.2 | 55.9 |
| C.E.I RT1 | 20.8 | 20.8 | 19.8 | 23.2 | 21.8 | 20.0 | 20.3 | — | 51.0 |
| ETI-1 | 21.3 | 22.8 | 23.6 | 23.8 | 23.6 | 23.0 | 22.7 | 29.3 | — |
| | | | IDENTITY | | | | | | | or fragments of such nucleic acids, or equivalents thereof. The term "nucleic acid molecule" as used herein is intended to include such fragments or equivalents and refers to DNA molecules (e.g., cDNA or genomic DNA) and RNA molecules (e.g., mRNA). The nucleic acid molecule can be single-stranded or double-stranded, but preferably is double-stranded DNA. An "isolated" nucleic acid molecule is free of sequences which naturally flank the nucleic acid (i.e., sequences located at the 5' and 3' ends of the nucleic acid) in the genomic DNA of the organism from which the nucleic acid is derived. Moreover, an "isolated" nucleic acid molecule, such as a cDNA molecule, can be free of other cellular material.

The term "equivalent" is intended to include nucleotide sequences encoding a functionally equivalent MRT polypeptide or functionally equivalent polypeptide or peptides having an MRT bioactivity. Functionally equivalent MRT polypeptide or peptides include polypeptides which have one or more of the functional characteristics described herein.

Other equivalents of MRT polypeptides include structural equivalents. Structural equivalents of an MRT polypeptide preferably comprise at least one transmembrane domain which has at least about 40%, more preferably at least about 50%, 55%, 60%, 70%, 80% or 90% amino acid sequence identity with an amino acid sequence shown in SEQ ID NO:2, SEQ ID NO:4, SEQ ID NO:6, SEQ ID NO:8, or SEQ ID NO:14 and/or at least one histidine rich domain. Other preferred structural equivalents of MRT polypeptides include a transmembrane domain, a histidine rich domain, a variable loop domain and optionally one or more of the domains present in MRT polypeptides described herein. Preferred nucleic acid molecules of the invention comprise a nucleotide sequence shown in SEQ ID NO:1, SEQ ID NO:3, SEQ ID NO:5, SEQ ID NO:7, or SEQ ID NO:13, a complement, fragment, portion or equivalent thereof.

In one embodiment, the invention pertains to a nucleic acid molecule which is a naturally occurring form of a nucleic acid molecule encoding an MRT polypeptide, such as an MRT polypeptide having an amino acid sequence shown in SEQ ID NO:2, SEQ ID NO:4, SEQ ID NO:6, SEQ ID NO:8, or SEQ ID NO:14. A naturally occurring form of a nucleic acid encoding MRT is derived from a mammal, e.g., a human, yeast, nematodes or plants, e.g., strategy I or a strategy II plants, e.g., *Arabidopsis thaliana*, rice, broccoli, tomato and mustard. Such naturally occurring equivalents can be obtained, for example, by screening a cDNA library, prepared with RNA from a mammal, with a nucleic acid molecule having a sequence shown in SEQ ID NO:1, SEQ ID NO:3, SEQ ID NO:5, SEQ ID NO:7, or SEQ ID NO:13 under high stringency hybridization conditions. Such conditions are further described herein.

Also within the scope of the invention are nucleic acids encoding natural variants and isoforms of MRT polypeptides, such as splice forms. Such natural variants are also within the scope of the invention.

In a preferred embodiment, the nucleic acid molecule encoding an MRT polypeptide is a cDNA. Preferably, the nucleic acid molecule is a cDNA molecule consisting of at least a portion of a nucleotide sequence encoding a polypeptide as shown in SEQ ID NO:2, SEQ ID NO:4, SEQ ID NO:6, SEQ ID NO:8, or SEQ ID NO:14. Preferred nucleic acid molecules encode polypeptides that have at least about 40%, preferably at least about 42%, 45%, 47%, 50%, more preferably at least about 52%, and most preferably at least about 55%, 60%, 70%, 80%, 90%, 95%, 97%, 98% or more amino acid sequence identity over the entire sequence with the amino acid sequence shown in SEQ ID NO:2, SEQ ID NO:4, SEQ ID NO:6, SEQ ID NO:8, or SEQ ID NO:14. A preferred portion of the cDNA molecule of SEQ ID NO:1 includes the coding region of the molecule (i.e., nucleotides 18–1034). Other preferred portions include those which code for domains of MRT, such as the transmembrane domains,e.g., the eight transmembrane domains of IRT1, the histidine rich domains, e.g., the four histidine rich domains of IRT1, or any combination thereof.

In another embodiment, the nucleic acid of the invention encodes an MRT polypeptide or an active portion or fragment thereof having an amino acid sequence shown in SEQ ID NO:2, SEQ ID NO:4, SEQ ID NO:6, SEQ ID NO:8, or SEQ ID NO:14. In yet another embodiment, preferred nucleic acid molecules encode a polypeptide having an amino acid sequence identity of at least about 40%, preferably at least about 42%, 45%, 47%, 50%, more preferably at least about 52%, and most preferably at least about 55%, 60%, 70%, 80%, 90%, 95%, 97%, 98% or more over the entire sequence with an amino acid sequence shown in SEQ ID NO:2, SEQ ID NO:4, SEQ ID NO:6, SEQ ID NO:8, or SEQ ID NO:14. Nucleic acid molecules which encode peptides having an amino acid sequence identity of at least about 93%, more preferably at least about 95%, and most preferably at least about 98–99% over the entire sequence with a sequence set forth in SEQ ID NO:2, SEQ ID NO:4, SEQ ID NO:6, SEQ ID NO:8, or SEQ ID NO:14 are also within the scope of the invention. Homology, used interchangeably herein with the term "identity" refers to sequence similarity between two protein (peptides) or between two nucleic acid molecules. Homology or identity can be determined by comparing a position in each sequence which may be aligned for purposes of comparison. When a position in the compared sequences is occupied by the same nucleotide base or amino acid, then the molecules are homologous, or identical, at that position. A degree (or percentage) of homology between sequences is a function of the number of matching or homologous positions shared by the sequences.

Isolated nucleic acids encoding a peptide having an MRT bioactivity, as described herein, and having a sequence which differs from a nucleotide sequence shown in SEQ ID NO:1, SEQ ID NO:3, SEQ ID NO:5, SEQ ID NO:7, or SEQ ID NO:13 due to degeneracy in the genetic code are also within the scope of the invention. Such nucleic acids encode functionally equivalent peptides (e.g., having an MRT bioactivity) or structurally equivalent polypeptides but differ in sequence from the sequence of SEQ ID NO:2, SEQ ID NO:4, SEQ ID NO:6, SEQ ID NO:8, or SEQ ID NO:14 due to degeneracy in the genetic code. For example, a number of amino acids are designated by more than one triplet. Codons that specify the same amino acid, or synonyms (for example, CAU and CAC are synonyms for histidine) may occur due to degeneracy in the genetic code. As one example, DNA sequence polymorphisms within the nucleotide sequence of an MRT polypeptide (especially those within the third base of a codon) may result in "silent" mutations in the DNA which do not affect the amino acid encoded. However, it is expected that DNA sequence polymorphisms that do lead to changes in the amino acid sequences bf the MRT polypeptide will exist within a population. It will be appreciated by one skilled in the art that these variations in one or more nucleotides (up to about 3–4% of the nucleotides) of the nucleic acids encoding peptides having the activity of an MRT polypeptide may exist among different plant species or individuals within a population due to natural allelic variation. Any and all such nucleotide variations and resulting amino acid polymorphisms are within the scope of the invention. Furthermore, there are likely to be isoforms or family members of the MRT polypeptide family in addition to those described herein. Such isoforms or family members are defined as proteins related in function and amino acid sequence to an MRT polypeptide, but encoded by genes at different loci. Such isoforms or family members are within the scope of the invention. Additional members of the MRT polypeptide family can be isolated by, for example, screening a library of interest under low stringency conditions described herein or by screening or amplifying with degenerate probes derived from highly conserved amino acids sequences, for example, from the amino acid sequence in SEQ ID NO:2, SEQ ID NO:4, SEQ ID NO:6, SEQ ID NO:8, or SEQ ID NO:14. Alternatively, other members of the MRT polypeptide family can be isolated using one or more of the following techniques. For example, a genomic library from several other dicots, e.g., tomato, broccoli or mustard, can be screened to obtain genes of the MRT family. Positive clones are then analyzed and sequenced to obtain additional family members.

A "fragment" or "portion" of a nucleic acid encoding an MRT polypeptide is defined as a nucleotide sequence having fewer nucleotides than the nucleotide sequence encoding the entire amino acid sequence of an MRT polypeptide, such as an *A. thaliana* IRT1, an *A. thaliana* IRT2, an *A. thaliana* ZIP1, an *A. thaliana* ZIP2, or an *A. thaliana* ZIP3. A fragment or portion of a nucleic acid molecule is at least about 20 nucleotides, preferably at least about 30 nucleotides, more preferably at least about 40 nucleotides, even more preferably at least about 50 nucleotides in length. Also within the scope of the invention are nucleic acid fragments which are t least about 60, 70, 80, 90, 100 or more nucleotides in length. Preferred fragments or portions include fragments which encode a polypeptide having an MRT bioactivity as described herein. To identify fragments of portions of the nucleic acids encoding fragments or portions of polypeptides which have an MRT bioactivity, several different assays can be employed. For example, to determine the metal uptake activity of MRT peptides, commonly practiced metal uptake activity studies, for example, those described in the Examples section herein can be performed to obtain MRT peptides which transport, for example, Fe, e.g., Fe(II), Cd, Co, Mn, Pb, Hg and/or Zn.

Another aspect of the invention provides a nucleic acid which hybridizes under high or low stringency conditions to a nucleic acid which encodes a peptide having all or a portion of an amino acid sequence shown in SEQ ID NO:2, SEQ ID NO:4, SEQ ID NO:6, SEQ ID NO:8, or SEQ ID NO:14. Appropriate stringency conditions which promote DNA hybridization, for example, 6.0×sodium chloride/sodium citrate (SSC) at about 45° C., followed by a wash of 2.0×SSC at 50° C. are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 25° C. to a high stringency of about 0.2×SSC at 65° C. In addition, the temperature in the wash step can be increased from low stringency conditions at room temperature, about 22° C., to high stringency conditions, at about 65° C. Preferably, an isolated nucleic acid molecule of the invention that hybridizes under stringent conditions to the sequence of SEQ ID NO:1, SEQ ID NO:3, SEQ ID NO:5, SEQ ID NO:7, or SEQ ID NO:13 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural MRT polypeptide.

In addition to naturally-occurring allelic variants of the MRT sequence that can exist in the population, the skilled artisan will further appreciate that changes can be introduced by mutation into the nucleotide sequence of SEQ ID NO:1, SEQ ID NO:3, SEQ ID NO:5, SEQ ID NO:7, or SEQ ID NO:13 thereby leading to changes in the amino acid sequence of the encoded MRT polypeptide, without altering the functional ability of the MRT polypeptide. For example, nucleotide substitutions leading to amino acid substitutions at "non-essential" amino acid residues can be made in the sequence of SEQ ID NO:1, SEQ ID NO:3, SEQ ID NO:5, SEQ ID NO:7, or SEQ ID NO:13. A "non-essential" amino acid residue is a residue that can be altered from the wild-type sequence of MRT (e.g., the sequence of SEQ ID NO:2, SEQ ID NO:4, SEQ ID NO:6, SEQ ID NO:8, or SEQ ID NO:14) without altering the MRT activity of the polypeptide.

An isolated nucleic acid molecule encoding an MRT polypeptide homologous to the protein of SEQ ID NO:2, SEQ ID NO:4, SEQ ID NO:6, SEQ ID NO:8, or SEQ ID NO:14 can be created by introducing one or more nucleotide substitutions, additions or deletions into the nucleotide sequence of SEQ ID NO:1, SEQ ID NO:3, SEQ ID NO:5, SEQ ID NO:7, or SEQ ID NO:13 such that one or more amino acid substitutions, additions or deletions are introduced into the encoded polypeptide. Mutations can be introduced into SEQ ID NO:1, SEQ ID NO:3, SEQ ID NO:5, SEQ ID NO:7, or SEQ ID NO:13 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in MRT is preferably replaced with another amino acid residue from the same side chain family. Alternatively, in another embodiment, mutations can be introduced randomly along all or part of an MRT coding sequence, such as by saturation mutagenesis, and the resultant mutants can be screened for proteolytic activity to identify mutants that retain proteolytic activity. Following mutagenesis of the nucleotide sequence of SEQ ID NO:1, SEQ ID NO:3, SEQ ID NO:5, SEQ ID NO:7, or SEQ ID NO:13, the encoded polypeptide can be expressed recombinantly and activity of the protein can be determined.

In addition to the nucleic acid molecules encoding MRT polypeptides described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire MRT coding strand, or to only a portion thereof. In one embodiment, an antisense nucleic acid molecule is antisense to a "coding region" of the coding strand of a nucleotide sequence encoding MRT. The term "coding region" refers to the region of the nucleotide sequence comprising codons which are translated into amino acid residues (e.g., the entire coding region of SEQ ID NO:1, SEQ ID NO:3, SEQ ID NO:5, SEQ ID NO:7, or SEQ ID NO:13). In another embodiment, the antisense nucleic acid molecule is antisense to a "noncoding region" of the coding strand of a nucleotide sequence encoding MRT. The term "noncoding region" refers to 5' and 3' sequences which flank the coding region that are not translated into amino acids (i.e., also referred to as 5' and 3' untranslated regions).

Given the coding strand sequences encoding MRT polypeptides disclosed herein (e.g., SEQ ID NO:1, SEQ ID NO:3, SEQ ID NO:5, SEQ ID NO:7, or SEQ ID NO:13), antisense nucleic acids of the invention can be designed according to the rules of Watson and Crick base pairing. The antisense nucleic acid molecule can be complementary to the entire coding region of MRT mRNA, but more preferably is an oligonucleotide which is antisense to only a portion of the coding or noncoding region of MRT mRNA. For example, the antisense oligonucleotide can be complementary to the region surrounding the translation start site of MRT mRNA. An antisense oligonucleotide can be, for example, about 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. A ribozyme having specificity for an MRT-encoding nucleic acid can be designed based upon the nucleotide sequence of an MRT cDNA disclosed herein (i.e., SEQ ID NO:1, SEQ ID NO:3, SEQ ID NO:5, SEQ ID NO:7, or SEQ ID NO:13). See, e.g., Cech et al. U.S. Pat. No. 4,987,071; and Cech et al. U.S. Pat. No. 5,116,742. Alternatively, MRT mRNA can be used to select a catalytic RNA having a specific ribonuclease activity from a pool of RNA molecules. See, e.g., Bartel, D. and Szostak, J. W. (1993) *Science* 261: 1411–1418.

The nucleic acid molecules of the invention can also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,171,071, incorporated by reference herein).

II. Recombinant Expression Vectors and Host Cells

Another aspect of the invention pertains to vectors, preferably expression vectors, containing a nucleic acid encoding MRT (or a portion or fragment thereof). As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector may depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., MRT polypeptides, mutant forms of MRT, fusion proteins, etc.).

The recombinant expression vectors of the invention can be designed for expression of MRT in prokaryotic or eukaryotic cells. For example, MRT can be expressed in bacterial cells such as *E. coli*, insect cells (using baculovirus expression vectors) yeast cells, plant cells or mammalian cells. Suitable host cells are discussed further in Goeddel, *Gene Expression Technology: Methods in Enzymology* 185, Academic Press, San Diego, Calif. (1990). Alternatively, the recombinant expression vector may be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al. (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21 (DE3) or HMS 174(DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al. (1992) *Nuc. Acids Res.* 20:2111–2118). Such alteration of nucleic acid sequences of the invention can be carried out by standard DNA synthesis techniques.

In another embodiment, the MRT expression vector is a yeast expression vector. Examples of vectors for expression in yeast *S. cerivisae* include pYepSec1 (Baldari. et al. (1987) *Embo J.* 6:229–234), pMFa (Kuidan and Herskowitz (1982) *Cell* 30:933–943), pJRY88 (Schultz et al. (1987) *Gene* 54:113–123), and pYES2 (Invitrogen Corporation, San Diego, Calif.).

Alternatively, MRT can be expressed in insect cells using baculovirus expression vectors. Baculovirus vectors available for expression of proteins in cultured insect cells (e.g., Sf9 cells) include the pAc series (Smith et al. (1983) *Mol. Cell Biol.* 3:2156–2165) and the pVL series (Lucklow, V. A., and Summers, M. D. (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987), *EMBO J.* 6:187–195). When used in mammalian cells, the expression vector's control functions are often provided by viral regulatory elements. For example, commonly used promoters are derived from polyoma, adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Baneiji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), cauliflower mosaic virus promoter, e.g., CaMV35S, and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–3 79) and the α-fetoprotein promoter (Campes and Tilghman (1989) *Genes Dev.* 3:537–546).

In one embodiment, a recombinant expression vector containing DNA encoding a MRT fusion protein is produced. An MRT fusion protein can be produced by recombinant expression of a nucleotide sequence encoding a first polypeptide peptide having an MRT bioactivity and a nucleotide sequence encoding a second polypeptide having an amino acid sequence unrelated to an amino acid sequence which has at least about 40% or more amino acid sequence identity with an amino acid sequence shown in SEQ ID NO:2, SEQ ID NO:4, SEQ ID NO:6, SEQ ID NO:8, or SEQ ID NO:14. In many instances, the second polypeptide correspond to a moiety that alters a characteristic of the first peptide, e.g., its solubility, affinity, stability or valency. For example, an MRT polypeptide of the present invention can be generated as a glutathione-S-transferase (GST—fusion protein). Such GST fusion proteins can enable easy purification of the MRT polypeptide, such as by the use of glutathione-derivatized matrices (see, for example, *Current Protocols in Molecular Biology*, eds. Ausabel et al. (N.Y.: John Wiley & Sons, 1991)). Preferably the fusion proteins of the invention are functional in a two hybrid assay. Fusion proteins and peptides produced by recombinant techniques can be secreted and isolated from a mixture of cells and medium containing the protein or peptide. Alternatively, the protein or peptide can be retained cytoplasmically and the cells harvested, lysed and the protein isolated. A cell culture typically includes host cells, media and other byproducts. Suitable media for cell culture are well known in the art. Protein and peptides can be isolated from cell culture medium, host cells, or both using techniques known in the art for purifying proteins and peptides. Techniques for transfecting host cells and purifying proteins and peptides are described in further detail herein.

The invention further provides a recombinant expression vector comprising a DNA molecule of the invention cloned into the expression vector in an antisense orientation. That is, the DNA molecule is operatively linked to a regulatory sequence in a manner which allows in for expression (by transcription of the DNA molecule) of an RNA molecule which is antisense to MRT RNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to recombinant host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an MRT polypeptide can be expressed in bacterial cells such as *E. coli*, insect cells, yeast, plant or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (*Molecular Cloning: A Laboratory Manual*, 2nd Edition, Cold Spring Harbor Laboratory press (1989)), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker may be introduced into a host cell on the same vector as that encoding MRT or may be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) an MRT polypeptide. Accordingly, the invention further provides methods for producing MRT polypeptides using the host cells of the invention. In one embodiment, the method comprises culturing the host cell of invention (into which a recombinant expression vector encoding MRT has been introduced) in a suitable medium until MRT is produced. In another embodiment, the method further comprises isolating MRT from the medium or the host cell.

The host cells of the invention can also be used to produce transgenic plants. As used herein, the term "transgenic" refers to a cell, group of cells, or organism, e.g., plant or animal, which includes a DNA sequence which is inserted by artifice therein. If the DNA sequence is inserted into a cell, the sequence becomes part of the genome of the organism which develops from that cell. For example, the transgenic organisms are generally transgenic plants and the DNA transgene is inserted artificially into the nuclear or plastidic genome. As used herein, the term "transgene" refers to any piece of DNA which is artificially inserted into a cell, group of cells, or organism, e.g., plant or animal, and becomes a part of the genome of the organism which develops from that cell. Such a transgene can include a gene which is partly or entirely heterologous to the transgenic organism, or can include a gene homologous to an endogenous gene of the organism.

For example, in one embodiment, a host cell of the invention is a plant cell, e.g., a protoplast, into which MRT-coding sequences have been introduced. As used herein, a "plant cell" refers to any self-propagating cell bounded by a semi-permiable membrane and containing a plastid. Such a cell requires a cell wall if further propagation is desired. For example, plant cells of the invention include algae, cyanobacteria, seed suspension cultures, embryos, meristematic regions, callus tissue, leaves, roots, shoots, gametophytes, sporophytes, pollen, and microspores. As used herein, the term "plant" refers to either a whole plant, a plant part, a plant cell, or a group of plant cells. The class of plants which can be used in the method of the invention is generally as broad as the class of higher plants amenable to transformation techniques, including both monocotyledonous and dicotyledonous plants. It includes plants of a variety of ploidy levels, including polyploid, diploid and haploid.

The transformation of plants in accordance with the invention can be carried out in essentially any of the various ways known to those skilled in the art of plant molecular biology. See, in general, *Methods in Enzymology* Vol. 153 ("Recombinant DNA Part D") 1987, Wu and Grossman Eds., Academic Press and European Pat. Application EP 693554.

Selection of an appropriate vector is relatively simple, as the constraints are minimal. The minimal traits of the vector are that the desired nucleic acid sequence be introduced in a relatively intact state. Thus any vector which produces a plant carrying the introduced DNA sequence is sufficient. Also, any vector which introduces a substantially intact RNA which can ultimately be converted into a stably maintained DNA sequence can be used to transform a plant cell.

Even a naked piece of DNA confers the properties of this invention, though at low efficiency. The decision as to whether to use a vector, or which vector to use, is determined by the method of transformation selected.

If naked nucleic acid introduction methods are chosen, then the vector need be no more than the minimal nucleic acid sequences necessary to confer the desired traits, without the need for additional other sequences. Thus, the possible vectors include the Ti plasmid vectors, shuttle vectors designed merely to maximally yield high numbers of copies, episomal vectors containing minimal sequences necessary for ultimate replication once transformation has occurred, transposon vectors, homologous recombination vectors, mini-chromosome vectors, and viral vectors, including the possibility of RNA forms of the gene sequences. The selection of vectors and methods to construct them are commonly known to persons of ordinary skill in the art and are described in general technical references (*Methods in Enzymology* Vol. 153 ("Recombinant DNA Part D") 1987, Wu and Grossman Eds., Academic Press).

In one embodiment, the foreign nucleic acid is mechanically transferred by microinjection directly into plant cells by use of micropipettes. Alternatively, the foreign nucleic acid can be transferred into the plant cell by using polyethylene glycol. This forms a precipitation complex with the genetic material that is taken up by the cell (Paszkowski et al. (1984) *EMBO J.* 3:2712–22).

In another embodiment, foreign nucleic acid can be introduced into the plant cells by electroporation (Fromm et al. (1985) *Proc. Natl. Acad. Sci. USA* 82:5824). In this technique, plant protoplasts are electroporated in the presence of plasmids or nucleic acids containing the relevant genetic construct. Electrical impulses of high field strength reversibly permeabilize biomembranes allowing the introduction of the plasmids. Electroporated plant protoplasts reform the cell wall, divide, and form a plant callus. Selection of the transformed plant cells with the transformed gene can be accomplished using phenotypic markers.

Cauliflower mosaic virus (CaMV) can also be used as a vector for introducing the foreign nucleic acid into plant cells (Hohn et al. (1982) "Molecular Biology of Plant Tumors," Academic Press, New York, pp. 549–560; Howell, U.S. Pat. No. 4,407,956). CaMV viral DNA genome is inserted into a parent bacterial plasmid creating a recombinant DNA molecule which can be propagated in bacteria. After cloning, the recombinant plasmid again can be cloned and further modified by introduction of the desired DNA sequence into the unique restriction site of the linker. The modified viral portion of the recombinant plasmid is then excised from the parent bacterial plasmid, and used to inoculate the plant cells or plants.

Another method of introduction of foreign nucleic acid into plant cells is high velocity ballistic penetration by small particles with the nucleic acid either within the matrix of small beads or particles, or on the surface (Klein et al. (1987) *Nature* 327:70–73). Although typically only a single introduction of a new nucleic acid segment is required, this method particularly provides for multiple introductions.

A preferred method of introducing the nucleic acids into plant cells is to infect a plant cell, an explant, a meristem or a seed with *Agrobacterium tumefaciens* transformed with the nucleic acid. Under appropriate conditions known in the art, the transformed plant cells are grown to form shoots, roots, and develop further into plants. The nucleic acids can be introduced into appropriate plant cells, for example, by means of the Ti plasmid of *Agrobacterium tumefaciens*. The Ti plasmid is transmitted to plant cells upon infection by *Agrobacterium tumefaciens*, and is stably integrated into the plant genome (Horsch et al. (1984) "Inheritance of Functional Foreign Genes in Plants," *Science* 231:496–498; Fraley et al. (1983) *Proc. Natl. Acad. Sci. USA* 80:4803).

Ti plasmids contain two regions essential for the production of transformed cells. One of these, named transfer DNA (T DNA), induces tumor formation. The other, termed virulent region, is essential for the introduction of the T DNA into plants. The transfer DNA region, which transfers to the plant genome, can be increased in size by the insertion of the foreign nucleic acid sequence without affecting its transferring ability. By removing the tumor-causing genes so that they no longer interfere, the modified Ti plasmid can then be used as a vector for the transfer of the gene constructs of the invention into an appropriate plant cell.

There are presently at least three different ways to transform plant cells with Agrobacterium: (1) co-cultivation of Agrobacterium with cultured isolated protoplasts; (2) transformation of cells or tissues with Agrobacterium; or (3) transformation of seeds, apices or meristems with Agrobacterium. The first method requires an established culture system that allows culturing protoplasts and plant regeneration from cultured protoplasts. The second method requires that the plant cells or tissues can be transformed by Agrobacterium and that the transformed cells or tissues can be induced to regenerate into whole plants. The third method requires micropropagation.

In the binary system, to have infection, two plasmids are needed: a T-DNA containing plasmid and a vir plasmid. Any one of a number of T-DNA containing plasmids can be used, the only requirement is that one be able to select independently for each of the two plasmids.

After transformation of the plant cell or plant, those plant cells or plants transformed by the Ti plasmid so that the desired DNA segment is integrated can be selected by an appropriate phenotypic marker. These phenotypic markers include, but are not limited to, antibiotic resistance, herbicide resistance or visual observation. Other phenotypic markers are known in the art and can be used in this invention.

All plants from which protoplasts can be isolated and cultured to give whole regenerated plants can be transformed by the present invention so that whole plants are recovered which contain the transferred foreign gene. Some suitable plants include, for example, species from the genera Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Hyoseyamus, Lycopersicon, Nicotiana, golanum, Petunia, Digitalis, Majorana, Ciohorium, Helianthus, Lactuca, Bromus, Asparagus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum, and Datura.

Practically all plants can be regenerated from cultured cells or tissues. The term "regeneration" as used herein, means growing a whole plant from a plant cell, a group of plant cells, a plant part or a plant piece (e.g. from a protoplast, callus, or tissue part) (*Methods in Enzymology* Vol. 153 ("Recombinant DNA Part D") 1987, Wu and Grossman Eds., Academic Press; also *Methods in Enzymology*, Vol. 118; and Klee et al., (1987) *Annual Review of Plant Physiology*, 38:467–486).

Plant regeneration from cultural protoplasts is described in Evans et al., "Protoplasts Isolation and Culture," *Handbook of Plant Cell Cultures* 1:124–176 (MacMillan Publishing Co. New York 1983); M. R. Davey, "Recent Developments in the Culture and Regeneration of Plant Protoplasts," *Protoplasts* (1983)-Lecture Proceedings, pp. 12–29, (Birkhauser, Basal 1983); P. J. Dale, "Protoplast Culture and Plant Regeneration of Cereals and Other Recalcitrant Crops," *Protoplasts* (1983)-Lecture Proceedings, pp. 3141, (Birkhauser, Basel 1983); and H. Binding, "Regeneration of Plants," *Plant Protoplasts*, pp. 21–73, (CRC Press, Boca Raton 1985).

Regeneration from protoplasts varies from species to species of plants, but generally a suspension of transformed protoplasts containing copies of the exogenous sequence is first generated. In certain species, embryo formation can then be induced from the protoplast suspension, to the stage of ripening and germination as natural embryos. The culture media can contain various amino acids and hormones, such as auxin and cytokinins. It can also be advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

In vegetatively propagated crops, the mature transgenic plants are propagated by the taking of cuttings or by tissue culture techniques to produce multiple identical plants for trialling, such as testing for production characteristics. Selection of a desirable transgenic plant is made and new varieties are obtained thereby, and propagated vegetatively for commercial sale. In seed propagated crops, the mature transgenic plants are self crossed to produce a homozygous inbred plant. The inbred plant produces seed containing the gene for the newly introduced foreign gene activity level. These seeds can be grown to produce plants that have the selected phenotype. The inbreds according to this invention can be used to develop new hybrids. In this method a selected inbred line is crossed with another inbred line to produce the hybrid.

Parts obtained from the regenerated plant, such as flowers, seeds, leaves, branches, fruit, and the like are covered by the invention, provided that these parts comprise cells which have been so transformed. Progeny and variants, and mutants of the regenerated plants are also included within the scope of this invention, provided that these parts comprise the introduced DNA sequences. Progeny and variants, and mutants of the regenerated plants are also included within the scope of this invention.

However, any additional attached vector sequences which confers resistance to degradation of the nucleic acid fragment to be introduced, which assists in the process of genomic integration or provides a means to easily select for those cells or plants which are transformed are dvantageous and greatly decrease the difficulty of selecting useable transgenic plants or plant cells.

Selection of transgenic plants or plant cells is typically be based upon a visual assay, such as observing color changes (e.g., a white flower, variable pigment production, and uniform color pattern on flowers or irregular patterns), but can also involve biochemical assays of either enzyme activity or product quantitation. Transgenic plants or plant cells are grown into plants bearing the plant part of interest and the gene activities are monitored, such as by visual appearance (for flavonoid genes) or biochemical assays (Northern blots); Western blots; enzyme assays and flavonoid compound assays, including spectroscopy, see, Harborne et al. (Eds.), (1975) *The Flavonoids*, Vols. 1 and 2, [Acad. Press]). Appropriate plants are selected and further evaluated. Methods for generation of genetically engineered plants are further described in U.S. Pat. No. 5,283,184, U.S. Pat. No. 5,482,852, and European Patent Application EP 693 554.

An example of a commercial application of the transgenic plants of the invention is in agriculture. Iron is an essential nutrient for crop plants because it is required for the activity of iron-containing proteins involved in photosynthesis and respiration. Although iron is abundant in the soil, its acquisition can be difficult under aerobic conditions because it is very insoluble at moderate pH. This issue is important in agriculture because a third of the world's soils are iron-deficient. Therefore, understanding how plants accumulate iron is critical for increased production of crops that would themselves be richer sources of iron in foods. The ability to develop transgenic plants, through manipulation of IRT1 gene and other members of the MRT family, that are more efficient in extracting iron from soil has important agricultural implications.

A second example of a commercial application of the transgenic plants of the invention is in environmental pollution remediation. Removal of toxic metals from contaminated sites is particularly difficult. Unlike organic pollutants, metal pollutants cannot be biodegraded. The current method of removing metals from contaminated sites is excavation, removal of the soil, and burial in a hazardous waste site. Phytoremediation, the technique of using plants to extract metals from soil, is a more economical and environmentally-safe alternative. Genetically engineered plants of the present invention that are created to be metal specific present great potential for this technology. IRT1 or other members of the MRT family can be manipulated in a plant species to allow high-level accumulation of a specific toxic metal from a contaminated soil.

III. Isolated MRT Polypeptides and Anti-MRT Antibodies

Another aspect of the invention pertains to isolated MRT polypeptides and active fragments or portions thereof, i.e., peptides having an MRT activity, such as *A. thaliana* IRT1, *A. thaliana* IRT2, *A. thaliana* ZIP1, *A. thaliana* ZIP2 or *A. thaliana* ZIP3. This invention also provides a preparation of MRT or fragment or portion thereof. An "isolated" polypeptide is substantially free of cellular material or culture medium when produced by recombinant DNA techniques, or chemical precursors or other chemicals when chemically synthesized. In a preferred embodiment, the MRT polypeptide has an amino acid sequence shown in SEQ ID NO:2, SEQ ID NO:4, SEQ ID NO:6, SEQ ID NO:8 or SEQ ID NO:14. In other embodiments, the MRT polypeptide is substantially homologous or identical to SEQ ID NO:2, SEQ ID NO:4, SEQ ID NO:6, SEQ ID NO:8 or SEQ ID NO:14 and retains the functional activity of the polypeptide of SEQ ID NO:2, SEQ ID NO:4, SEQ ID NO:6, SEQ ID NO:8 or SEQ ID NO:14 yet differs in amino acid sequence due to natural allelic variation or mutagenesis, as described in detail in subsection I above. Accordingly, in another embodiment, the MRT polypeptide is a polypeptide which comprises an amino acid sequence with at least about 40% overall amino acid identity with the amino acid sequence of SEQ ID NO:2, SEQ ID NO:4, SEQ ID NO:6, SEQ ID NO:8 or SEQ ID NO:14. Preferably, the polypeptide is at least about 40%, preferably at least about 42%, 45%, 47%, 50%, more preferably at least about 52%, and most preferably at least about 55%, 60%, 70%, 80%, 90%, 95%, 97% or 98%-99% identical over the entire sequence to SEQ ID NO:2, SEQ ID NO:4, SEQ ID NO:6, SEQ ID NO:8 or SEQ ID NO:14.

An isolated MRT polypeptide can comprise the entire amino acid sequence of SEQ ID NO:2, SEQ ID NO:4, SEQ ID NO:6, SEQ ID NO:8 or SEQ ID NO:14, or a biologically active portion or fragment thereof. For example, an active portion of MRT can comprise a selected domain of MRT, such as the transmembrane domain or the histidine rich domain. Moreover, other biologically active portions, in which other regions of the protein are deleted, can be prepared by recombinant techniques and evaluated for an MRT bioactivity as described in detail herein. For example, a peptide having an MRT bioactivity can differ in amino acid sequence from the sequence depicted in SEQ ID NO:2, SEQ ID NO:4, SEQ ID NO:6, SEQ ID NO:8 or SEQ ID NO:14 but such differences result in a peptide which functions in the same or similar manner as MRT. Thus, peptides having the ability to modulate metal transport, e.g., Fe, e.g., Fe(II), Co, Cd, Mn, Pb, Hg and/or Zn transport, and which preferably have at least one transmebrane domain and/or at least one histidine rich domain are within the scope of this invention. Preferred peptides of the invention include those which are further capable of reducing Fe(III) to the more soluble Fe(II) form.

A peptide can be produced by modification of the amino acid sequence shown in SEQ ID NO:2, SEQ ID NO:4, SEQ ID NO:6, SEQ ID NO:8 or SEQ ID NO:14 such as a substitution, addition or deletion of an amino acid residue which is not directly involved in the function of MRT. For example, in order to enhance stability and/or reactivity, the polypeptides or peptides of the invention can also be modified to incorporate one or more polymorphisms in the amino acid sequence of the protein allergen resulting from natural allelic variation. Additionally, D-amino acids, non-natural amino acids or non-amino acid analogues can be substituted or added to produce a modified protein or peptide within the scope of this invention. Modifications of proteins or peptides or portions thereof can also include reduction/alkylation (Tarr in: *Methods of protein Microcharacterization*, J. E. Silver ed. Humana Press, Clifton, N.J., pp 155–194 (1986)); acylation (Tarr, supra); chemical coupling to an appropriate carrier (Mishell and Shiigi, eds, *Selected Methods in Cellular Immunology*, WH Freeman, San Francisco, Calif. (1980); U.S. Pat. No. 4,939,239; or mild-formalin treatment (Marsh *International Archives of Allergy and Applied Immunology*, 41:199–215 (1971)).

To facilitate purification and potentially increase solubility of proteins or peptides of the invention, reporter group(s) can be added to the peptide backbone. For example, polyhistidine can be added to a peptide to purify the peptide on immobilized metal ion affinity chromatography (Hochuli, E. et al. (1988) *Bio/Technology*, 6:1321–1325). In addition, specific endoprotease cleavage sites can be introduced, if desired, between a reporter group and amino acid sequences of a peptide to facilitate isolation of peptides free of irrelevant sequences.

Peptides of the invention are typically at least amino acid residues in length, preferably at least 40 amino acid residues in length, more preferably at least 50 amino acid residues in length, and most preferably 60 amino acid residues in length. Peptides having MRT activity and including at least 80 amino acid residues in length, at least 100 amino acid residues in length, at least about 200, or at least about 300 or more amino acid residues in length are also within the scope of the invention. Other peptides within the scope of the invention include those encoded by the nucleic acids described herein.

Another embodiment of the invention provides a substantially pure preparation of a peptide having an MRT bioactivity. Such a preparation is substantially free of proteins and peptides with which the peptide naturally occurs in a cell or with which it naturally occurs when secreted by a cell.

The term "isolated" when used to refer to an MRT polypeptide means that the polypeptide is substantially free of cellular material or culture medium when produced by recombinant DNA techniques, or chemical precursors or other chemicals when chemically synthesized.

The peptides and fusion proteins produced from the nucleic acid molecules of the present invention can also be used to produce antibodies specifically reactive with MRT polypeptides. For example, by using a full-length MRT polypeptide, such as an antigen having an amino acid sequence shown in SEQ ID NO:2, SEQ ID NO:4, SEQ ID NO:6, SEQ ID NO:8 or SEQ ID NO:14, or a peptide fragment thereof, anti-protein/anti-peptide polyclonal antisera or monoclonal antibodies can be made using standard methods. A mammal, (e.g., a mouse, hamster, or rabbit) can be immunized with an immunogenic form of the protein or peptide which elicits an antibody response in the mammal. The immunogen can be, for example, a recombinant MRT polypeptide, or fragment or portion thereof or a synthetic peptide fragment. The immunogen can be modified to increase its immunogenicity. For example, techniques for conferring immunogenicity on a peptide include conjugation to carriers or other techniques well known in the art For example, the peptide can be administered in the presence of adjuvant. The progress of immunization can be monitored by detection of antibody titers in plasma or serum. Standard ELISA or other immunoassay can be used with the immunogen as antigen to assess the levels of antibodies.

Following immunization, antisera can be obtained and, if desired, polyclonal antibodies isolated from the sera. To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art. For example, the hybridoma technique originally developed by Kohler and Milstein (*Nature* (1975) 256:495–497) as well as other techniques such as the human B-cell hybridoma technique (Kozbar et al., *Immunol. Today* (1983) 4:72), the EBV-hybridoma technique to produce human monoclonal antibodies (Cole et al. *Monoclonal Antibodies in Cancer Therapy* (1985) Allen R. Bliss, Inc., pages 77–96), and screening of combinatorial antibody libraries (Huse et al., *Science* (1989) 246:1275). Hybridoma cells can be screened immunochemically for production of antibodies specifically reactive with the peptide and monoclonal antibodies isolated.

The term "antibody" as used herein is intended to include fragments thereof which are also specifically reactive with a peptide having an MRT activity as described herein. Antibodies can be fragmented using conventional techniques and the fragments screened for utility in the same manner as described above for whole antibodies. For example, $F(ab')_2$ fragments can be generated by treating antibody with pepsin. The resulting $F(ab')_2$ fragment can be treated to reduce disulfide bridges to produce Fab' fragments. The antibody of the present invention is further intended to include bispecific and chimeric molecules having an anti-MRT polypeptide portion.

When antibodies produced in non-human subjects are used therapeutically in humans, they are recognized to varying degrees as foreign and an immune response may be generated in the patient. One approach for minimizing or eliminating this problem, which is preferable to general immunosuppression, is to produce chimeric antibody derivatives, i.e., antibody molecules that combine a non-human animal variable region and a human constant region. Chimeric antibody molecules can include, for example, the antigen binding domain from an antibody of a mouse, rat, or other species, with human constant regions. A variety of approaches for making chimeric antibodies have been described and can be used to make chimeric antibodies containing the immunoglobulin variable region which recognizes the gene product of the novel MRT polypeptides of the invention. See, e.g., Morrison et al. (1985) *Proc. Natl. Acad. Sci. U.S.A.* 81:6851; Takeda et al. (1985) *Nature* 314:452; Cabilly et al., U.S. Pat. No. 4,816,567; Boss et al., U.S. Pat. No. 4,816,397; EP171496; EP173494, GB 2177096. Such chimeric antibodies are less immunogenic in a human subject than the corresponding non-chimeric antibody.

For human therapeutic purposes, the monoclonal or chimeric antibodies specifically reactive with an MRT polypeptide as described herein can be further humanized by producing human variable region chimeras, in which parts of the variable regions, especially the conserved framework regions of the antigen-binding domain, are of human origin and only the hypervariable regions are of non-human origin. General reviews of "humanized" chimeric antibodies are provided by Morrison, S. L. (1985) *Science* 229:1202–1207 and by Oi et al. (1986) *BioTechniques* 4:214. Such altered immunoglobulin molecules may be made by any of several techniques known in the art, (e.g., Teng et al. (1983) *Proc. Natl. Acad. Sci. U.S.A..*, 80:7308–7312; Kozbor et al. (1983) *Immunology Today*, 4:7279; Olsson et al. (1982) *Meth. Enzymol.*, 92:3–16), and are preferably made according to the teachings of W092/06193 or EPO 239400. Humanized antibodies can be commercially produced by, for example, Scotgen Limited, 2 Holly Road, Twickenham, Middlesex, Great Britain. Suitable "humanized" antibodies can be alternatively produced by CDR or CEA substitution (see U.S. Pat. No. 5,225,539 to Winter; Jones et al. (1986) *Nature* 321:552–525; Verhoeyan et al. (1988) *Science* 239:1534; and Beidler et al. (1988) *J. Immunol.* 141:4053–4060). Humanized antibodies which have reduced immunogenicity are preferred for immunotherapy in human subjects. Immunotherapy with a humanized antibody will likely reduce the necessity for any concomitant immunosuppression and may result in increased long term effectiveness for the treatment of chronic disease situations or situations requiring repeated antibody treatments.

As an alternative to humanizing a monoclonal antibody from a mouse or other species, a human monoclonal antibody directed against a human protein can be generated. Transgenic mice carrying human antibody repertoires have been created which can be immunized with an MRT polypeptide, such as human MRT. Splenocytes from these immunized transgenic mice can then be used to create hybridomas that secrete human monoclonal antibodies specifically reactive with an MRT polypeptide (see, e.g., WO 91/00906; WO 91/10741; WO 92/03918; WO 92/03917; Lonberg, N. et al. (1994) *Nature* 368:856–859; Green, L. L. et al. (1994) *Nature Genet.* 7:13–21; Morrison, S. L. et al. (1994) *Proc. Natl. Acad. Sci. USA* 81:6851–6855; Bruggeman etal. (1993) *Year Immunol* 7:33–40; Tuaillon et al. (1993) *Proc. Natl. Acad. Sci. USA* 90:3720–3724; and Bruggeman et al. (1991) *Eur J Immunol* 21:1323–1326).

Monoclonal antibody compositions of the invention can also be produced by other methods well known to those skilled in the art of recombinant DNA technology. An alternative method, referred to as the "combinatorial antibody display" method, has been developed to identify and isolate antibody fragments having a particular antigen specificity, and can be utilized to produce monoclonal antibodies that bind an MRT polypeptide of the invention (for descriptions of combinatorial antibody display see e.g., Sastry et al. (1989) *PNAS* 86:5728; Huse et al. (1989) *Science* 246:1275; and Orlandi et al. (1989) *PNAS* 86:3833). After immunizing an animal with an MRT polypeptide, the antibody repertoire of the resulting B-cell pool is cloned. Methods are generally known for directly obtaining the DNA sequence of the variable regions of a diverse population of immunoglobulin molecules by using a mixture of oligomer primers and PCR. For instance, mixed oligonucleotide primers corresponding to the 5' leader (signal peptide) sequences and/or framework 1 (FR1) sequences, as well as primer to a conserved 3' constant region primer can be used for PCR amplification of the heavy and light chain variable regions from a number of murine antibodies (Larrick et al. (1991) *Biotechniques* 11:152–156). A similar strategy can also been used to amplify human heavy and light chain variable regions from human antibodies (Larrick et al. (1991) *Methods: Companion to Methods in Enzymology* 2:106–110).

In an illustrative embodiment, RNA is isolated from activated B cells of, for example, peripheral blood cells, bone marrow, or spleen preparations, using standard protocols (e.g., U.S. Pat. No. 4,683,202; Orlandi, et al. *PNAS* (1989) 86:3833–3837; Sastry et al., *PNAS* (1989) 86:5728–5732; and Huse et al. (1989) *Science* 246:1275–1281.) First-strand cDNA is synthesized using primers specific for the constant region of the heavy chain(s) and each of the κ and λ light chains, as well as primers for the signal sequence. Using variable region PCR primers, the variable regions of both heavy and light chains are amplified, each alone or in combination, and ligated into appropriate vectors for further manipulation in generating the display packages. Oligonucleotide primers useful in amplification protocols may be unique or degenerate or incorporate inosine at degenerate positions. Restriction endonuclease recognition sequences may also be incorporated into the primers to allow for the cloning of the amplified fragment into a vector in a predetermined reading frame for expression.

The V-gene library cloned from the immunization-derived antibody repertoire can be expressed by a population of display packages, preferably derived from filamentous phage, to form an antibody display library. Ideally, the display package comprises a system that allows the sampling of very large diverse antibody display libraries, rapid sorting after each affinity separation round, and easy isolation of the antibody gene from purified display packages. In addition to commercially available kits for generating phage display libraries (e.g., the Pharmacia *Recombinant Phage Antibody System*, catalog no. 27-9400–01; and the Stratagene Sur-ZAP™ phage display kit, catalog no. 240612), examples of methods and reagents particularly amenable for use in generating a diverse antibody display library can be found in, for example, Ladner et al. U.S. Pat. No. 5,223,409; WO 92/18619; WO 91/17271; WO 92/20791; WO 92/15679; WO 93/01288; WO 92/01047; WO 92/09690; WO 90/02809; Fuchs et al. (1991) *Bio/Technology* 9:1370–1372; Hay et al. (1992) *Hum Antibod Hybridomas* 3:81–85; Huse et al. (1989) *Science* 246:1275–1281; Griffths et al. (1993) *EMBO J* 12:725–734; Hawkins et al. (1992) *J Mol Biol* 226:889–896; Clackson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc Acid Res* 19:4133–4137; and Barbas et al. (1991) *PNAS* 98:7978–7982.

In certain embodiments, the V region domains of heavy and light chains can be expressed on the same polypeptide, joined by a flexible linker to form a single-chain Fv fragment, and the scFV gene subsequently cloned into the desired expression vector or phage genome. As generally described in McCafferty et al., Nature (1990) 348:552–554, complete $V_H$ and $V_L$ domains of an antibody, joined by a flexible $(Gly_4-Ser)_3$ linker can be used to produce a single chain antibody which can render the display package separable based on antigen affinity. Isolated scFV antibodies immunoreactive with a peptide having activity of an MRT polypeptide can subsequently be formulated into a pharmaceutical preparation for use in the subject method.

Once displayed on the surface of a display package (e.g., filamentous phage), the antibody library is screened with an MRT polypeptide, or peptide fragment thereof, to identify and isolate packages that express an antibody having specificity for the MRT polypeptide. Nucleic acid encoding the selected antibody can be recovered from the display package (e.g., from the phage genome) and subcloned into other expression vectors by standard recombinant DNA techniques.

The polyclonal or monoclonal antibodies of the current invention, such as an antibody specifically reactive with a recombinant or synthetic peptide having an MRT activity can also be used to isolate the native MRT polypeptides from cells. For example, antibodies reactive with the peptide can be used to isolate the naturally-occurring or native form of MRT from, for example, plant cells by immunoaffinity chromatography. In addition, the native form of cross-reactive MRT-like molecules can be isolated from plant cells or other cells by immunoaffinity chromatography with an anti-MRT antibody.

IV. Uses and Methods of the Invention

The invention further pertains to methods for modulating metal concentration in a biological sample containing the metal. These methods include providing a transgenic plant in which expression of an MRT polypeptide is altered and contacting the transgenic plant with the biological sample such that the metal concentration in the biological sample is modulated. The term "modulating" as used herein refers to increasing or decreasing the concentration of a metal in a biological sample. As used herein, the term "metal" includes stable metals and radioactive metals such as iron, lead, chromium, mercury, cadmium, cobalt, barium, nickel, molybdenum, copper, arsenic, selenium, zinc, antimony, beryllium, gold, manganese, silver, thallium, tin, rubidium, vanadium, strontium, yttrium, technecium, ruthenium, palladium, indium, cesium, uranium, plutonium, and cerium. The term "metal" is also intended to include a mixture of two or more metals and mixtures of metals and common organic pollutants such as, for example, lead and chromium in combination with nitrophenol, benzene, and/or alkyl benzyl sulfonates (detergents). As used herein the phrase "biological sample" refers to a material, solid or liquid, in which it is desirable to modulate a metal concentration. Examples of biological samples include metal contaminated liquids such as industrial and residential waste streams, water-treatment plant effluents, ground and surface water, diluted sludge and other aqueous streams containing radioactive and nonradioactive metals, as well as soils or sediments. The soils or sediments can include a variety of soil types having wide ranges of water content, organic matter content, mineral content and metal content. As used herein, the phrase "transgenic plant in which expression of an MRT polypeptide is altered" refers to a transgenic plant in which an MRT polypeptide is misexpressed, e.g., the expression of an MRT polypeptide is enhanced, induced, prevented or suppressed. For example, a transgenic plant in which MRT polypeptide is altered, e.g., by misexpression, can be a metal accumulating plant.

"Misexpression", as used herein, refers to a non-wild type pattern of gene expression. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

To measure metal accumulation of a plant in a biological sample, seeds of a particular plant to be tested are grown in a greenhouse, the appropriate metal is administered to the plant and soil, and the roots and shoots harvested for routine determination of biomass and metal content. Chemical analysis of metal content in soils and plants is well characterized. See, e.g., Blincoe et al. (1987) *Comm. Soil. Plant Anal.* 18: 687; Baker et al. (1982) "Atomic Absorption Spectrometry," pp. 13–17 in *Methods of Soil Analysis*, part 2, *Am. Soc. Agron.*, Madison, Wis. Metal in plant tissues is preferably assayed with plasma spectrometry, allowing ashing and acid extraction. Metal remaining in the solution is measured, for example, by atomic absorption or plasma spectrometry. See, e.g., Soltanpour et al. (1982) "Optical emission spectrometry," pp. 29–65 in *Methods of Soil Analysis*, part 2, *Am. Soc. Agron.*, Madison, Wis.

Other methods of the invention include methods for removing a pollutant from soil, e.g., phytoremediation. These methods include contacting the transgenic plant in which expression of an MRT polypeptide is altered with the soil such that the pollutant is removed from the soil, i.e., the concentration of the pollutant in the soil prior to contact with the transgenic plant is greater than the concentration of the pollutant in the soil after contact with the transgenic plant. The term "pollutant" as used herein refers to any metal, e.g., radioactive or nonradioactive metal, that is found in the soil at toxic levels. As used herein, the phrase "toxic levels" refers to the concentration of metal which is higher than the concentration at which these metals naturally occur in the soil. Such toxic levels are usually produced by industries and other pollution centers. For example, metals such as mercury, cobalt, lead, arsenic, cadmium, zinc, copper, alone or in combination with other metals and/or detergents, as described above, are known soil pollutants.

Still other methods of the present invention include methods for treating a disorder associated with metal-deficiency, e.g., iron-deficiency or zinc-deficiency, in a subject. These methods include administering to a subject a therapeutically effective amount of a composition comprising the transgenic plant, or a portion thereof, in which expression of an MRT polypeptide is altered. In a preferred embodiment, the composition is administered in combination with a pharmaceutically acceptable carrier. In another preferred embodiment, the MRT polypeptide is overexpressed. Subjects who can be treated by the method of this invention include living organisms, e.g. mammals, e.g., humans. Examples of preferred subjects are those who have or are susceptible to iron-deficiency or zinc-defficiency, e.g., infants and women of childbearing age. As used herein, the phrase "a disorder associated with metal-deficiency" refers to any disease or disorder that results from a negative balance between metal intake and metal loss, e.g., iron intake and iron loss or zinc intake and zinc loss. For example, whenever there is rapid growth, as occurs during infancy, early childhood, adolescence and pregnancy, positive iron balance is difficult to maintain. Iron-deficiency can be the result of low dietary iron content, especially bioavailable iron, while in areas endemic for hookworm, intestinal blood loss secondary to heavy infestation contributes to iron-deficiency in both women and men. More severe forms of iron-deficiency usually result in anemia. In addition to iron, zinc is a metal with great nutritional importance, particularly during periods of rapid growth, due to its intervention in cellular replication as well as in development of the immune response. There is considerable evidence that zinc deficiency in humans is a serious worldwide problem and outweighs the potential problem of accidental, self-imposed, or environmental exposure to zinc excess. Acute deficiency (Henkin et al. (1975) *Arch Neurol* 322:745–751) and chronic deficiency (Prasad A. S. (1991) *Am J Clin Nutr* 53:403–412) are well-known entities in human populations and are probably much more common than generally recognized. The importance of zinc for human health was first documented in 1963 (Prasad et al. (1963) *J Lab Clin Med* 61:537–549). During the past 25 years, deficiency of zinc in humans due to nutritional factors and several disease states has now been documented throughout the world. Prevalence of zinc deficiency is high in populations that consume large quantities of cereal proteins containing high amounts of phytate, an organic phosphate compound. Alcoholism, malabsorption, sickle cell anemia, chronic renal disease, and other chronically debilitating diseases are known to be predisposing factors for zinc deficiency in humans (Prasad A S, (Prasad, A S, ed.) (1988) *New York:Alan R. Liss* 3–53).

Based upon clinical data and using traditional, epidemiologic techniques, Henkin and Aamodt (Henkin R I, Aamodt R L, (Inglett G E, ed.) (1983) *Washington:American Chemical Society* 83–105) have reclassified zinc deficiency into three syndromes; these are a) acute, b) chronic, and c) subacute zinc deficiency. Acute zinc deficiency is relatively uncommon and follows parenteral hyperalimentation or oral $_L$-histidine administration. Chronic zinc deficiency is more common, usually resulting from chronic dietary lack of zinc. Subacute or latent zinc deficiency is the most common of these syndromes. It is estimated that there are 4 million people in the United States with this syndrome, the initial symptom being dysfunction of taste and olfaction; treatment with exogenous zinc restores taste and smell but this usually requires months before these functions are returned to normal (Henkin et al. (1976) *Am J Med Sci* 272:285–299). Diagnosis of these disorders is most efficacious following oral administration of zinc tracers such as $^{65}$Zn, $^{67}$Zn, or $^{70}$Zn with subsequent evaluation of the kinetics of transfer of the isotope into various body tissues, the formulation of the data by compartmental analysis, and the integration of the data by a systematic model of zinc metabolism.

Clinical symptoms of human zinc-deficiency states exhibit a spectrum ranging from mild to severe and may even be fatal if unrecognized and not corrected (Prasad, A S (Prasad, A S, ed.) (1988) *New York:Alan R. Liss*, 3–53). The clinical manifestations of severely zinc deficient subjects include bullous pustular dermatitis, diarrhea, alopecia, mental disturbances, and intercurrent infections due to cell-mediated immune disorders. These severe signs are seen in patients with acrodermatitis enteropathica secondary to an inborn error of zinc absorption, patients receiving total parenteral nutrition without zinc, and patients receiving penicillamine therapy. Growth retardation, male hypogonadism, skin changes, poor appetite, mental lethargy, abnormal dark adaptation, and delayed wound healing are usual manifestations of moderate deficiency of zinc. Recent studies show that a mild or marginal deficiency of zinc in humans is characterized by neurosensory changes, oligospermia in males, decreased serum testosterone in males, hyperamonemia, decreased serum thymulin activity, decreased IL-2 production, decreased natural killer cell activity, alterations in T cell subpopulations (Prasad, A S (Prasad, A S, ed.) (1988) *New York:Alan R. Liss*, 3–53), impaired neuropsychological functions (Penland, J. G. (1976) *FASEB, J* 5:A938), and decreased ethanol clearance (Milne et al. (1991) *Am J Clin Nutr* 53:25).

The composition of the invention can be administered to the subject by a route of administration which allows the composition to perform its intended function. Various routes of administration are described herein in the section entitled "Pharmaceutical Compositions". Administration of a therapeutically active or therapeutically effective amount of the composition of the present invention is defined as an amount effective, at dosages and for periods of time, necessary to achieve the desired result.

Other aspects of the invention pertain to methods for evaluating a candidate compound for the ability to interact with, e.g., bind, an MRT polypeptide. These methods include contacting the candidate compound with the MRT polypeptide and evaluating the ability of the candidate compound to interact with, e.g., to bind or form a complex with the MRT polypeptide. These methods can be performed in vitro, e.g., in a cell free system, or in vivo, e.g., in a two-hybrid interaction trap assay. These methods can be used to identify naturally occurring molecules which interact with MRT polypeptides. They can also be used to find natural or synthetic inhibitors of MRT polypeptides.

Yet other aspects of the invention pertain to methods for identifying agents which modulate, e.g., inhibit or activate/stimulate, an MRT polypeptide or expression thereof. Also contemplated by the invention are the agents which modulate, e.g., inhibit or activate/stimulate MRT polypeptides or MRT polypeptide expression and which are identified according to methods of the present invention. In one embodiment, these methods include contacting a first polypeptide, e.g., a naturally occurring ligand of MRT, with a second polypeptide comprising an MRT polypeptide and an agent to be tested and determining binding of the second polypeptide to the first polypeptide. Inhibition of binding of the first polypeptide to the second polypeptide indicates that the agent is an inhibitor of an MRT polypeptide. Activation of binding of the first polypeptide to the second polypeptide indicates that the agent is an activator/stimulator of an MRT polypeptide.

V. Pharmaceutical Compositions

The transgenic plant in which the expression of MRT polypeptide is altered, or portions thereof, and other agents described herein can be incorporated into pharmaceutical compositions suitable for administration. Such compositions typically comprise the transgenic plant in which the expression of MRT polypeptide is altered, a portion thereof, or agent and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In one embodiment, polypeptides, compositions, transgenic plants or portions thereof, of the invention can be administered to a subject to treat metal-deficiency, e.g., iron- or zinc-deficiency, or can be administered to a subject, e.g., human or animal, as a nutritional supplement, e.g., as a metal source, e.g., as an iron or zinc supplement. The polypeptides, compositions, or plants are administered to the subjects in a biologically compatible form suitable for pharmaceutical administration in vivo. By "biologically compatible form suitable for administration in vivo" is meant a form of the polypeptide, composition, or plant, e.g., transgenic plant, to be administered in which any toxic effects are outweighed by the therapeutic effects of the polypeptide composition or plant. Administration of a therapeutically active or therapeutically effective amount of a polypeptide, composition, or plant of the present invention is defined as an amount effective, at dosages and for periods of time necessary to achieve the desired result. For example, a therapeutically active amount of a transgenic plant in which expression of MRT polypeptide is altered can vary according to factors such as the disease state, age, sex, and weight of the subject, and the ability of the composition to elicit a desired response in the subject. Dosage regimens may be adjusted to provide the optimum therapeutic response. For example, several divided doses can be administered daily or the dose can be proportionally reduced as indicated by the exigencies of the therapeutic situation.

The polypeptides, composition, or plant can be administered in a convenient manner such as by oral administration, e.g., as a nutritional supplement, injection (subcutaneous, intravenous, etc.), and other methods of parenteral administration. Depending on the route of administration, the polypeptide, composition, or plant can be coated in a material to protect it from the action of enzymes, acids and other natural conditions which may inactivate the agent.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

In one embodiment, the polypeptides, compositions, or plants are prepared with carriers that protect them against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These may be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of individuals.

To administer a polypeptide, composition, or plant by other than parenteral administration, it may be necessary to coat it with, or co-administer it with, a material to prevent its inactivation. For example, a transgenic plant in which expression of an MRT polypeptide is altered or a portion thereof can be administered to a subject in an appropriate carrier or diluent co-administered with enzyme inhibitors or in an appropriate carrier such as liposomes. Pharmaceutically acceptable diluents include saline and aqueous buffer solutions. Enzyme inhibitors include pancreatic trypsin inhibitor, diisopropylfluorophosphate (DEP) and trasylol. Liposomes include water-in-oil-in-water emulsions as well as conventional liposomes (Strejan et al. (1984) *J. Neuroimmunol* 7:27). Dispersions can also be prepared in glycerol, liquid polyethylene glycols, and mixtures thereof and in oils. Under ordinary conditions of storage and use, these preparations can contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which days absorption, for example, aluminum monostearate and gelatin.

Sterile injectable solutions can be prepared by incorporating the polypeptide, composition, or plant in the required amount in an appropriate solvent with one or a combination of ingredients enumerated above, as required, followed by filtered sterilization. Generally, dispersions are prepared by incorporating the polypeptide, composition, or plant into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (e.g., peptide) plus any additional desired ingredient from a previously sterile-filtered solution thereof.

This invention is further illustrated by the following examples which in no way should be construed as being further limiting. The contents of all cited references (including literature references, issued patents, published patent applications, and co-pending patent applications) cited throughout this application are hereby expressly incorporated by reference.

EXAMPLES

The Following Materials and Methods were Used in Examples 1–4

Yeast Growth Conditions and Library Screening

Yeast cells were grown in 1% yeast extract, 2% peptone supplemented with 2% glucose (YPD). The pH of liquid YPD medium was lowered to pH 4.0 with HCl to aid growth of fet3 fet4 double mutants. YPD medium was made iron-limiting by adding 80 $\mu$M bathophenanthroline disulfonate (BPS; Sigma, St. Louis, Mo.). Cells were also grown in synthetic defined medium (SD, 6.7 g/liter of yeast nitrogen base without amino acids) supplemented with 20 g/liter of glucose and necessary auxotrophic supplements. This medium was also supplemented with 10 $\mu$M FeCl$_3$ and the pH was lowered to 3.5 to aid growth of the fet3 fet4 strain. D-Y1453 (MATa/MATα ade2/+can1/can1 his3/his3 leu2/deu2 trpl/trpl ura3/ura3fet3-2::HIS3fet3-2::HIS3fet4-1::LEU2) was transformed using standard procedures (Schiesfi, R. H. et al. (1989) *Curr. Genet.* 16: 339–346) with a plasmid library containing *A. thaliana* cDNAs inserted under the control of the phosphoblycerate kinase promoter in pFL61 (Minet, M. et al. (1992) *Plant J.* 2: 417–422). The poly (A)$^+$ RNA used to construct this library was isolated from whole young seedlings (stage two leaves) grown on an iron-sufficient medium. Ura$^+$ transformants were isolated, pooled into 100 groups of 30,000 transformants each (i.e., 3×10$^6$ total transformants), and 1×10$^6$ cells from each pool were inoculated onto 100 YPD plus 80 $\mu$M BPS plates. Cells plated from six pools of transformants gave rise to several large colonies on this medium and a single colony was selected from each pool for further analysis. Plasmids were selectively removed from transformants using 5-fluoroorotic acid (Boeke, J. D. et al. (1987) *Methods Enzymol.* 154: 164–175).

Yeast DNA Manipulations

*Escherichia coli* TOP 10F' cells (Stratagene, La Jolla, Calif.) were used for all recombinant DNA procedures. The plasmid pZH1 was constructed by inserting the 1.4 kb NotI insert fragment from one isolate, pIRT-1, into the NotI site of pBluescript SK (+) (Stratagene, La Jolla, Calif.). Sequence analysis of the insert in pZH1 was performed by LARK Sequencing Technologies (Houston, Tex.). Computer database comparisons were performed using BLAST software (Altschul, S. F. et al. (1990) *J. Mol. Biol.* 215: 403–410); hydropathy analysis was performed and potential transmembrane segments were identified using the TOP-PREDII program (Claros, M. G. et al. (1994) *Comput. Appl. Biol. Sci.* 10: 685–686).

Iron Uptake Assays

Iron uptake assays using $^{55}$FeCl$_3$ (Amersham, Arlington Heights, Ill.) were performed as described (Eide, D. et al. (1992) *J. Biol. Chem.* 267: 20774–20781) except that MGN (10 mM Mes/2% glucose/1 mM nitrilotriacetic acid, pH 6.1) was used for the assay buffer. Where noted, 1 mM sodium ascorbate was added to reduce Fe(III) to Fe(II). Stock solutions of the chloride salt of each metal (except for iron) were prepared in water at a concentration of 100 mM and diluted into MGN to a final concentration of 10 $\mu$M before addition of the cells. The $^{56}$FeCl$_3$ stock was 50 mM prepared in 0.1 M HCl. The statistical significance of differences in values relative to controls was determined using STAT-VIEW software (Abacus Concepts, Berkeley, Calif.). Data was subjected to one-way analysis of variance (ANOVA) followed by a Scheffe's test.

Plant Growth Conditions

Seeds of *A. thaliana* (Columbia ecotype) WT,frd1, and frd3 (Yi, Y. (1995) Ph. D. thesis (Dartmouth College, Hanover, N.H.)) were surface-sterilized and sown on plates of Gamborg's B5 medium (Sigma, St. Louis, Mo.) with 2% sucrose, 0.5 g/liter Mes, and 6.7% agar (final pH 5.8). Plates were stored for 2 days in the dark at 4° C. and then incubated at 21° C. under constant illumination (65 $\mu$E m$^{-2.s-1}$) for 11 days. A 3-mm thick yellow acrylic filter (acrylic yellow-2208, Cadillac Plastic and Chemical, Pittsburgh, Pa.) was placed between the light source and the plates to prevent the photochemical degradation of Fe(III)-EDTA (Hangarter, R. P. et al. (1991) *Plant Physiol.* 96: 843–847). Seedlings were then transferred to either iron-sufficient or iron-deficient nutrient plates. The medium contained macro- and micro-nutrients (Marschner, H. et al. (1982) *Z. Pflanzenphysiol.* 105: 407–416) plus 0.7% agar and 0.5 g/liter of Mes (final pH 6.0). The iron-sufficient medium contained 50 $\mu$M Fe(III)-EDTA and the iron-deficient medium contained 300 $\mu$M FerroZine [3-(2-pyridyl)-5,6-diphenyl-1,2,4-triazine sulfonate, HACH Chemical (Ames, Iwoa)]. Plates were incubated for 3 days in the growth chamber described above.

Arabidopsis Nucleic Acid Analysis

For Southern blot analysis, 15-$\mu$g samples of Arabidopsis genomic DNA (Dellaporta, S. L. et al. (1983) *Plant Mol. Biol. Rep.* 1: 19–21) were digested overnight with the appropriate restriction enzymes, separated by electrophoresis on a 0.8% agarose gel, transferred to a nitrocellulose membrane, and bound to the membrane by UV crosslinking (Stratalinker; Stratagene, La Jolla, Calif.). Standard procedures were used for prehybridization and hybridization (Ausubel, F. M. et al. (1995) *Current Protocols in Molecular Biology* (Wiley, New York). Membranes were then washed twice at room temperature for 15 min in 5×SSPE, 0.1% SDS, followed by two 15 min washes in 0.1×SSPE, 0.1% SDS at 50° C. (high stringency) or at room temperature (low stringency). Membranes were stripped for reprobing with a boiling solution of 1×SSC, 0.1% SDS. Southern blot analysis of genomic DNA from Columbia and Landsberg ecotypes digested with SalI and probed with a labeled IRT1 fragment revealed a restriction fragment length polymorphism between these lines. To map IRT1, Southern blots of genomic DNA from recombinant inbred lines (Lister, C. et al. (1993) *Plant J.* 4: 745–750.) were then analyzed for segregation of the polymorphism. The IRT1 segregation data were compared with the segregation patterns of other markers and the IRT1 map position was determined using MAPMAKER software (Lander, E. S. et al. (1987) *Genomics* 1: 174–181). RNA was extracted (Verwoerd, T. C. et al. (1989) *Nucleic Acids Res.* 17: 2362) from root and shoot fractions of plants that had been grown axenically on either iron-sufficient or iron-deficient plates. Samples (10 µg) of RNA were denatured and electrophoresed on a 0.8% agarose, 6.2% formaldehyde gel and then transferred to a nylon membrane (BioTrans; ICN). RNA was bound to the membrane by UV crosslinklng (Stratalinker; Stratagene, La Jolla, Calif.). The membrane was prehybridized, hybridized, washed, and stripped as described by Pilgrim and McClung (Pilgrim, M. L. & McClung, R. (1993) *Plant Physiol.* 103: 553–564). DNA fragments used as hybridization probes were radio labeled by the random primer method (Feinberg, A. P. et al. (1984) *Anal. Biochem.* 137: 266–267). For Southern blot analysis, the 1.4-kb EcoRI/XbaI insert fragment of expressed sequence tag (EST) 37F12T7 were used as probes for IRT1 and IRT2, respectively. The same IRT1 DNA fragment was used as a probe for Northern blot analysis as well as the 2.5-kb EcoRI insert fragment of pARR16 encoding rRNA (Richards, E. et al. (1988) *Cell* 53: 127–136).

The Following Materials and Methods were Used in Examples 6–9

Yeast Strains and Culture Conditions

Strains used were DY1457 (MATα ade6 can1 his3 leu2 trp1 ura3) and ZHY1 (MaTα ade6 can1 his3 leu2 trp1 ura3 zrt1:: LEU2). Yeast were grown in standard culture media (SD, YPD) (Eide, D., Davis-Kaplan S., Jordan, I., Sipe, D., and Kaplan, J. (199: 2) *J. Biol. Chem.* 267, 20774–20781) supplemented with necessary auxotrophic requirements and either 2% glucose or 2% galactose. A zinc-limiting medium (LZM) was prepared in the same manner as LIM (Eide and Guarenete (1992) *J. Gen. Microbiol.* 138:347–354) except that $ZnSO_4$ in LIM was replaced with 10 µM $FeCl_3$ in LZM. Cell number in liquid cultures was determined by measuring the optical density of cell suspensions at 600 nm ($A_{600}$) and converting to cell number with a standard curve.

Plasmids and DNA Manipulations

*E. coli* and yeast transformations were performed using standard methods (Sambrook and Maniatis (1989) *Molecular Cloning: A Laboratory Manual* (Cold Spring Harbor Lab. Press, Plainview, N.Y.), 2nd Ed.; Schiestl and Gietz (1989) *Curr. Genet.* 16:339–346). Plasmids constructed are diagrammed in FIG. 6. A fragment bearing the ZRT1 open reading frame was prepared by the polymerase chain reaction (PCR) using primers derived from the ZRT1 sequence with either BamHI (Primer 3) or SalII restriction sites (Primer 4) added to their 5' ends (FIG. 6, Primer 3: 5'-CGGATCC/ATGAGCAACGTTACTACG-3' (SEQ ID NO:15) and Primer 4: 5'-TACGCGTCGAC/TTAAGCCC-ACTTACCGAT-3' (SEQ ID NO:16); the slash indicates the beginning of the ZRT1 sequences in each primer). The resulting fragment was inserted into Bluescript SK+ (Stratagene, La Jolla, Calif.) to generate pSK+ZRT1. A PstI fragment containing the LEU2 gene was prepared as described (Dix et al. (1994) *J. Biol. Chem.* 269:26092–26099) and inserted into pSK+ZRT1 to generate pZH2. This plasmid contains the zrt1 disruption mutation, zrt1::LEU2. Plasmid pZH2 was digested with BamHI arid SalII and transformed into DY1457 to replace the chromosomal locus by single-step gene transplacement (Rothstein, R. (1991) *Methods Enzymol.* 194:281–301). The resulting strain, ZHY1, was confirmed to contain the zrt1::LEU2 mutation by Southern blot analysis. Because ZHY1 grows more slowly than the wild type strain on media containing metal chelators, a plasmid (pMC5) containing a genomic ZRT1 fragment was isolated from a genomic library (Carlson and Botstein (1982) *Cell* 28:145–154) by complementation (Rose and Broach (1991) *Methods Enzymol.* 194:195–230) of the growth defect displayed by ZHY1 on YPD+200 µM bathophenanthroline disulfonate (Sigma Chemical Co., St. Louis, Mo.). The 2.2 kb SacI-HindIII fragment from pMC5 containing the genomic ZRT1 gene was subcloned into pRS316 (Sikorski and Boeke (1991) *Methods Enzymol.* 194:302–318) to generate pMC5-HS. The BamHI-SalI fragment generated with Primers 3 and 4 was also cloned into pRS316-GAL1 (Liu et al. (1992) *Genetics* 132:665–673) to generate pOE1. A PCR fragment containing bases −706 to +3 of ZRT1 (the first base of the ATG initiation codon is designated as position +1) was generated with Primers 1 and 2 (FIG. 6, Primer 1: 5'-GGAATTC/GAAGG-CAAGAGTATTTCAGAC-3' 9 SEQ ID NO:17), Primer 2: 5'-CGGGATC/CATAATTCCTTTTT-TGATATTTG-3' (SEQ ID NO:18); the slash indicates the beginning of the ZRT1 sequence in each primer). This PCR fragment was digester with EcoRI and BamHI and inserted into the yeast integrating vector YIp353 (Myers et al. (1986) *Gene* 45:299–310) to generate pGI1. This plasmid contains a fusion between the ZRT1 upstream flanking sequences, 5' untranslated region, and initiation methionine residue, and the *E. coli* lacZ gene. Plasmid pGI1 was then digested with NcoI, and transformed into DY1457 and ZHY1 to integrate the plasmid at the URA3 locus (Dix et al. (1994) *J. Biol. Chem.* 269:26092–26099). The plasmid pHYC3 contains HIS4 promoter elements fused to lacZ (Hinnebusch et al. (1985) *Proc. Natl. Acad. Sci. USA* 92:499–502). Database comparisons were performed with the National Center for Biotechnology Information databases using BLAST (Altschul et al. (1990) *J. Mol. Biol.* 215:403–410), and topology analysis was performed using the TOP-PREDII program (Claros and von Heijne (1994) *Comput. Appl Biosci.* 10:685–686).

Zinc uptake and β-galactosidase Assays

Zinc uptake assays were performed as described previously for iron uptake (Eide et al. *J. Biol. Chem.* 267:20774–20781) except that $^{65}ZnCl_2$ (Amersham Corp., Arlington Heights, Ill.) and LZM-EDTA were substituted for $^{59}FeCl_3$ and LIM-EDTA. Cells were incubated at 30° C. with $^{65}Zn$ for five minutes, filtered, and washed with 10 ml ice-cold SSW. Cell-associated radioactivity was measured by liquid scintillation. Kinetic values were derived using KinetAsyst software (IntelliKinetics, Princeton, N.J.). Zinc accumulation was measured in cells grown in LZM medium supplemented with 10 mM $^{65}Zn$ plus nonradioactive zinc to the indicated final concentration. Aliquots (0.5 ml) were filtered, washed with 10 ml ice-cold SSW, and counted by liquid scintillation. b-galactosidase activity was assayed as described by Guarente (Guarante, L. (1983) *Methods Enzymol* 101:181–191).

RNA Isolation and Northern Blot Analysis

Total RNA was isolated from yeast (Sherman et al. (1986) *Methods in Yeast Genetics* (Cold Spring HarboLab. Press, Plainview, N.Y.)), denatured, separated by agarose gel electrophoresis (6 µg /lane), and analyzed by Northern blotting (Sambrook and Maniatis (1989) *Molecular Cloning: A Laboratory Manual* (Cold Spring Harbor Lab. Press, Plainview, N.Y.), 2nd Ed). Equal loading of RNA in each lane was confirmed by staining the gel with acridine orange. Probes used were the ZRT1 BamHI-SalI insert of pSK+

ZRT1 and ACT1 labeled with $^{32}$P (Amersham Corp., Arlington Heights, Ill.) by the random priming method (Feinberg and Vogelstein (1984) *Anal. Biochem.* 137:266–267). Densito-metric scanning was performed using a Sierra Scientific CCD camera and Image 1.4 software (National Institutes of Health, Bethesda, Md.).

The Following Materials and Methods were Used in Examples 10–14

Strains and Culture Methods

Strains used were DY1457 (MATα ade6 can1 his3 leu2 trp1 ura3), ZHY1 (AMTα ade6 can1 his3 leu2 trp1 ura3 zrt1::LEU2), ZHY2 (MATα ade6 can1 his3 leu2 trp1 ura3 zrt2::HIS3), and ZHY3 (MATα ade6 can1 his3 leu2 trp1 ura3 zrt1::LEU2 zrt2::HIS3). Yeast were grown in YP or SD media (Sherman et al. (1986) *Methods in Yeast Genetics*, Cold Spring Harbor Laboratory, Cold Spring Harbor, N.Y.) supplemented with necessary auxotrophic requirements and either 2% glucose or 2% galactose. Zinc-limiting YP and SD agar plates contained either bathophenanthroline disulfonate (BPS, 200 μM) or EDTA (1 mM), respectively. A liquid zinc-limiting medium (low zinc medium, LZM) was prepared in the same manner as low iron medium (LIM) (Eide and Guarente (1992) *J. Gen. Microbiol.* 138:347–354) except that the $ZnSO_4$ in LIM was replaced with 10 μM $FeCl_3$ in LZM. LZM is similar in composition to SD medium with two modifications essential to controlling zinc availability. First, 1 mM EDTA is added to provide buffering for the concentration of free metal ions. Second, the medium is pH-buffered at 4.2 with 20 mM citrate to prevent pH changes that could alter the metal binding ability of EDTA. LZM was also prepared without EDTA (LZM-PDTA) which is less zinc-limiting because the predominant chelator in this medium, citrate, binds zinc with less affinity than does EDTA. The concentrations of free (i.e. unchelated) zinc were calculated using MAXCHELATOR software (Chris Patton, Stanford University). Cell number in liquid cultures was determined by measuring the absorbance of cell suspensions at 600 nm ($OD_{600}$) and converting to cell number with a standard curve.

Zinc Uptake and β-galactosidase Assays

Zinc uptake assays were performed as described previously for iron uptake (Eide et al. (1992) *J. Biol. Chem.* 267:20774–20781) except that $^{65}ZnCl_2$ (Amersham) and LZM-EDTA were substituted for $^{59}FeCl_3$ and LIM-EDTA, respectively. Cells were incubated for 5 minutes in LZM-EDTA plus the indicated concentration of $^{65}Zn$, collected on glass fiber filters (Schleicher and Schuell), washed with 10 ml ice-cold SSW (1 mM EDTA, 20 mM trisodium citrate, 1 mM $KH_2PO_4$, 1 mM $CaCl_2$, 5 mM $MgSO_4$, 1 mM NaCl pH 4.2), and cell-associated radioactivity was measured by liquid scintillation counting. Cells were starved for glucose by incubating them in LZM-EDTA prepared without glucose for one hour at 30° C. prior to assay. Michaelis-Menten kinetic values were determined using KINETASYST software (Intellikinetics, Princeton, N.J.). Stock solutions of the chloride salts of Co, Cu, Mg, Mn, and Ni were prepared in distilled water at a concentration of 100 mM. The nonradioactive $ZnCl_2$ stock was prepared at 100 mM in 0.02 N HCl and the $FeCl_3$ stock was prepared at 50 mM in 0.1 N HCl. The statistical significance of the differences of values relative to controls was determined with one-way analysis of variance (ANOVA) followed by a Dunnett multiple comparison test. β-galactosidase activity was assayed in cells harvested at an $OD_{600}$ of 0.5–2.0 as described by Guarente (Guarente, L. (1983) *Methods Enzymol.* 101:181–191) and activity is expressed as the change in absorbance at 420 nm×1000 divided by (min×ml of culture used×$OD_{600}$ of the culture). Cell-associated zinc was measured in parallel cultures supplemented with tracer amounts of $^{65}Zn$ (10 μM) and nonradioactive zinc to the indicated final concentration. Aliquots (0.5 ml) were filtered, washed with 10 ml ice-cold SSW, and radioactivity measured by liquid scintillation.

Isolation of the ZRT2 Gene and DNA Manipulations

*E. coli* and yeast transformations were performed using standard methods (Sambrook et al. (1989) *Molecular Cloning: A Laboratory Manual*, 2nd Ed., (Cold Spring Harbor Laboratory, Cold Spring Harbor, N.Y.); Schiestl, and Gietz (1989) *Curr. Genet.* 16:339–346). To screen for multicopy suppressors of the zrt1 mutation, ZHY1 cells were transformed with a genomic library constructed in the multicopy vector YEp24 (Carlson and Botstein (1982) *Cell* 28:145–154). Approximately 40,000 Ura$^+$ transformants were isolated and replated onto zinc-limiting YP glucose+BPS agar plates. Three independent transformants were isolated that formed larger colonies on this medium than the untransformed parent strain. Plasmid-dependence was verified by selectively removing the plasmids from each transformant with 5-fluoroorotic acid (Boeke et al. (1987) *Methods Enzymol.* 154:164–175) followed by replating onto YP glucose+BPS. DNA was prepared from each transformant, and the plasmids were then transformed into *E. coli* TOP10F' (Invitrogen). Plasmid DNA was prepared, restriction mapped, and the ends of the inserts were sequenced as described by Borson et al. (Borson et al. (1992) *PCR Methods Appl.* 2:144–148). This analysis demonstrated that two of the plasmids (pMC1 and pMC5) have cDNA inserts containing ZRT1. The third plasmid, pMC4, contains the ZRT2 gene. Computer database comparisons were performed using BLAST (Altschul et al. (1990) *J. Mol. Biol.* 215:403410), potential transmembrane domains were identified using TOP-PREDII (Claros and von Heijne (1994) *Comput. Appl. Biosci.* 10:685–686), and multiple sequence alignment was performed using PILEUP (Genetics Computer Group) (Devereux et al. (1984) *Nucleic Acids Res.* 12:387–395).

A fragment bearing the ZRT2 open reading frame was prepared from pMC4 by the polymerase chain reaction (PCR) using primers derived from the ZRT2 sequence with either SalI (Primer 1: 5'-ACGCGTCGACATGGTTGATCTTATAGCGAG-3' (SEQ ID NO:19)) or SacI restriction sites (Primer 2: 5'-CCCGAGCTCCTATGCCCATTT CCCTAG-3' (SEQ ID NO:20)) added to their 5' ends. The resulting fragment was inserted into Bluescript SK$^+$ (Stratagene, La Jolla, Calif.) to generate pSK$^+$ZRT2. A BamHI fragment containing the HIS3 gene was prepared from YCp407 (Stearns et al. (1990) *Methods Enzymol.* 185:280–297) and inserted into pSK$^+$ZRT2 to generate pZH3. This plasmid contains the zrt2 disruption mutation, zrt2::HIS3. Plasmid pZH3 was digested with SalI and SacI to liberate the zrt2::HIS3 fragment and transformed into DY1457 and ZHY1 to replace the chromosomal locus by single-step gene transplacement (Rothstein, R. (1991) *Methods Enzymol.* 194:281–301). The resulting strains, ZHY2 and ZHY3, were confirmed to contain the zrt2::HIS3 allele by Southern blot analysis. The SalI-SacI PCR fragment generated with Primers 1 and 2 was also cloned into pRS316-GAL1 (Liu et al. (1992) *Genetics* 132:665–673) to generate pOE2. The plasmid pGI1 (Zhao and Eide (1996) *Proc. Natl. Acad. Sci. USA*. 93:2454–2458), containing a fusion between the ZRT1 promoter and the *E. coli* lacZ gene, was digested with NcoI and transformed into DY1457, ZHY1, ZHY2 and ZHY3 to integrate the plasmid at the URA3 locus (Rothstein, R. (1991) *Methods Enzymol.* 194:281–301).

Example 1

Isolation and Sequence Analysis of the IRT1 Gene

An *A. thaliana* cDNA library was screened for clones that, when expressed in *S. cerevisiae*, could restore iron-limited growth to a yeast strain defective for iron uptake. A fet3 fet4 double mutant is sensitive to iron limitation due to its reliance on additional and apparently less efficient uptake mechanisms. This mutant strain was transformed with an Arabidopsis cDNA library constructed in a yeast expression vector, and approximately 3×10⁶ independent transformants were screened on a rich medium made iron-limiting by adding the Fe(II) chelator, BPS. Six independent transformants that formed larger colonies on this medium were isolated. The plasmids carried by these transformants were required for the improved growth; this ability was lost when the plasmid was removed from each strain. Restriction endonuclease mapping indicated that all six plasmids contain inserts derived from the same gene. The gene has been designated IRT1 for iron-regulated transporter. IRT1 mapped to chromosome 4 by restriction fragment length polymorphism analysis (Lister, C. et al. (1993) *Plant J*. 4: 745–750).

The entire cDNA insert of one of the six plasmids, pIRT-1, was sequenced and found to be 1348 bp in length and to contain a single 1017 bp open reading frame capable of encoding a polypeptide of 339 amino acids (FIG. 1A). The predicted amino acid sequence of IRT1 shows that it is an integral membrane protein. Greater than 60% of the amino acids are nonpolar and these are arrayed in eight regions longer than 20 amino acids. These eight regions form transmembrane domains. The hydrophobic nature of the IRT1 amino acid sequence and the arrangement of potential transmembrane domains, coupled with the biochemical analysis described herein, demonstrates that IRT1 is an Fe(II) transport protein. Therefore, the IRT1 amino acid sequence was examined for potential metal-binding domains. IRT1 has four histidine-glycine repeats located at amino acids 154–161 in the region between transmembrane domains 3 and 4. This histidine-rich domain is important in substrate binding or regulation of this transporter. Several metal-binding proteins use the imidazole ring nitrogen of histidine as a coordinating ligand for metal ions (Karlin, D. D., (1993) *Science*, 261: 701–708.29; O'Halloran, T. V. (1993) *Science*, 261:715–725.). Moreover, similar domains [i.e., (-His-X-)$_{3-6}$] are found in analogous positions in the amino acid sequences of four other proteins thought to play a role in metal transport (Kamizono, A. et al. (1989) *Mol Gen. Genet*. 219: 161–167.31; Conklin, D. S. et al. (1992) *Mol Cell. Biol*. 12: 3678–368832; Palmiter, R. D. et al. (1995) *EMBO J*. 14: 639–649).

Example 2

IRT1 is a Member of a Gene Family

The predicted amino acid sequence of IRT1 has no detectable similarity to FET3 (Dix, D. R. et al. (1994) *J. Biol. Chem*. 269: 26092–26099), FET4 (Askwith, C. et al. (1994) *Cell* 76: 403–410), or COPT1, a putative copper transporter from *A. thaliana* (Kampfenkel, K. et al. (1995) *J. Biol. Chem*. 270: 28479–28486). Also, although they share the same number of potential transmembrane domains, there is no detectable similarity between IRT1 and the *E. coli* Fe(II) transporter protein encoded by the feoB gene (Kamler, M. et al. (1993) *J. Bacteriol*. 175: 6212–6219). The lack of similarity among these proteins suggests that each may transport the substrate by a different biochemical mechanism. However, comparison of the IRT1 amino acid sequence with GenBank™, EMBL, and SWISS-PROT databases identified two closely related sequences in *Arabidopsis*. Amino acids 8 through 127 of IRT1 are 72% (86 of 119) identical and 86% similar (i.e., identities plus conservative substitutions) to the predicted amino acid sequence of a cDNA partially sequenced as an EST (FIG. 1B). Because of this high degree of similarity to IRT1, this gene has been designated IRT2. Furthermore, the carboxylterminal 47 amino acids of IRT1 are 45% (21 of 47) identical and 68% similar to the sequence of a partially sequenced open reading frame located downstream of the ferrodoxin-encoding FEDA gene (Somers, D. E. et al. (1990) *Plant Physiol*. 93: 572–577). This gene is referred to as IRT3. The GenBank™ data base accession numbers for IRT2, IRT3, and the rice EST are T04324, M35868, and D49213, respectively. The numbers refer to the IRT1 amino acid sequence, bars indicate positions of amino acid identity, and positions of conservative substitutions are indicted by the colons. Conservative substitutions are based on the following groupings of amino acids: (L, I, V, M) (A, G, P, S, T) (R, K, H), (Q, D, E, N), and (F, Y, W)(Dayhoff, M. O. et al. (1978) in *Atlas of Protein Sequence and Structure* (Natl. Biomed. Res. Found., Silver Spring, Md.), pp. 345–352).

A low stringency Southern blot using IRT1 as the probe confirmed that IRT1 is a member of a small gene family. A comparison of the hybridization patterns seen on Southern blots using IRT1 and IRT2 as probes indicates that some of the bands seen on the low stringency Southern blot probed with IRT1 can be attributed to IRT2. When *A. thaliana* DNA was digested with EcoRI, IRT1 and IRT2 hybridized strongly to 4.2- and 9.6-kb fragments, respectively. The same fragments showed weak (but visible) hybridization with the opposite probes, i.e., IRT1 weakly hybridized to the 9.6-kb fragment and IRT2 weakly hybridized to the 4.2-kb band. Digestion with the enzymes HincII and AvaI generated a 1.2-kb fragment that hybridized strongly to IRT1 and a 1.8-kb fragment that strongly hybridized to IRT2. Again, both fragments showed weak hybridization to the opposite probes. With both digestions, other weakly hybridizing fragments were visible that could not be attributed to either IRT1 or IRT2. These fragments represent additional members of the IRT1 gene family, such as IRT3, present in the *A. thaliana* genome. Furthermore, DNA sequences similar to IRT1 were detected by low stringency hybridization of the IRT1 cDNA to DNA isolated from several other dicots including tomato, broccoli, and mustard.

Database comparisons also identified IRT1 related genes in the genomes of rice (a strategy II plant) (FIG. 1B), yeast, nematodes, and humans. The rice gene was identified as an EST and has 64% identity and 82% similarity to IRT1 over an 84-aa region. Two related *S. cerevisiae* genes (GenBank™ accession nos. P32804 and X91258) were identified. Both of these genes encode proteins that are similar in length to IRT1 (376 and 422 amino acids) and are ≈30% identical and 60% similar to IRT1. These genes were identified as open reading frames in the course of genomic sequencing and their functions Eare currently being investigated. The nematode sequence (GenBank™ accession no. U28944) was also identified by genomic sequencing and has 23% identity and 47% similarity to IRT1 over an 84 amino acid stretch. Finally, a human EST (GenBank™ accession no. H20615) was identified with 31% identity and 43% similarity to IRT1 over 82 amino acids. Given their close similarity to IRT1, these related genes encode metal transporters in the organisms in which they are found.

Example 3

IRT1 Expression Confers Iron Uptake Activity

Figure 2:
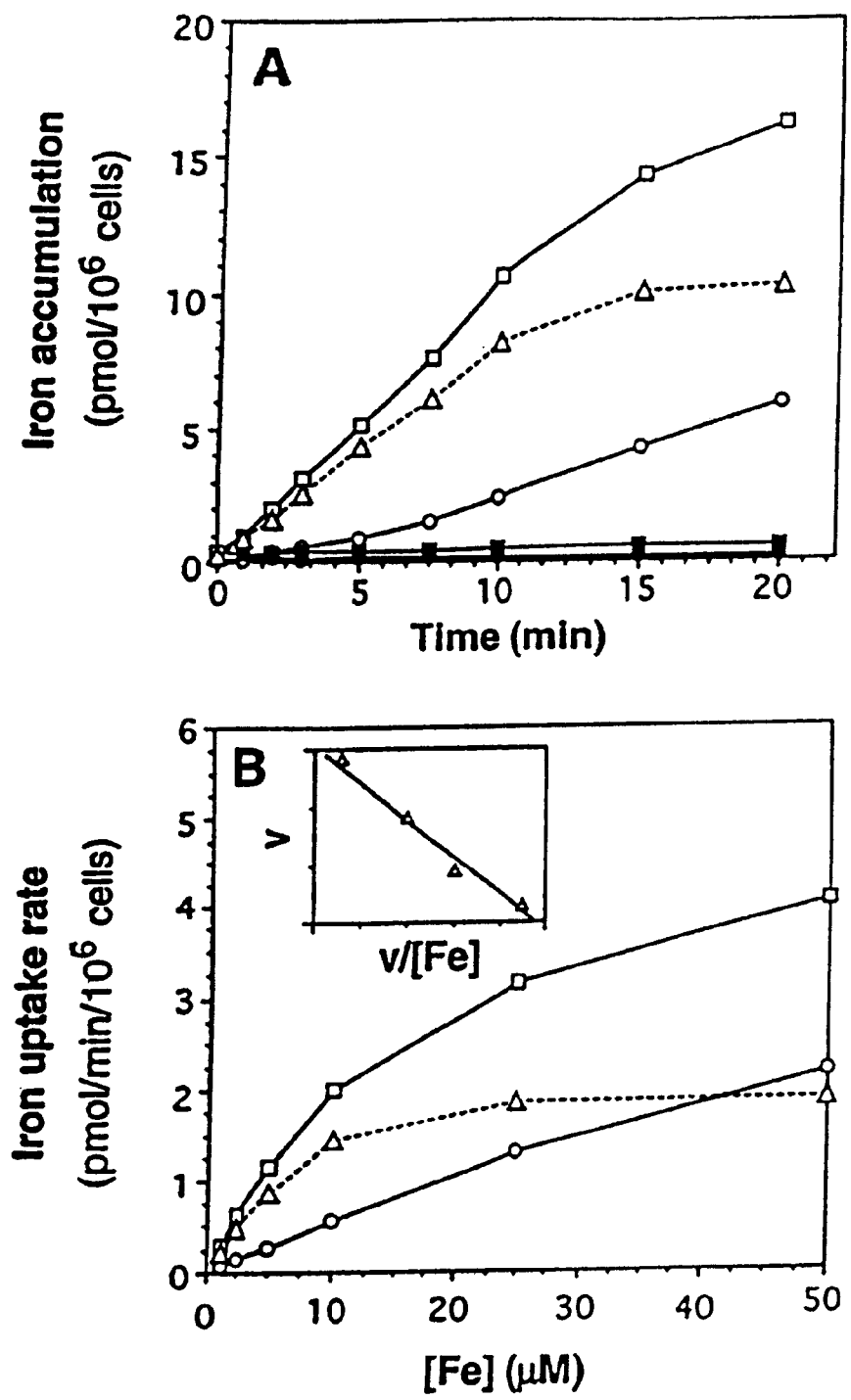
FIGS. 2A and 2B are graphs depicting the effect of IRT1 expression on iron uptake in yeast.

To determine if IRT1 encodes an iron transporter, $^{55}$Fe uptake rates were examined in a fet3 fet4 strain expressing IRT1. Little or no uptake was detected at 0° C. for either IRT1-expressing or untransformed control cells (FIG. 2A). The fet3 fet4 mutant strain DEY1453 (circles) and DEY1453 transformed with pIRT-1 (squares) were grown to exponential phase in SD glucose and assayed for iron uptake with $^{55}$Fe. (A) Time- and temperature-dependence of iron accumulation assayed in MGN with 1 mM ascorbate and 5 $\mu$M $^{55}$FeCl$_3$ assayed at 30° C. (open symbols) or 0° C. (solid symbols). The dashed line marked with open triangles represents the IRT1-dependent accumulation, i.e., the accumulation of iron by the untransformed strain at 30° C. subtracted from the accumulation of the pIRT-1-bearing strain at 30° C. At 30° C., IRT1 expression resulted in an increased uptake rate for the first 10 min of the assay, after which the rate dropped to the control level. The IRT1-dependent rate was ≈3-fold higher than the control uptake rate. No increased uptake was apparent in strains bearing either of two randomly selected clones from the library, indicating the dependence of these uptake effects on expression of IRT1. The iron uptake activity dependent on IRT1 expression was also concentration-dependent and saturable (FIG. 2B). The same strains as in A were assayed for iron uptake rates for 10 min over a range of concentrations. The dashed lines marked with open triangles represents the IRT1-dependent uptake rate, i.e., background uptake rate of the untransformed strain subtracted from the corresponding rate of the pIRT-1-bearing strains. (Inset) Eadie-Hofstee plot of the IRT1-dependent uptake data. Each point represents the mean of three experiments each performed in duplicate. The standard deviation within each experiment was less that 20% of the corresponding mean. The concentration dependence of IRT1-mediated uptake was found to generate a linear Padie-Hofstee plot (FIG. 2B, Inset) with an apparent $K_m$ of 6±1 $\mu$M and a $V_{max}$ of 1.9±0.4 pmol per min per $10^6$ cells. Taken together, these results show that IRT1 expression in yeast produces a time-, temperature-, and concentration-dependent system of iron uptake.

Figure 3:
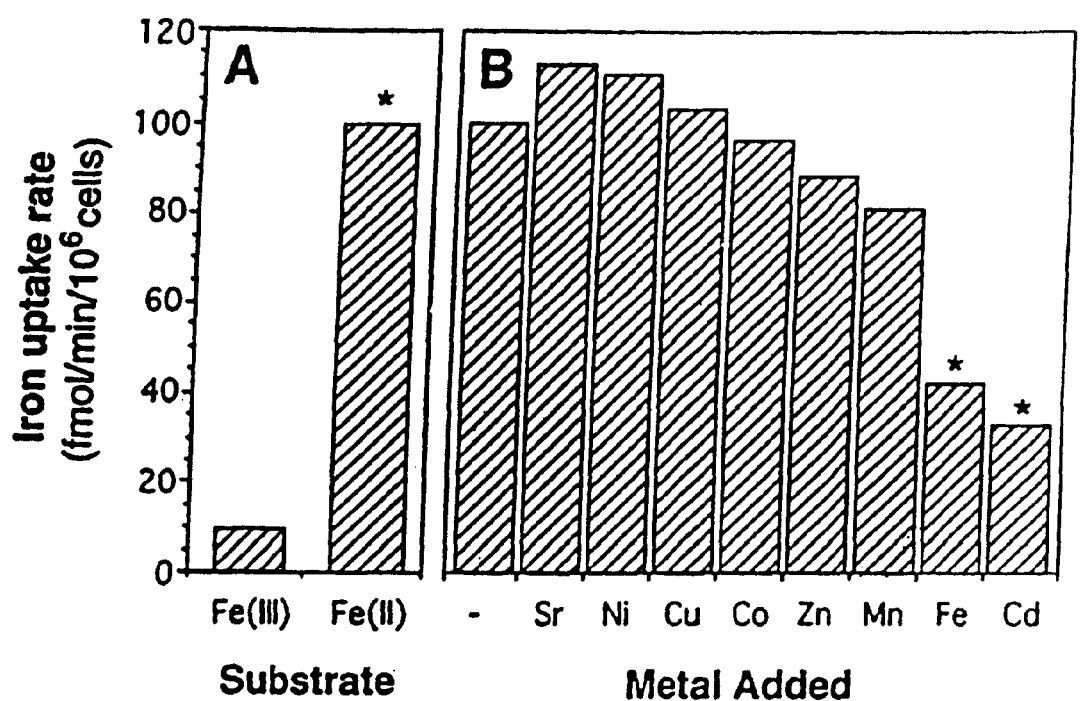
FIG. 3A is a bar graph depicting the inhibition of IRT1-dependent uptake in yeast by other metals.
FIG. 3B is a bar graph depicting the inhibition of IRT1-dependent uptake by other transition metals.

The experiments described above were conducted with iron supplied as Fe(II), i.e., in the presence of ascorbate, an agent capable of reducing Fe(III) to Fe(II). To determine if Fe(II) is the preferred substrate over Fe(III), assays were carried out in the absence of ascorbate where iron is supplied to the cells as Fe(III). It has been found that the iron uptake rate in the absence of ascorbate was ≈10% of the rate when ascorbate was present (FIG. 3A). The fet3 fet4 mutant strain DEY1453 and DEY1453 transformed with pIRT-1 were grown to exponential phase is SD glucose and assayed for iron uptake with 1 $\mu$M FeCl$_3$ in MGN for 10 min. The values shown are the IRT1-dependent rates, i.e., the untransformed strain control values were subtracted from the DEY1453 pIRT-1 values and represent the means of four replicates. The asterisks indicate significant of differences from the control values (P<0.05). Assays were performed in the absence [Fe(III)] or presence [Fe(II)] of 1 mM ascorbate. This result shows that Fe(II) is preferred over Fe(III) as substrate for the IRT1 transporter. Although yeast are capable of reducing Fe(III) to Fe(II) through the action of plasma membrane Fe(III) reductases, this rate of cell-mediated reduction is slower than reduction by ascorbate and therefore may be rate-limiting for IRT1-dependent uptake. To assess if metals other than iron are potential substrates for IRT1, several transition metals were tested for their ability to inhibit accumulation of iron in IRT1-expressing cells (FIG. 3B). Assays were conducted in the absence (-) or presence of 10 $\mu$M metal. Radioactive iron was supplied as Fe(II) in the presence of 1 mM ascorbate. Iron was supplied as Fe(II) in these assays (i.e., in the presence of ascorbate) and the concentration of the metals tested was 10 times higher than the concentration of radio-labeled iron. The addition of Sr, Ni, Cu, Co, Zn, and Mn had no significant effect on the rate of iron uptake by IRT1. Cd and nonradiolabeled Fe(II) proved to be potent inhibitors of iron uptake. At 100-fold excess, Co, Mn, and Zn were also found to inhibit IRT1-dependent iron uptake. The observed decreases in iron uptake rate were not due to toxicity of any of these metals because control experiments detected no loss of cell viability resulting from metal exposure. Therefore, although the mechanism of this inhibition is not yet known, these data show that IRT1 is relatively specific for Fe(II) but is also capable of transporting Cd, Co, Mn, and/or Zn.

Example 4

Regulation of IRT1 in Wild-Type and Mutant Plant Lines in Response to Iron

IRT1 mRNA is expressed at a high level in roots of iron-deficient plants; no signal was detected on a Northern blot with total RNA prepared from roots of iron-sufficient plants or from shoots of iron-sufficient or iron-deficient plants. The signal detected on the Northern blot is specific for IRT1; using gene-specific probes for IRT1 and IRT2, no hybridization was detected with the IRT2 probe. Thus IRT1 has a pattern of expression similar to Fe(III) chelate reductase activity, showing increased expression under iron deficiency. The pattern of IRT1 expression was also examined in two different Fe(III) chelate reductase mutants, frd1 and frd3. Plants carrying the frd1 mutation do not show an increase in Fe(III) chelate reductase activity in response to iron deficiency whereas frd3 mutants express reductase activity under both iron-sufficient and iron-deficient growth conditions (Yi, Y. (1995) Ph. D. thesis (Dartmouth College, Hanover, N.H.)). The frd1 mutant showed some expression of IRT1 in roots from plants grown on iron-sufficient plates, indicating that these plants may actually be iron-deficient. This is consistent with the chlorosis observed in this line. frd3 plants showed equally high levels of IRT1 mRNA in the roots of iron-sufficient and iron-deficient plants. This pattern of regulation is similar to that of the Fe(III) chelate reductase in this mutant and indicates that reductase activity and IRT1 expression are controlled by iron availability through a shared regulatory system.

The ability of IRT1 to suppress the mutant phenotype of a yeast strain defective for plasma membrane Fe(II) transport, together with the increased Fe(II) uptake observed in yeast expressing IRT1, demonstrates a role for this gene in uptake of iron across the plasma membrane of plant cells. Also, given the observations that IRT1 mRNA is expressed in roots, is induced by iron deprivation, an is corrugated with the plasma membrane Fe(III)-chelate reductase in wild-type and frd3 plants, the physiological role of IRT1 involves the uptake of iron from the rhizosphere across the plasma membrane in the root epidermal cell layer.

The studies described herein demonstrate that some other transition metals (Cd, Co, Mn, and Zn) are inhibitors of IRT1-mediated Fe(II) uptake in yeast and, therefore, can be substrates for this transporter.

Example 5

Construction of Transgenic Plants

A 1.4 kb NotI fragment from pIRT-1 (representing the IRT1 cDNA) was subcloned into the pCGN 18 vector in both the sense and antisense directions. The CaMV 35S promoter was used to drive expression of IRT1. After confirming the constructs in E. coli, the plasmids were transformed into Agrobacterium tumefaciens strain ASE via eletroporation. The resulting Agrobacterium strains were then used to transform Arabidopsis thaliana ecotype Columbia using the vacuum infiltration method (Bechtold et al. (1995) Gene Transfer to Plants, Potrykus and Span eds., pp.19–23 (Springer-Verlag:Berlin, Germany). Alternatively, the gene constructs could be introduced into various plant species via bombardment using a particle gun (biolistics) or by cocultivating Agrobacterium tumefaciens or Agrobacterium rhizogenes and plant cells or tissues and then regenerating transgenic plants from the transformed cells or tissues via tissue culture techniques. Seeds collected from vacuum-infiltrated plants were sown onto plates containing kanamycin. Kanamycin resistant plants were then transferred to soil and allowed to set seed. The progeny were collected from individual plants and tested for segregation of the transgenes. Families that showed 3:1 segregation of kanamycin resistance to kanamycin sensitivity were selected.

Example 6

Identification of ZRT1

Comparisons of the predicted Irt1p amino acid sequence against the current sequence databases indicated that IRT1 belongs to a family of closely related genes of unknown function, including two additional genes in A. thaliana and genes in rice, C. elegans, and humans. This comparison also identified two closely related open reading frames of unknown function from S. cerevisiae. One of these two yeast genes was designated ZRT1 for zinc-regulated transporter. The sequence of the open reading frame corresponding to ZRT1 (GenBank™ accession number P32804) was originally obtained during sequence analysis of a portion of the yeast genome (Breitwieser et al. (1993) Yeast 9:551–556). In this analysis, it was determined that ZRT1 is located on chromosome VII immediately adjacent to the FZF1 gene (FIG. 6) and is predicted to encode a protein of 376 amino acids. It has been found that Zrt1p is 30% identical and 50% similar (i.e. identities plus conservative substitutions) to Irt1p. A model of Zrt1p membrane topology suggested the presence of eight transmembrane domains located in nearly identical positions on the amino acid sequence as those predicted for Irt1p. Irt1p contains an amino acid sequence, $(-H-G-)_4$, that is a metal-binding domain. A similar sequence was also found in Zrt1p in which 3 of the 4 histidines are conserved but the fourth potential ligand is unclear. A histidine located approximately 30 amino acids toward the carboxyl terminus may contribute to metal binding. In both Irt1p and Zrt1p, this histidine-rich domain is found in a large loop between transmembrane domains 3 and 4. Topological predictions based on the "positive-inside" rule (Claros and von Heijne (1994) Comput. Appl. Biosci. 10:685–686) suggested that in both proteins this loop is located on the cytoplasmic surface of the membrane.

Example 7

ZRT1 is Required for Zinc-Limited Growth

Figure 6:
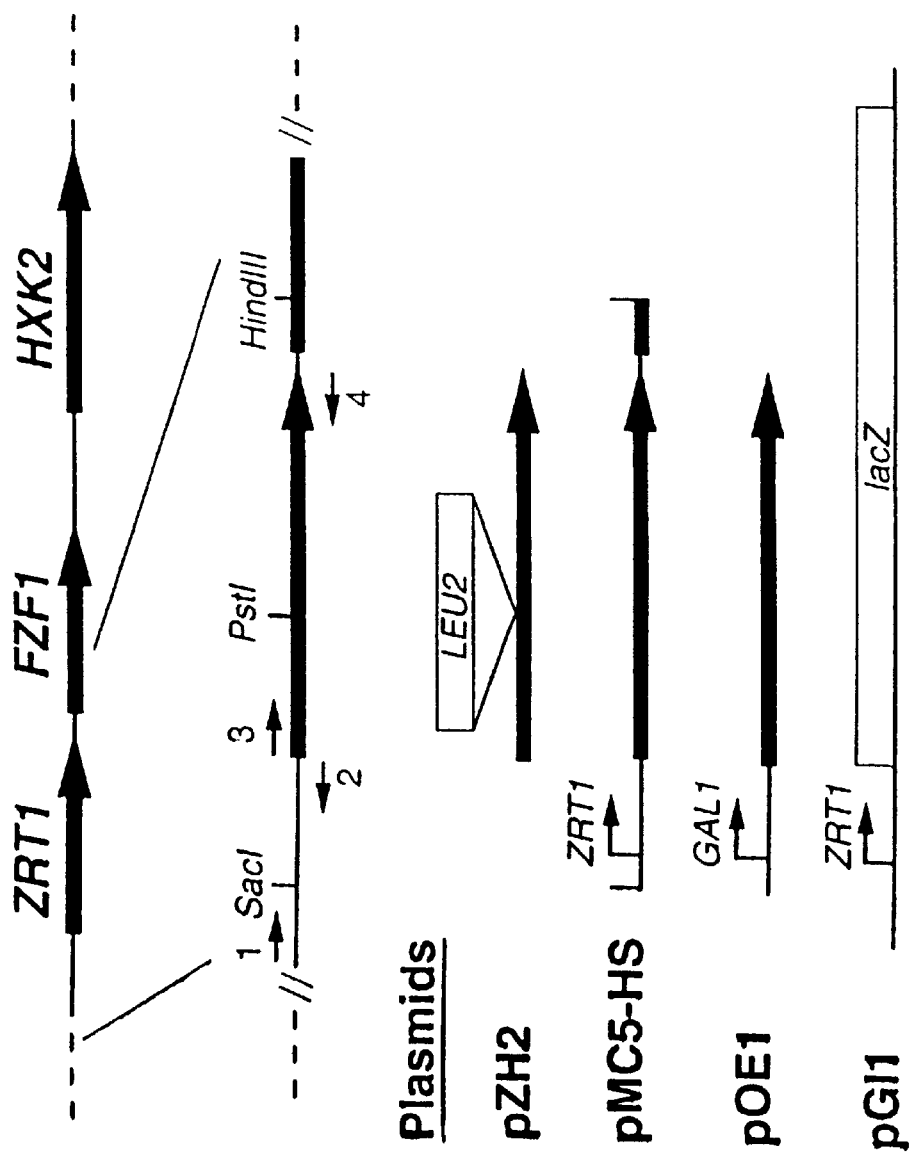
FIG. 6 depicts chromosomal region of the ZRT1 gene and plasmids constructed herein. The open reading frames on Chromosome VII are indicated by large arrows. The location of the relevant restriction sites in this region are indicated, and small arrows numbered 1–4 represent the primers used in plasmid construction. The promoters in the plasmids are identified by arrows labeled either ZRT1 or GAL1.
Figure 7:
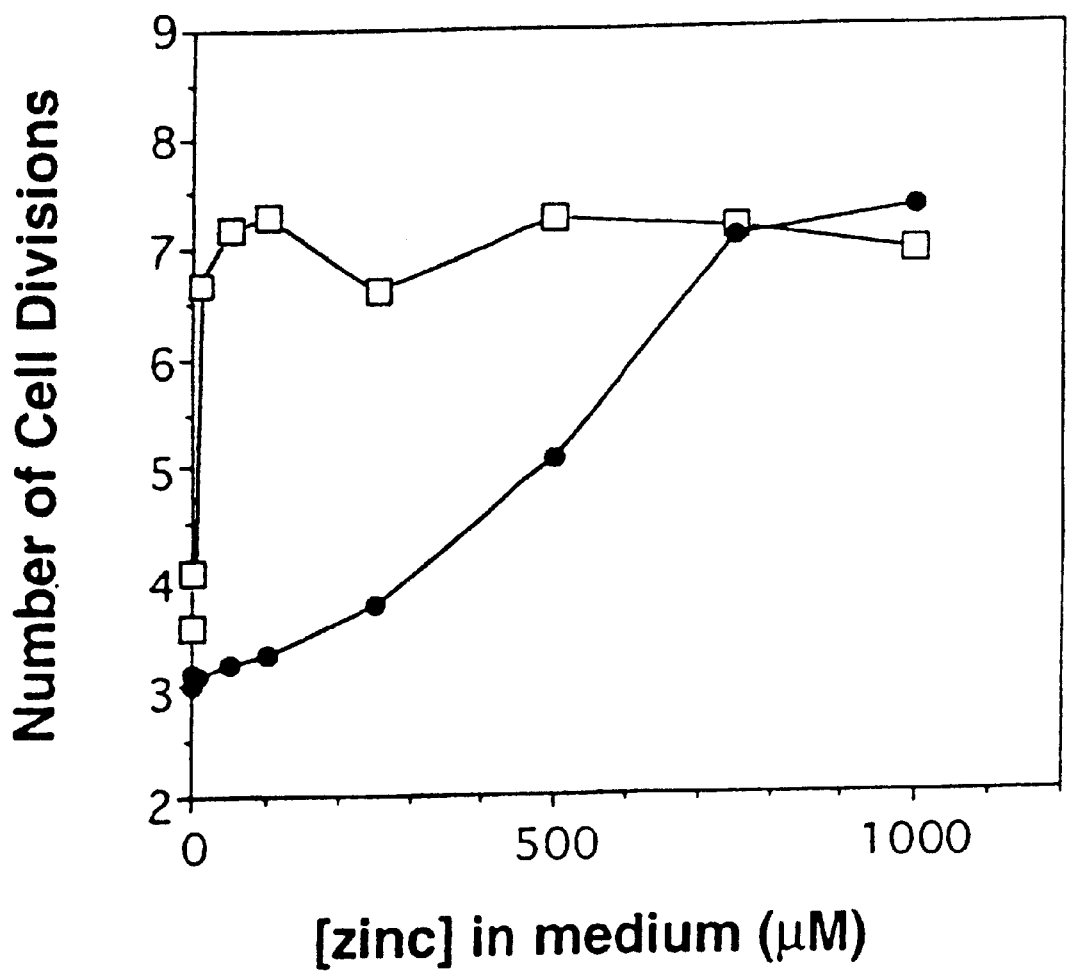
FIG. 7 is a graph depicting data which demonstrates that ZRT1 is required for zinc-limited growth. Shown are the mean values of three experiments.

To examine the function of ZRT1, a disruption mutation, zrt1::LEU2, was constructed by inserting the LEU2 gene into the center of ZRT1 (FIG. 6). This zrt1 disruption allele was then introduced into a haploid yeast strain. The resulting mutant was viable, indicating that ZRT1 is not an essential gene. Northern blot analysis failed to detect ZRT1-related mRNA in this mutant strain indicating that the disruption allele was unlikely to retain any residual function. Despite its resemblance to the Irt1p iron transporter, Zrt1p does not play a role in iron uptake in yeast. No defect was observed in iron uptake in the zrt1 mutant. However, this mutant strain did not grow in an iron-limiting medium (LIM). Because of the high EDTA concentration in LIM (1 mM), this medium is expected to have low available levels of other metals that are bound tightly by this chelator. Supplements of other metals were tested for improved growth of the zrt1 mutant in LIM. Adding 500 $\mu$M Co, Cu, Fe, Mg, or Mn to LIM had no effect on zrt1 growth, but adding 500 $\mu$M zinc greatly enhanced growth of this mutant strain. To study this effect further, a low zinc medium, LZM, was developed in which cell growth could be limited by zinc deficiency and the growth response of the wild type and zrt1 mutant strains to increasing levels of supplemented zinc was examined. Wild type (DY1457, squares) and zrt1 mutant (ZHY1, circles) cells were inoculated into LZM supplemented with the indicated amount of $ZnSO_4$ and grown for 16 hours prior to cell number determination. While growth of the wild type strain in LZM without zinc supplement was severely inhibited, adding as little as 10 $\mu$M zinc allowed this strain to go through its maximum number of seven cell divisions over a 16 hour period (FIG. 7). Mutant zrt1 cells attained this same maximum number of cell divisions only with zinc supplements of 750 $\mu$M or more, i.e. a 75-fold increase in the zinc requirement of the zrt1 mutant compared to the wild type. This growth defect could be complemented fully by the plasmid pMC5-HS (FIG. 6), a genomic clone of the ZRT1 gene, indicating that the phenotype resulted from loss of ZRT1 function and not because the mutation affected the nearby FZF1 gene on chromosome VII.

Example 8

ZRT1 is Required for High Affinity Zinc Uptake

Figure 8A:
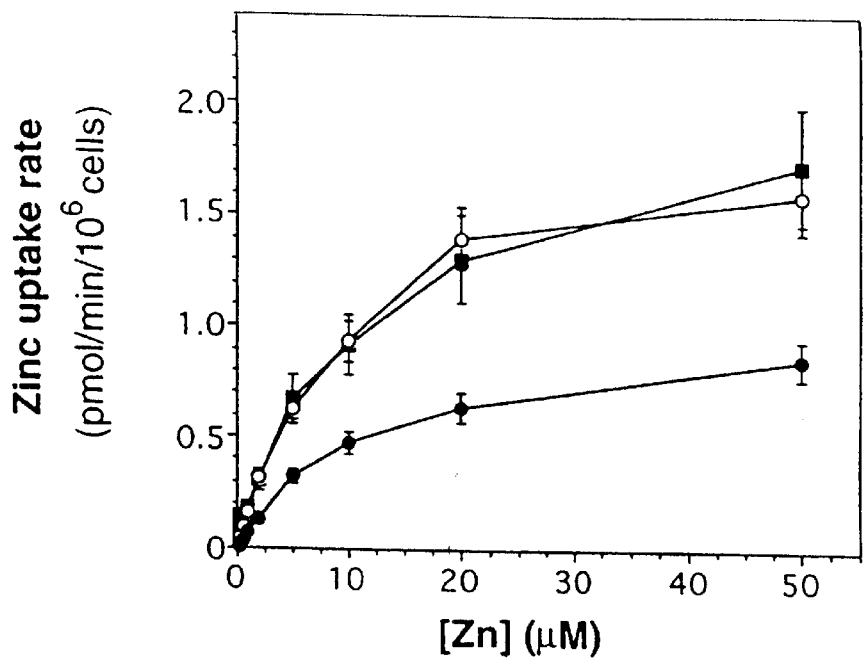
FIGS. 8A and 8B are graphs depicting data which demonstrates that ZRT1 is required for high affinity zinc uptake.
Figure 8B:
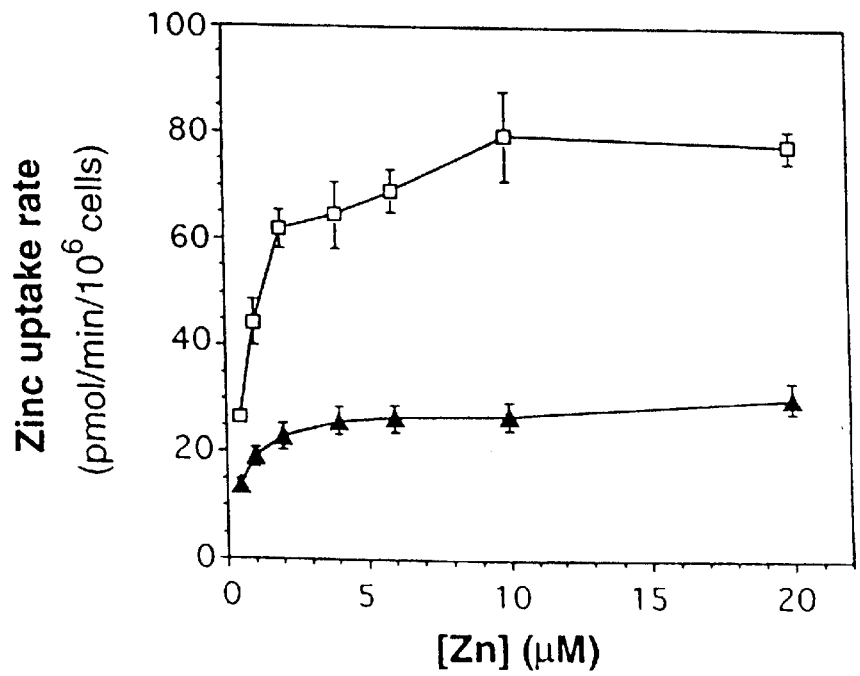

To determine if ZRT1 plays a role in zinc uptake, the biochemical properties of this process in wild type cells were first characterized. These conditions were selected on the basis of the experiment described in FIG. 10. Wild type (FIG. 10, DY1457, squares) and zrt1 mutant (FIG. 10, ZHY1, circles) cells were grown to exponential phase in zinc-limited (open symbols, FIG. 10) and zinc-replete (FIG. 10, closed symbols) media and assayed for zinc uptake rate over a range $ZnSO_4$ concentrations. Zinc-limited media was LZM+10 $\mu$M zinc for the wild type and LZM+500 $\mu$M zinc for the mutant. Zinc-replete conditions were LZM+1000 $\mu$M for both strains. ZHY1(pOE1) cells (FIG. 10, triangles) were grown in zinc-replete SDgal medium. These experiments indicated that $^{65}Zn$ uptake in the assay system is transporter-mediated; this process is time-, temperature-, and energy-dependent. At 30° C., zinc accumulation was linear with time for up to 5 minutes after which the uptake rate decreased, and little accumulation was detected with cells incubated at 0° C. or starved for glucose for one hour prior to assay. The rate of zinc uptake was concentration-dependent and saturable (FIG. 8). The Michaelis-Menten kinetic properties differed depending on the medium in which the cells were grown prior to assay. Zinc-replete cells had an apparent $K_m$ of 10±1 $\mu$M and $V_{max}$ of 2 pmol/min/$10^6$ cells (FIG. 8A, closed squares). In zinc-limited cells, the apparent $K_m$ was 1±0.1 $\mu$M and $V_{max}$ was 80 pmol/min/$10^6$ cells (FIG. 8B, open squares). Thus, uptake activity in zinc-limited cells had a markedly lower apparent $K_m$ and higher $V_{max}$ than the activity observed in zinc-replete cells.

These results demonstrate the presence of two zinc uptake systems in yeast, a high affinity system induced by zinc limitation and a low affinity system active in zinc-replete cells.

Zinc uptake assayed in zrt1 mutant cells grown in zinc-limiting and zinc-replete media displayed only low affinity activity (FIG. 8A, open and closed circles, respectively). The apparent $K_m$ in each case was 10±1 $\mu$M and the $V_{max}$ was 1–2 pmol/min/$10^6$ cells. Expressing ZRT1 from the GAL1 promoter (POE1, FIG. 6) in zinc-replete cells resulted in high affinity uptake activity (apparent $K_m$ of 0.6±0.1 $\mu$M) with a $V_{max}$ of 30 pmol/min/$10^6$ cells (FIG. 8B, triangles). No high affinity activity was observed in these cells grown in glucose, in which the GAL1 promoter is not expressed, nor in vector-only control cells grown in galactose or glucose. These results demonstrate that the ZRT1 gene is both necessary and sufficient for high affinity system activity but is not required for low affinity system activity.

Example 9

Regulation of ZRT1 mRNA Levels by Zinc

Figure 9:
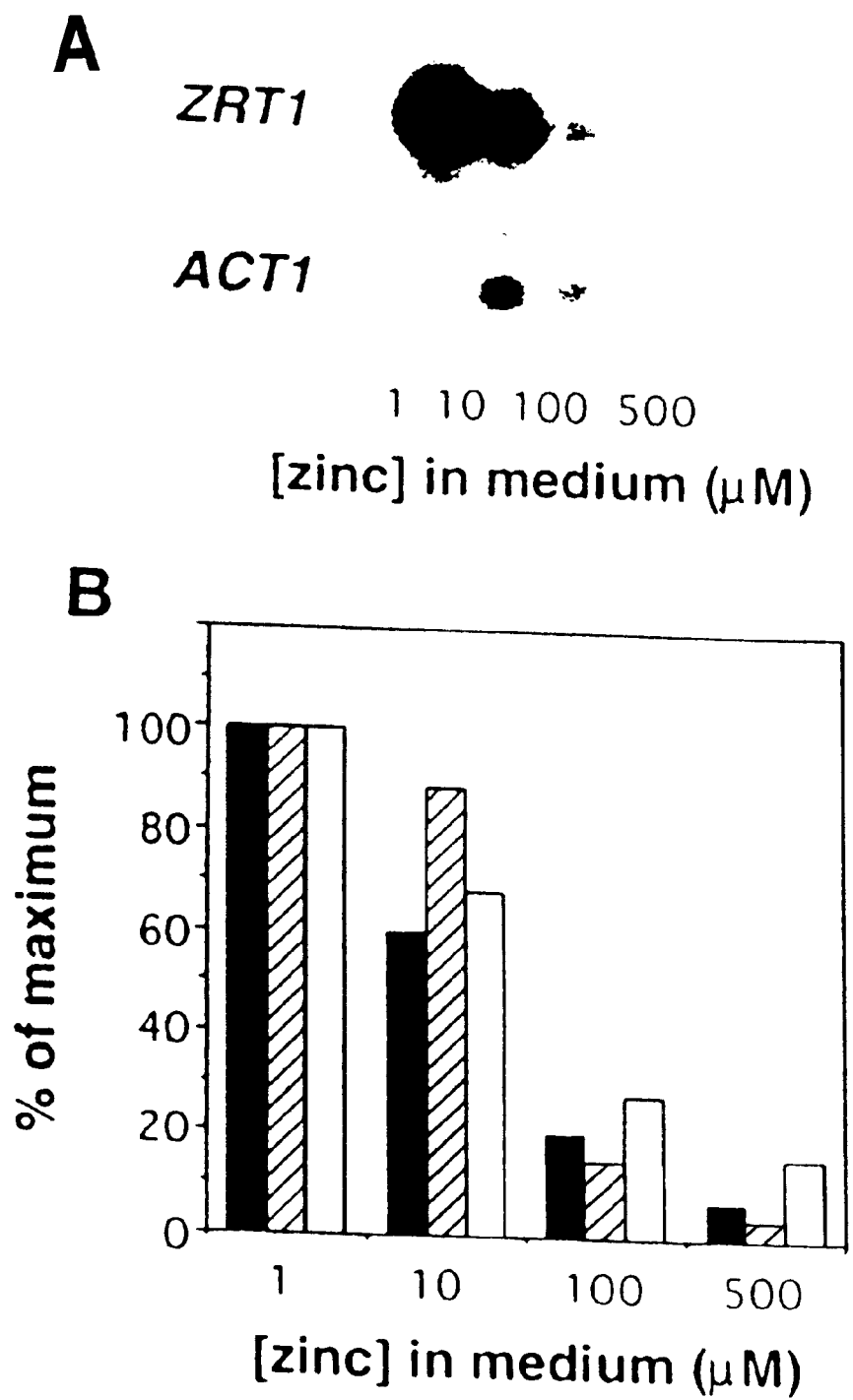

The observation that zinc-limited wild type cells possess ZRT1-dependent uptake activity absent in zinc-replete cells suggested that the ZRT1 gene could be regulated by zinc. To test this hypothesis, ZRT1 mRNA levels and zinc uptake activity were measured in cells grown in a range of zinc concentrations. To provide a simpler means of assessing ZRT1 expression, a fusion between the ZRT1 promoter and 5' untranslated region, and the *E. coli* lacZ gene encoding β-galactosidase (pGI1, FIG. 6) was also constructed. Wild type (DY1457) cells bearing pGI1 were grown to exponential phase in LZM medium supplemented with different concentrations of ZnSO$_4$. The ZRT1 mRNA levels were determined by densitometric scanning and are normalized to the total RNA loaded in each lane (closed bars), and zinc uptake (assayed at 1 $\mu$M $^{65}$Zn, hatched bars) and β-galactosidase activities (open bars) were measured. ZRT1 mRNA was regulated in a zinc-dependent manner; zinc-limited cells had 10-fold more ZRT1 mRNA than zinc-replete cells. Uptake activity of the high affinity system closely correlated with ZRT1 mRNA levels and the ZRT1-lacZ fusion was regulated in an identical manner (FIG. 9). The close correlation between ZRT1 expression levels and zinc uptake activity demonstrates that ZRT1 encodes the high affinity transporter. Furthermore, these results show that the ZRT1 gene is regulated at the transcriptional level by zinc and that the ZRT1-lacZ fusion accurately reflects that regulation.

The ZRT1-lacZ fusion allowed for comparison of ZRT1 regulation in wild type and zrt1 mutant cells grown over a range of zinc concentrations. Wild type (FIG. 10A, DY1457, open symbols) and zrt1 mutant (FIG. 10A, ZHY1, closed symbols) transformed with either pGI1 (FIG. 10A, circles) or pHYC3 (the HIS4-lacZ fusion) (FIG. 10A, triangles) were inoculated into LZM media supplemented with the indicated level of ZnSO$_4$, grown for 16 hours, and assayed for β-galactosidase activity. In a parallel experiment, these strains were grown for 16 hours in LZM media containing tracer amounts of $^{65}$Zn (FIG. 10A, squares). Cells were harvested, and cell-associated zinc was measured. In the wild type strain, β-galactosidase activity was highest in zinc-limited cells and decreased with increasing zinc concentrations in the medium (FIG. 10A). To test if zinc status alters β-galactosidase activity per se, cells bearing a HIS4-lacZ fusion were also assayed. HIS4 encodes a histidine biosynthetic enzyme and is dependent on the GCN4 leucine zipper protein for expression (Lucehini et al. (1984) *Mol. Cell. Biol.* 4:1326–1333). This promoter fusion in wild type cells generated β-galactosidase activity that correlated closely with the strain's growth response to zinc (FIG. 7). Therefore, the repressive effects of zinc on β-galactosidase activity were not caused by zinc toxicity or negative effects of zinc excess on the activity of this enzyme. To estimate the size of the intracellular zinc pool in these cells and determine its relationship to ZRT1 expression, the cell-associated zinc levels in cells grown in LZM containing $^{65}$Zn were measured. The decrease in ZRT1-dependent β-galactosidase activity coincided with an increase in cell-associated zinc.

In the zrt1 mutant strain, ZRT1-lacZ expression remained at its maximum level in cells grown with much higher concentrations of zinc in the medium than wild type (FIG. 10B). Thus, the zrt1 mutant required more zinc in the medium to repress ZRT1 expression than did wild type cells. HIS4-dependent β-galactosidase activity was similar to the growth response of this strain to zinc as well. Finally, although the response of the ZRT1-lacZ fusion to extracellular zinc levels was very different in the wild type and mutant, the response to cell-associated zinc levels was unaffected. For example, approximately equal levels of cell-associated zinc were present in wild type cells grown in LZM+50 $\mu$M zinc and zrt1 mutant cells grown in LZM+750 $\mu$M zinc, and these cells also had similar levels of ZRT1 expression. These data demonstrate that the ZRT1 gene is regulated by intracellular zinc pools and that, although the amount of zinc required in the medium to supply these pools is greatly altered in the mutant, the regulatory system that controls ZRT1 expression in response to pool size is unaffected.

The analyses described herein demonstrate that yeast has two zinc uptake systems. One system has a high affinity for substrate, is induced by zinc limitation, and is necessary for growth in zinc-limiting conditions. The ZRT1 gene encodes the transporter of this high affinity system and several lines of evidence support this hypothesis. First is the similarity between Zrt1p and Irt1p; Irt1p has been demonstrated to be an Fe(II) transporter and may also be capable of transporting zinc. Second, a mutation in the ZRT1 gene eliminated high affinity uptake activity and inhibited growth on zinc-limiting media Third, overexpressing ZRT1 increased activity of an uptake system that had an apparent $K_m$ almost identical to that of the high affinity system. These results indicate that ZRT1 expression is both necessary and sufficient for high affinity system activity. It has also been found that high affinity activity and ZRT1 expression was closely correlated across a wide range of extracellular zinc concentrations. It is formally possible that Zrt1p is only one subunit of a heteromeric transporter complex, but this is unlikely given that overexpression of ZRT1 alone increased high affinity activity.

ZRT1 is the first influx zinc transporter gene from any organism to be characterized at the molecular level. Neither Irt1p nor Zrt1p contain ATP binding domains, suggesting that uptake is driven by indirect coupling to energy metabolism, perhaps through a gradient of another ion such as K$^+$ (Fuhrmann and Rothstein (1968) *Biochim. Biophys. Acta* 163:325–330; Okorokov et al. (1983) *Biochem. Int.* 6:463–472). A group of histidine residues found in Irt1p was conserved in Zrt1p. This region is a metal-binding domain given that the imidazole ring nitrogens of histidine may serve as coordinating ligands for metal ions. In both proteins, this sequence is found in a loop region predicted to be on the cytoplasmic surface of the membrane. Similar histidine-rich sequences are also found in the three eukaryotic proteins implicated in zinc detoxification, i.e. Zrc1p, Cot1p, and Znt1p (Conklin et al. (1992) *Mol. Cell Biol.* 12:3678–3688; Kamizono et al. (1989) *Mol. Gen. Genet.* 219:161–167; Palmiter and Findley (1995) *EMBO J.* 14:639–649). In each case, the domain is predicted to be cytoplasmically located. This conservation suggests that the domain plays an important functional role in Irt1p and Zrt1p. For example, these histidines may serve as a means of feedback regulation of zinc transport. High intracellular zinc levels could result in binding of zinc by Zrt1p and reduce the activity of the transporter.

Zinc limitation induces activity of the high affinity system. Because the results show that this system is regulated at the transcriptional level, a zinc finger DNA-binding protein may sense intracellular zinc levels to regulate ZRT1 expression. However, a mechanism that controls mRNA stability through sequence elements located in the 5' untranslated region of the mRNA cannot be ruled out. Whatever the mechanism, the high affinity system is clearly regulated in response to the intracellular zinc content. This is demonstrated by the fact that the ZRT1-lacZ fusion gene shows a similar response to cell-associated zinc levels in both wild type and zrt1 mutants despite a 75-fold difference in their response to external levels of zinc. Thus, the regulatory system that controls ZRT1 expression in response to intracellular zinc pools is unaffected in the zrt1 mutant. It has also been found that zrt1 mutant is not any more resistant to high extracellular zinc levels than wild type cells. This result is consistent with the low level of ZRT1 expression observed in zinc-replete cells and demonstrates that the high affinity uptake system does not play an important role in zinc toxicity.

Example 10

Low Affinity Zinc Uptake

Zinc accumulation by the low affinity system was assayed in zrt1 mutant cells in which the high affinity system has been eliminated. Mutant zrt1 (ZHY1) cells were grown in LZM supplemented with 1 mM $ZnCl_2$. Cells were incubated with 10 $\mu$M $^{65}Zn$ for the indicated times at either 0° C. (FIG. 11, closed squares) or 30° C. (FIG. 11, open squares). Shown is a representative experiment in which each point is the average of two values, each within 15% of the mean. The low affinity system was measured in zrt1 mutant cells (FIG. 11, ZHY1, closed bars) that were grown to exponential phase in LZM supplemented with 1 mM $ZnCl_2$ and assayed for zinc uptake with 20 $\mu$M $^{65}Zn$ for five minutes in the absence (-, control) or presence of 200 $\mu$M other metals. High affinity uptake was measured in zinc-limited wild type (FIG. 11, DY1457, hatched bars) grown in LZM supplemented with 10 $\mu$M $ZnCl_2$ and assayed for zinc uptake with 2 $\mu$M $^{65}Zn$ for five minutes in the absence (-, control) or presence of 20 $\mu$M other metals. The control rate of uptake was 0.9 pmol/min/$10^6$ cells for the low affinity system and 47 pmol/min/$10^6$ cells for the high affinity system. Fe(II) was supplied in the presence of 1 mM ascorbate, a reducing agent found in control experiments to have no effect on the rate of zinc uptake by either low or high affinity systems. The asterisks indicate values significantly different from control values (P<0.05). When incubated at 0° C., these cells accumulated little zinc (FIG. 11A). At 30° C., cell-associated zinc levels increased linearly with time for up to 40 minutes. Similar results were obtained with wild type cells grown under zinc-replete conditions in which the high affinity system is not expressed. Thus, zinc accumulation by the low affinity system is time- and temperature-dependent. This accumulation was also dependent on glucose; after five minutes at 30° C. in 10 $\mu$M $^{65}Zn$, glucose-starved zrt1 cells had no detectable zinc accumulation whereas the same cells incubated with glucose accumulated 3.7 pmol/$10^6$ cells. Taken together, these data demonstrate that zinc accumulation by the low affinity system occurs through an uptake mechanism rather than by adsorption of the metal to the cell surface. To assess the substrate specificity of this system, several metals were tested for their ability to inhibit zinc uptake by zrt1 mutant cells (FIG. 11B). The concentration of the added metals in these assays was 10-fold higher (200 $\mu$M) than the radioactive zinc concentration (20 $\mu$M). The addition of excess nonradioactive zinc reduced the uptake rate of radioactive zinc to approximately 10% of the control rate. Cu and Fe(II) also inhibited zinc uptake by the low affinity system (32 and 79% of the control rate) but to a lesser extent than nonradioactive zinc (P<0.05). Co, Fe(III), Mg, Mn, and Ni did not diminish zinc uptake by the low affinity system. These results demonstrate that while Cu and Fe(II) can potentially be substrates, the low affinity system prefers zinc over other metals.

To compare the substrate specificities of the low and high affinity uptake systems, these metals were tested to determine whether they could inhibit uptake by the high affinity system under similar conditions (FIG. 11B). Again, the concentration of added metal was 10-fold higher (20 $\mu$M) than the radioactive zinc concentration (2 $\mu$M). As with the low affinity system, the high affinity system was unaffected by Co, Fe(III), Mg, Mn, and Ni whereas Fe(II), Cu, and, to a far greater extent, Zn, were inhibitory of high affinity uptake (P<0.05). In fact, the only significant difference between these systems was that Cu was more inhibitory to the low affinity system than it was to the high affinity system. These results demonstrate that the high and low affinity systems are closely related. This conclusion is supported by the high degree of sequence similarity between the Zrt1p high affinity transporter and the product of the ZRT2 gene. As described herein, the experiments demonstrate that ZRT2 encodes the low affinity zinc transporter.

Example 11

Identification of the ZRT2 Gene

The ZRT2 gene was identified as an open reading frame (ORF) of unknown function during sequence analysis of the yeast genome (GenBank™ accession number X91258). The hypothesis that ZRT2 encodes the low affinity zinc transporter was suggested by the close similarity of its predicted amino acid sequence to that of Zrt1p (Zhao and Eide (1996) *Proc. Natl. Acad. Sci.* USA 93:2454–2458). This hypothesis was further supported by the isolation of ZRT2 as a multicopy suppressor of the zinc-limited growth defect of a zrt1 mutant. Multicopy suppressors are genes that, when overexpressed due to the increased gene dosage provided by a multicopy plasmid vector, reduce the phenotypic effects of a mutation in another gene (Rine, J. (1991) *Methods Enzymol.* 194: 239–251). Overexpression of the low affinity transporter could suppress the zinc-limited growth defect of the zrt1 mutant and a multicopy plasmid containing the ZRT2 gene, pMC4, was isolated in this way. This plasmid is a weaker suppressor of the zrt1 mutation than a multicopy plasmid containing a genomic copy of ZRT1 (pMC5), i.e. pMC4 restored ability of the zrt1 mutant to grow on moderately zinc-limiting conditions but not on severely zinc-limited media where pMC5 could still complement the growth defect. This result is consistent with the 10-fold difference in apparent $K_m$ values of the high and low affinity systems.

The plasmid pMC4 contains a 9 kp insert derived from chromosome XII, immediately adjacent to the ACE2 gene (Butler and Thiele (1991) *Mol. Cell Biol.* 11:476–485). This fragment contains four ORFs originally designated L3120, L3116, L3111, and L3105 (FIG. 12). ORF L3120 is the gene that has been named ZRT2. The amino acid sequence of Zrt2p is related to that of Zrt1p and Irt1p (44% and 35% identity, respectively) (FIG. 13). All three proteins are predicted to contain eight transmembrane domains, numbered I–VIII in FIG. 13, and these domains show the greatest degree of sequence similarity among these proteins. The sequence alignment shown in FIG. 13 also indicates that transmembrane domains III and IV are separated by a region of variable length and sequence. The different lengths of this "variable region" largely accounts for the different overall sizes of these three proteins. Both Irt1p and Zrt1p contain a cluster of 3 to 4 histidine residues in the variable region that is a metal-binding domain and these histidines are also found in Zrt2p. Moreover, the variable regions of Zrt2p and Zrt1p carry a highly negative net charge. Zrt2p contains a total of 26 acidic residues in its 142 amino acid variable region (i.e., 18%) and Zrt1p contains 14 acidic residues in its 72 amino acid variable region (19%). These acidic residues could also contribute to metal binding. The membrane topologies of all three proteins, as predicted by the "positive-inside" rule (Claros and von Heijne (1994) *Comput. Appl. Biosci.* 10:685–686), show that their variable regions are located on the cytoplasmic surface of the membrane.

Example 12

ZRT2 Overexpression Increases Low Affinity Uptake

Plasmid pMC4 suppresses the growth defect of a zrt1 mutant on zinc-limited media. Given the high degree of similarity between Zrt1p and Zrt2p, this suppression was likely to result from increased expression of the ZRT2 gene and a concomitant increase in zinc uptake. To test this hypothesis, zinc uptake was assayed with yeast transformed with either pMC4 or the vector, YEp24. ZHY1 (zrt1) cells transformed with either pMC4 (closed squares) or the vector YEp24 (FIG. 14, open squares) were grown to exponential phase in SD glucose medium and assayed for zinc uptake rate over a range of $^{65}$Zn concentrations. ZHY1 (zrt1) cells transformed with pOE2 (FIG. 14, closed circles) or the vector pRS316-GAL1 (FIG. 14, open circles) were grown to exponential phase in SD galactose medium and assayed for zinc uptake over a range of $^{65}$Zn concentrations. At all concentrations tested, pMC4 transformants had an approximately 15-fold higher rate of zinc uptake than the corresponding vector control (FIG. 14). To determine if the pMC4-dependent increase in uptake rate is due to overexpression of the ZRT2 gene rather than overexpression of one of the three other ORFs present in the pMC4 insert, the ZRT2 ORF was cloned into an expression vector under control of the GAL1 promoter (pOE2, FIG. 12). This plasmid was found to suppress the zrt1 zinc-limited growth defect on galactose-containing media where the GAL1 promoter is expressed, but not on glucose-containing media where it is inactive). Cells overexpressing Zrt2p from pOP2 also had increased zinc uptake rates relative to their vector-only control (FIG. 14B). Thus, ZRT2 overexpression per se increases zinc uptake activity.

The higher uptake rate observed in ZRT2 overexpressing cells could result from increased activity of the low affinity system or increased activity of a third, previously unknown, zinc uptake system. To address this question, the Michaelis-Menten kinetic properties of the data presented in FIG. 14 were determined using Lineweaver-Burk reciprocal plots (FIG. 14, insets). Although the $V_{max}$ values are much higher in the ZRT2 overexpressing strains, the apparent $K_m$ values are very similar to those of the low affinity system measured in the corresponding vector-only controls (Table 3A).

TABLE 3

Effects of ZRT2 overexpression and disruption on the Michaelis-Menten kinetic properties of zinc uptake

| | | $K_m{}^a$ | $V_{max}{}^b$ |
|---|---|---|---|
| A. Plasmid | | | |
| pMC4 | | 8.0 ± 0.4 | 28 ± 1 |
| vector | | 9.5 ± 0.8 | 2.2 ± 0.1 |
| pOE2 | | 3.6 ± 0.1 | 17 ± 2 |
| vector | | 10 ± 1 | 2.0 ± 0.1 |
| B. Strain | Growth Medium [Zn] | | |
| wild type | low | 0.52 ± 0.07 | 76 ± 2 |
| zrt2 | low | 0.85 ± 0.18 | 60 ± 2 |
| wild type | high | 15 ± 3 | 0.60 ± 0.03 |
| zrt2 | high | 0.40 ± 0.04 | 0.31 ± 0.01 |
| zrt1 | high | 10 ± 1 | 0.52 ± 0.04 |
| zrt1zrt2 | high | N.D. | N.D. |

$^a\mu$M total zinc (mean ± SE)
$^b$pmol/min/10$^6$ (mean ± SE)
A. Kinetic analysis of the data presented in FIG. 14.
B. Kinetic analysis of the data presented in FIG. 15. Low growth medium [Zn] values were derived from the data in FIG. 15A and high growth medium [Zn] values were derived from the data in FIG. 15B. The apparent $K_m$ (in terms of [Zn]$_T$) and $V_{max}$ values were calculated from Lineweaver-Burk reciprocal plots.
N.D.- uptake not detectable.

These results show that ZRT2 overexpression increases the activity of the low affinity system. pMC4- and pOE2-dependent uptake activity was inhibited by Cu and Fe(II) to the same degree that these metals inhibited the low affinity system but not by any of the metals that do not inhibit the low affinity activity. The lower apparent $K_m$ observed in the pOE2 overexpressing strains was reproducible.

Example 13

ZRT2 is Required for Low Affinity Uptake

To determine if ZRT2 is required for the low affinity system to function, a disruption mutation in this gene was constructed. This allele, designated zrt2::HIS3, was constructed by inserting the wild type HIS3 gene into the center of the ZRT2 ORF (FIG. 13). The disruption allele was transformed by gene transplacement into wild type and zrt1 haploid strains and viable zrt2::HIS3 mutants were obtained in both. These results show that ZRT2 is not an essential gene, even in a zrt1 mutant strain where the high affinity uptake system has been eliminated.

Zinc uptake assays were performed on wild type, zrt1, zrt2, and zrt1zrt2 mutant strains to determine if the zrt2 mutation altered the activity of either the low or high affinity zinc uptake systems. Wild type (DY1457), zrt2 (ZHY2), zrt1 (ZHY1) and zrt1zrt2 (ZHY3) cells were grown to exponential phase and assayed for zinc uptake rate over a range of $^{65}$Zn concentrations. Zinc-limited cells were grown in LZM supplemented with 10 μM ZnCl$_2$ prior to assay. Zinc-replete cells were grown in LZM supplemented with 1.5 mM ZnCl$_2$ prior to assay. In zinc-limited cells, no difference in the activity of the high affinity system was observed in the zrt2 mutant relative to the wild type strain (FIG. 15A). Calculations of the apparent $K_m$ and $V_{max}$ from these data confirmed the conclusion that the zrt2 mutation does not affect the high affinity system (Table 3B). Zinc-replete wild type and zrt1 mutant cells had similar levels of low affinity activity (FIG. 15B, Table 3B). In the zrt2 single mutant, however, the low affinity system was eliminated and apparently replaced by increased activity of the high affinity system (FIG. 15B). The apparent $K_m$ of uptake in zrt2 cells was similar to the apparent $K_m$ of the high affinity system (Table 3B). Furthermore, neither low nor high affinity activity was detected in the zrt1zrt2 mutant. These results demonstrate the ZRT2 gene is required for function of the low affinity uptake system but is not necessary for high affinity activity.

Example 14

The Low Affinity System is a Relevant Source of Zinc

The presence of high affinity uptake activity in zrt2 mutants grown in a zinc-rich medium demonstrates that the low affinity system is a relevant source of zinc; these cells have increased the activity of their high affinity system to compensate for the loss of the low affinity system. The relevance of the low affinity system as a source of zinc was also indicated by the observation that the activity of this system is zinc-regulated. Mutant zrt1 cells grown in a zinc-replete medium (SD glucose) had a zinc uptake rate of 1.7 pmol/min/$10^6$ cells when assayed at 10, M $^{65}$Zn. However, cells grown in the same medium supplemented with extremely high levels of $ZnCl_2$ (2 mM) had an uptake rate only 7% (0.12 pmol/min/106 cells) of the rate observed in the untreated cells. No difference in growth rate was observed between these two culture conditions indicating that this lower activity was not due to toxic effects of the metal.

To further assess the role of the low affinity system as a source of zinc, growth of wild type and zrt2 cells in a zinc-limiting medium, LZM, supplemented with increasing amounts of zinc was examined. The same strains as in FIG. 15 were grown for six hours in SD glucose medium, harvested, washed in LZM, and reinoculated into either LZM (FIG. 15A) or LZM-EDTA (FIG. 15B) supplemented with the indicated concentrations of $ZnCl_2$ ($[Zn]_T$). These cultures were then grown for 16 hours at 30° C. prior to cell number determination. Number of cell divisions are plotted against $[Zn]_T$ and the calculated free zinc concentration ($[Zn]_F$). The metal ion buffering capacity of EDTA in LZM is exceeded at concentrations above 100 µM total zinc whereas the metal buffering capacity of citrate in LZM-EDTA maintains a linear relationship between $[Zn]T$ and $[Zn]F$ to concentrations greater than 1 mM. It has been shown previously that the zrt1 mutant requires greater than 500 µM total zinc ($[Zn]_T$) in LZM to undergo its maximum number of cell divisions and this value corresponds to a calculated free (i.e. unchelated) zinc concentration ($[Zn]_F$) of approximately 500 µM. However, no difference in zinc requirement was observed between the wild type and zrt2 strains where as little as 10 µM total zinc (~6 pM $[Zn]_F$) was sufficient for maximum growth yield (FIG. 16A). This result was expected given that the high affinity system, which would be more important than the low affinity system for zinc-limited growth, is not reduced in activity by the zrt2 mutation.

LZM is zinc-limiting because of the presence of 1 mM EDTA, a high affinity zinc chelator. The zinc requirement of the zrt1 and the zrt1zrt2 strains was determined in LZM-EDTA medium. LZM-EDTA is less zinc-limiting than LZM at a given concentration of total zinc because citrate, the predominant chelator in LZM-EDTA, binds the metal with lower affinity than EDTA. While the zrt1 single mutant divided its maximum number of times in LZM-EDTA with as little as 0.5 µM total zinc (~6 nM $[Zn]_F$), the zrt1zrt2 mutant required 500 µM total zinc (~6 µM $[Zn]_F$) to do so (FIG. 16B). Thus, zrt1zrt2 mutants are hypersensitive to zinc-limitation and require at least 1000-fold more zinc for growth than the zrt1 strain. Given that the zrt1 mutant already requires 100-fold more zinc than the wild type strain for optimal growth, this result shows that the zrt1zrt2 mutant requires greater than $10^5$-fold more zinc in the medium than the wild type strain.

The effects of the zrt2 mutation on the regulation of the ZRT1 gene was also examined. Previous studies demonstrated that ZRT1 is regulated at the transcriptional level by a regulatory pool of intracellular zinc and that ZRT1 expression increases when this pool level is low. Furthermore, cell-associated zinc levels are much lower in the zrt1 mutant grown in zinc-limiting conditions. At higher concentrations of extracellular zinc, however, these levels increased to the wild type levels. It was proposed that this accumulation was the result of zinc uptake by the low affinity system. To test this hypothesis and determine the effect of the zrt2 mutation on the pool of intracellular zinc that regulates ZRT1 gene expression, β-galactosidase activity from the ZRT1-lacZ fusion in wild type, zrt1, zrt2, and zrt1zrt2 mutant strains grown in media supplemented with a broad range of zinc concentrations was measured. The same strains as in FIG. 15 bearing the ZRT1-lacZ fusion gene (pGI1) were grown for six hours in SD glucose medium, harvested, washed in LZM, and reinoculated into either LZM (FIG. 15A) or LZM-EDTA (FIG. 15B) lacking uridine and supplemented with the indicated concentrations of $ZnCl_2$ ($[Zn]_T$). These cultures were then grown for 16 hours at 30° C. prior to being assayed for β-galactosidase activity. These values are also plotted against the calculated free zinc concentration ($[Zn]_F$). The 100% values of β-galactosidase activity were 140, 130, 86, and 105 units for wild type, zrt2, zrt1, and zrt1zrt2, respectively. ZRT1-lacZ β-galactosidase activity in the zrt2 mutant was indistinguishable from the activity in wild type cells (FIG. 17A). This result shows that ZRT1 regulation in response to the regulatory pool of intracellular zinc is not greatly altered by the zrt2 mutation. As noted previously, the high affinity system is induced in zrt2 mutants growing in zinc-rich media (FIG. 15B), yet no increase in β-galactosidase activity was observed in this experiment. This apparent contradiction can be explained by the observation that the high affinity activity observed in the zrt2 mutant is very low (i.e. only 1–2% of the maximum activity) and β-galactosidase assays may be too insensitive to reliably detect this slight increase in expression.

ZRT1-lacZ expression was greatly altered in the zrt1zrt2 strain. While β-galactosidase activity in the zrt1 mutant decreased to its minimal level with as little as 10 µM total zinc (~0.12 µM $[Zn]_F$), expression in the zrt1zrt2 mutant was down-regulated only at total zinc concentrations of 200 µM (~2.4 µM $[Zn]_F$) or higher (FIG. 17B). These results suggest that the regulatory pool of intracellular zinc is at a lower level in the zrt1zrt2 strain grown under these conditions than in the zrt1 single mutant. This conclusion was supported by measurements of cell-associated zinc in these strains. At 10 µM total zinc, cell-associated zinc in the zrt1 strain was 133±12 pmol/$10^6$ cells, compared with 5±0.6 pmol/$10^6$ cells in the zrt1zrt2 strain. At 1000 µM total zinc, the zrt1 strain had a cell-associated zinc level of 168±14 pmol/10⁶ cells and the zrt1zrt2 level rose to 86±21 pmol/10⁶ cells. Taken together, these results demonstrate that Zrt2p and the low affinity system contribute to the accumulation of zinc into the intracellular zinc pool that controls ZRT1 expression.

Previous studies suggested that at least two zinc uptake systems are present in *S. cerevisiae*. The high affinity system has an apparent $K_m$ of 1 µM total zinc which corresponds to a calculated free zinc concentration of ~10 nM. The low affinity system has an apparent $K_m$ of 10 µM total zinc which corresponds to ~100 nM free zinc. ZRT2 encodes the transporter of the low affinity system. Consistent with this hypothesis, the ZRT2 gene was isolated as a multicopy suppressor of the zinc-limited growth defect of a zrt1 mutant. Furthermore, the level of ZRT2 expression correlated with low affinity uptake activity. ZRT2 overexpression increased the activity of a system biochemically indistinguishable from the low affinity system. Conversely, disruption of the ZRT2 gene eliminated low affinity uptake. Thus, ZRT2 expression is both necessary and sufficient for low affinity activity. The predicted amino acid sequence of Zrt2p also shows that this protein plays a direct role in the transport of zinc. Zrt2p shares remarkable similarity with Zrt1p and Irt1p, an Fe(II) transporter from *A. thaliana* described herein. The distribution of hydrophobic amino acids demonstrates that all three gene products are integral membrane proteins with eight transmembrane domains. Zrt2p may be only one subunit of a heteromeric transporter complex, but this hypothesis is unlikely given that overexpression of ZRT2 alone increases zinc uptake activity.

ZRT2 is a member of a new and rapidly growing gene family of putative metal transporters. Closely related genes in organisms as diverse as fungi, plants, nematodes, and humans have been indentified. Given that three members of this family, IRT1, ZRT1, and, now, ZRT2 have been implicated in metal transport, it is likely that the other genes in this family play similar roles in metal metabolism. The structural similarity of these different gene products shows that they may use a similar mechanism to transport their substrates. Zinc uptake in yeast requires metabolic energy (White and Gadd (1987) *J. Gen. Micorbiol.* 133:727–737). Like the other members of this family, Zrt2p does not contain ATP-binding domains, nor does the protein bear any significant similarity to the ubiquitous P-type ATPase family of transport proteins. This observation shows that uptake may be driven by indirect coupling to energy metabolism, perhaps through the electrical potential generated across the plasma membrane by the plasma membrane ATPase. Alternatively, uptake may be driven by a transmembrane gradient of another ion. Uptake of zinc by the low affinity system was not inhibited by high extracellular $K^+$ (100 mM) indicating that a zinc/$K^+$ antiport mechanism, as has been previously proposed (Fuhmiann and Rothstein (1968) *Biochim. Biophys. Acta* 163;325–330; Okorokov et al. (1983) *Biochem. Int.* 6:463–472), is unlikely.

A cluster of histidines in Zrt2p is also found in Zrt1p, Irt1p, and the other members of this gene family. In Zrt2p and Zrt1p, these histidines are located in a region with a highly negative net charge due to the abundance of acidic amino acids. Imidazole ring nitrogens and carboxylate groups frequently serve as coordinating ligands for zinc (Vallee and Auld (1990) *Biochemistry* 9:5647–5659) so these amino acids may be responsible for binding the metal substrate. In all of these proteins, the histidines are found in a region between two transmembrane domains that is predicted to be exposed on the cytoplasmic face of the membrane. Given this location, these amino acids may act in a late step in the uptake process by binding the metal after it has been transported across the membrane. Alternatively, these histidines may serve as part of a feedback regulation system. High intracellular zinc levels could result in binding of zinc to Zrt2p and, by some mechanism, reduce the activity of the transporter. Whatever their role, the conservation of these histidine residues within the IRT/ZRT gene family suggests that they are critical to the function of these proteins. This conclusion is further supported by the observation that similar histidine-rich domains are found in the sequences of four transport proteins implicated in zinc detoxification, i.e. Zrc1p and Cot1p from yeast and the mammalian ZnT-1p and ZnT-2p proteins (Conklin et al. (1994) *Mol. Gen. Genet.* 244:303–311; Conklin et al. (1992) *Mol Cell Biol* 12:3678–3688; Kamizono et al. (1989) *Mol. Gen. Genet.* 219:161–167; Palmiter and Findley (1995) *EMBO J.* 14:639–649; Palmiter et al. (1996) *EMBO J.* 15:1784–1791). These proteins are apparently efflux transporters that transport metal ions from the cytoplasm either into an intracellular compartment or outside of the cell and, aside from the histidine-rich domain, share no significant similarity with the IRT/ZRT gene family. In each case, the histidine-rich domain is predicted to be cytoplasmically located. Furthermore, the interplay between zinc uptake transporters like Zrt1p and Zrt2p and efflux transporters like ZnT-1p and ZnT-2p likely plays an important role in cellular zinc homeostasis.

The results described herein demonstrate that the high and low affinity systems are genetically and biochemically separable uptake pathways. It has also been shown that the low affinity system is a relevant source of zinc for growing yeast cells. First, metal inhibition studies indicate that the low affinity system is very similar to the high affinity system in its specificity for zinc over other metals. Second, the low affinity system is the major pathway for zinc uptake in wild type cells grown in zinc-replete conditions (e.g. cells grown in SD glucose medium); no high affinity activity is detectable in these cells. Third, a zrt2 mutant strain that lacks the low affinity system has increased high affinity activity. This increased activity is presumably to compensate for loss of low affinity activity. In addition, the zrt1zrt2 mutant requires greater than 1000-fold more zinc in the medium to grow and to supply the regulatory pool of intracellular zinc and down-regulate the zinc-responsive ZRT1 promoter than does the zrt1 single mutant. These results demonstrate that the low affinity system is a major contributor to zinc accumulation in the zrt1 strain and it also contributes to wild type zinc accumulation under the same growth conditions.

Additional evidence that the low affinity system is a relevant source of zinc is provided by the observation that this system is regulated by zinc. Low affinity activity was diminished in cells grown in a medium containing extremely high levels of zinc (2 mM). The high affinity system and ZRT1 mRNA levels are regulated by zinc and this regulation is mediated at the transcriptional level in response to an intracellular zinc pool. The analysis of the low affinity system described here does not distinguish between transcriptional and post-transcriptional mechanisms. One possible mechanism, as discussed above, is down-regulation of the low affinity system by feedback inhibition of transporter activity. What is clear is that the regulatory systems that control high and low affinity uptake are responsive to very different levels of cell-associated zinc. A decrease in ZRT1 expression and high affinity activity was apparent when cell-associated zinc levels rose to as little as 30 pmol/10⁶ cells. In that same analysis, it was found that cells with a cell-associated zinc level of 120 pmol/min/10⁶ cells still had maximum low affinity activity ($V_{max}$=2 pmol/min/$10^6$ cells). Therefore, down-regulation of the low affinity system requires much higher levels of cell-associated zinc than is needed to repress the high affinity system. These observations pose an interesting regulatory question as to how these two systems respond to different levels of presumably the same signal, intracellular zinc.

It has been demonstrated herein that zrt1 mutant cells are not more resistant to higher levels of extracellular zinc than are wild type cells. Neither zrt2 nor zrt1zrt2 strains are more resistant to extracellular zinc than are the wild type or zrt1 strains. This observation is consistent with the low level of both high and low affinity activity observed in cells treated with extremely high levels of zinc and demonstrates that neither of these two systems plays a major role in zinc toxicity. Toxicity may result from zinc accumulation by one or more additional uptake pathways. The existence of this pathway(s) is demonstrated by the observation that a strain lacking both the high and low affinity systems, the zrt1zrt2 mutant, is still viable. Undoubtedly, these cells are obtaining zinc and this uptake may represent the activity of a third system for zinc accumulation. The identity of this third system is suggested by earlier studies in which zinc uptake in yeast was attributed to a "divalent cation uptake system" that was also capable of transporting Mg, Co, Mn, and Ni (Fuhrmann and Rothstein (1968) *Biochim. Biophys. Acta* 163:325–330). The apparent $K_m$ of zinc uptake by this system was estimated to be approximately 500 µM total zinc, i.e. 50- and 500-fold higher than the ZRT2- and ZRT1-dependent systems, respectively. This apparent $K_m$ is consistent with the high concentration of zinc required to confer maximum growth to the zrt1zrt2 mutant. Whatever the mechanism, given the $10^5$-fold greater zinc requirement of the zrt1zrt2 mutant strain compared to the wild type, it is unlikely that this third pathway plays a significant role in zinc accumulation under any but the most zinc-rich conditions.

Example 15

Complementation of the ZRT1 ZRT2 Strain to Identify the ZIP Genes

The zrt1 zrt$^2$ strain ZHY3 (MATαade6 can1 his3 leu2 trp1 ura3 zrt1::LEU2 zrt2::HIS3) was transformed using standard procedures with a plasmid library containing Arabidopsis cDNA inserted under the control of the phosphoglycerate kinase promoter in pFL61 (Minet et al. (1992) *Plant J.* 2(3):417–22). The poly(A)+ RNA used to construct this library was isolated from young whole seedlings (stage two leaves). The transformants were plated onto SD glucose medium plus adenine histidine, leucine, and tryptophan (i.e., uridine). 300,000 Ura+ transformants were screened and cells giving rise to large colonies were selected for further analysis.

Example 16

Preparation of Antibodies Against an IRT1 Peptide

A peptide was synthesized which spans amino acids 162 through 184 of IRT1: Acetyl-C-PANDVTLPIKEDDSN-amide (SEQ ID NO:21) (Quality Controlled Biochemicals, Inc.). This peptide was then used as an antigen to raise polyclonal antibodies in rabbits (Quality Controlled Biochemicals, Inc.). A western blot of total protein prepared from Arabidopsis demonstrated that the antibodies recognize a protein of approximately 33 KDa which is only present in iron-starved plants. These antibodies have been further affinity-purified.

Example 17

Zinc Uptake by ZIPs

Using the standard Zn uptake assay described above, there is essentially no detectable zinc uptake (5 minute time course using 10 mM Zn) by the zrt1zrt2 double mutant strain, ZHY3. The same strain, ZHY3, containing the ZIP1 gene has a Zn uptake rate of 191 fmol/min/$10^6$ cells. ZIP3 containing cells have a Zn uptake rate of 134 fmol/min/$10^6$ cells. Cells containing ZIP2 show no Zn uptake under these conditions.

Equivalents

Those skilled in the art will be able to recognize, or be able to ascertain using no more than routine experimentation, numerous equivalents to the specific procedures described herein. Such equivalents are considered to be within the scope of this invention and are covered by the following claims.

What is claimed is:

1. A transgenic plant or transgenic plant portion thereof which expresses a polypeptide comprising an amino acid sequence, wherein said amino acid sequence has at least 70% sequence identity with SEQ ID NO:2 and wherein said amino acid sequence has Fe(II) uptake activity.

2. The transgenic plant or transgenic plant portion thereof of claim 1, wherein said plant or portion thereof is selected from the group consisting of rice, beans, peas and maize.

3. The transgenic plant or transgenic plant portion thereof of claim 1, wherein said amino acid sequence is SEQ ID NO:2.

4. The transgenic plant or transgenic plant portion thereof of claim 1, wherein said amino acid sequence is encoded by a nucleotide sequence which has at least 70% sequence identity to a nucleotide sequence of SEQ ID NO:1.

5. The transgenic plant or transgenic plant portion thereof of claim 1, wherein said amino acid sequence is encoded by a nucleotide sequence of SEQ ID NO:1.

6. A composition comprising the transgenic plant or transgenic plant portion thereof of claim 1.

7. The composition of claim 6, wherein said composition is a human or animal supplement.

8. The composition of claim 6, further comprising a pharmaceutically acceptable carrier.

* * * * *

SEQUENCE LISTING

```
<160> NUMBER OF SEQ ID NOS: 27

<210> SEQ ID NO 1
<211> LENGTH: 1329
<212> TYPE: DNA
<213> ORGANISM: Arabidopsis thaliana
<220> FEATURE:
<221> NAME/KEY: CDS
<222> LOCATION: (18)..(1034)

<400> SEQUENCE: 1
caaattcagc acttctc atg aaa aca atc ttc ctc gta ctc att ttt gtc         50
                  Met Lys Thr Ile Phe Leu Val Leu Ile Phe Val
                    1               5                  10 tct ttt gca atc tct cca gca act tca act gcg ccg gaa gaa tgt gga        98
Ser Phe Ala Ile Ser Pro Ala Thr Ser Thr Ala Pro Glu Glu Cys Gly
            15                  20                  25
```

```
agc gag tca gcg aac ccg tgc gtc aac aaa gct aaa gct ttg cct ctc     146
Ser Glu Ser Ala Asn Pro Cys Val Asn Lys Ala Lys Ala Leu Pro Leu
         30                  35                  40 aaa gtc ata gca atc ttc gta atc ctc att gca agc atg att ggt gtt     194
Lys Val Ile Ala Ile Phe Val Ile Leu Ile Ala Ser Met Ile Gly Val
 45                  50                  55 gga gct cct ctc ttt agc cgt aac gtt tcg ttc ctc caa cca gac gga     242
Gly Ala Pro Leu Phe Ser Arg Asn Val Ser Phe Leu Gln Pro Asp Gly
 60                  65                  70                  75 aac atc ttc act atc att aag tgt ttc gcc tcc ggg atc atc ctt gga     290
Asn Ile Phe Thr Ile Ile Lys Cys Phe Ala Ser Gly Ile Ile Leu Gly
                 80                  85                  90 acc ggt ttt atg cac gtt tta cct gat tct ttc gaa atg ttg tca tct     338
Thr Gly Phe Met His Val Leu Pro Asp Ser Phe Glu Met Leu Ser Ser
             95                 100                 105 ata tgt ctt gaa gag aac ccg tgg cat aaa ttt cct ttc tcc gga ttt     386
Ile Cys Leu Glu Glu Asn Pro Trp His Lys Phe Pro Phe Ser Gly Phe
         110                 115                 120 ctc gct atg tta tcg ggt cta atc act cta gcc att gac tcc atg gcc     434
Leu Ala Met Leu Ser Gly Leu Ile Thr Leu Ala Ile Asp Ser Met Ala
     125                 130                 135 acg agc cta tac acc agc aag aac gca gtt ggt atc atg ccc cat ggt     482
Thr Ser Leu Tyr Thr Ser Lys Asn Ala Val Gly Ile Met Pro His Gly
140                 145                 150                 155 cat ggt cat ggt cac ggc ccc gca aat gat gtt acc tta cca ata aaa     530
His Gly His Gly His Gly Pro Ala Asn Asp Val Thr Leu Pro Ile Lys
                 160                 165                 170 gaa gat gat tcg tca aat gca cag ctc ttg cga tac cga gtc att gcc     578
Glu Asp Asp Ser Ser Asn Ala Gln Leu Leu Arg Tyr Arg Val Ile Ala
             175                 180                 185 atg gtc ttg gaa ctt ggg atc ata gtt cac tcg gtg gtc att gga tta     626
Met Val Leu Glu Leu Gly Ile Ile Val His Ser Val Val Ile Gly Leu
         190                 195                 200 tct cta gga gca act agt gac act tgc acc att aaa gga ctt ata gca     674
Ser Leu Gly Ala Thr Ser Asp Thr Cys Thr Ile Lys Gly Leu Ile Ala
     205                 210                 215 gct ctt tgc ttc cat caa atg ttc gaa ggc atg ggt ctt ggc ggt tgt     722
Ala Leu Cys Phe His Gln Met Phe Glu Gly Met Gly Leu Gly Gly Cys
220                 225                 230                 235 atc ctc cag gct gag tat aca aat atg aag aaa ttt gtt atg gcg ttc     770
Ile Leu Gln Ala Glu Tyr Thr Asn Met Lys Lys Phe Val Met Ala Phe
                 240                 245                 250 ttt ttc gcg gta aca aca cca ttc gga ata gcg tta ggg atc gct cta     818
Phe Phe Ala Val Thr Thr Pro Phe Gly Ile Ala Leu Gly Ile Ala Leu
             255                 260                 265 tca act gtt tac caa gat aat agc cca aaa gct ttg atc acg gtt gga     866
Ser Thr Val Tyr Gln Asp Asn Ser Pro Lys Ala Leu Ile Thr Val Gly
         270                 275                 280 ctt cta aat gca tgc tcc gct gga ttg ctc att tac atg gca ctc gtg     914
Leu Leu Asn Ala Cys Ser Ala Gly Leu Leu Ile Tyr Met Ala Leu Val
     285                 290                 295 gat ctt cta gct gcg gag ttc atg gga cct aag ctt caa ggt agc atc     962
Asp Leu Leu Ala Ala Glu Phe Met Gly Pro Lys Leu Gln Gly Ser Ile
300                 305                 310                 315 aaa atg cag ttc aag tgt tta atc gcg gct ctt ctc ggg tgc ggt gga    1010
Lys Met Gln Phe Lys Cys Leu Ile Ala Ala Leu Leu Gly Cys Gly Gly
                 320                 325                 330 atg tcg att atc gcc aaa tgg gct taactaatac tccagatatt gcggaattga    1064
Met Ser Ile Ile Ala Lys Trp Ala
```

-continued

```
           335
aatcatgtgg atttcattat cgaactaaaa ccgttttagg tttacgtctc gattctctat     1124
cggtttttta tcttctctta caaaagattt gcgtggatct atcacatttt aaggaacatg     1184
tcttttggta gatatgtaaa tgtgataggc cccacgattc atagttttct tttgtatctt     1244
cctttatttt gtcaaggcag tatagttcat atcgtgtaat gttttttgcat ctcatataaa    1304 taaataaaac ttttgctgct ttttc                                           1329
```

<210> SEQ ID NO 2
<211> LENGTH: 339
<212> TYPE: PRT
<213> ORGANISM: Arabidopsis thaliana

<400> SEQUENCE: 2

```
Met Lys Thr Ile Phe Leu Val Leu Ile Phe Val Ser Phe Ala Ile Ser
  1               5                  10                  15

Pro Ala Thr Ser Thr Ala Pro Glu Glu Cys Gly Ser Glu Ser Ala Asn
                 20                  25                  30

Pro Cys Val Asn Lys Ala Lys Ala Leu Pro Leu Lys Val Ile Ala Ile
             35                  40                  45

Phe Val Ile Leu Ile Ala Ser Met Ile Gly Val Gly Ala Pro Leu Phe
         50                  55                  60

Ser Arg Asn Val Ser Phe Leu Gln Pro Asp Gly Asn Ile Phe Thr Ile
 65                  70                  75                  80

Ile Lys Cys Phe Ala Ser Gly Ile Ile Leu Gly Thr Gly Phe Met His
                 85                  90                  95

Val Leu Pro Asp Ser Phe Glu Met Leu Ser Ser Ile Cys Leu Glu Glu
            100                 105                 110

Asn Pro Trp His Lys Phe Pro Phe Ser Gly Phe Leu Ala Met Leu Ser
            115                 120                 125

Gly Leu Ile Thr Leu Ala Ile Asp Ser Met Ala Thr Ser Leu Tyr Thr
        130                 135                 140

Ser Lys Asn Ala Val Gly Ile Met Pro His Gly His Gly His Gly His
145                 150                 155                 160

Gly Pro Ala Asn Asp Val Thr Leu Pro Ile Lys Glu Asp Asp Ser Ser
                165                 170                 175

Asn Ala Gln Leu Leu Arg Tyr Arg Val Ile Ala Met Val Leu Glu Leu
            180                 185                 190

Gly Ile Ile Val His Ser Val Ile Gly Leu Ser Leu Gly Ala Thr
            195                 200                 205

Ser Asp Thr Cys Thr Ile Lys Gly Leu Ile Ala Ala Leu Cys Phe His
    210                 215                 220

Gln Met Phe Glu Gly Met Gly Leu Gly Gly Cys Ile Leu Gln Ala Glu
225                 230                 235                 240

Tyr Thr Asn Met Lys Lys Phe Val Met Ala Phe Phe Ala Val Thr
                245                 250                 255

Thr Pro Phe Gly Ile Ala Leu Gly Ile Ala Leu Ser Thr Val Tyr Gln
            260                 265                 270

Asp Asn Ser Pro Lys Ala Leu Ile Thr Val Gly Leu Leu Asn Ala Cys
        275                 280                 285

Ser Ala Gly Leu Leu Ile Tyr Met Ala Leu Val Asp Leu Leu Ala Ala
    290                 295                 300

Glu Phe Met Gly Pro Lys Leu Gln Gly Ser Ile Lys Met Gln Phe Lys
305                 310                 315                 320
```

```
Cys Leu Ile Ala Ala Leu Leu Gly Cys Gly Gly Met Ser Ile Ile Ala
            325                 330                 335
Lys Trp Ala

<210> SEQ ID NO 3
<211> LENGTH: 1215
<212> TYPE: DNA
<213> ORGANISM: Arabidopsis thaliana
<220> FEATURE:
<221> NAME/KEY: CDS
<222> LOCATION: (42)..(1106)

<400> SEQUENCE: 3
cagtgtgagt aatttagcaa gaacataaat atcttaaact c atg tct gaa tgt gga      56
                                            Met Ser Glu Cys Gly
                                              1               5 tgt ttt tcg gca aca act atg ttg aga att tgt gta gta ttg ata ata       104
Cys Phe Ser Ala Thr Thr Met Leu Arg Ile Cys Val Val Leu Ile Ile
                 10                  15                  20 tgt ttg cat atg tgt tgt gcc tcg agt gat tgt aca agt cac gat gat       152
Cys Leu His Met Cys Cys Ala Ser Ser Asp Cys Thr Ser His Asp Asp
             25                  30                  35 cct gtg tct caa gac gaa gca gag aaa gcg acg aag cta aag ctt ggt       200
Pro Val Ser Gln Asp Glu Ala Glu Lys Ala Thr Lys Leu Lys Leu Gly
         40                  45                  50 tcg ata gct tta ctt ctt gta gcc gga gga gtc ggc gtg agt cta ccg       248
Ser Ile Ala Leu Leu Leu Val Ala Gly Gly Val Gly Val Ser Leu Pro
     55                  60                  65 ttg atc ggg aaa agg att ccg gcg tta caa ccg gaa aat gat atc ttc       296
Leu Ile Gly Lys Arg Ile Pro Ala Leu Gln Pro Glu Asn Asp Ile Phe
 70                  75                  80                  85 ttc atg gtg aaa gct ttt gct gca gga gtg atc ctc tgc aca ggt ttc       344
Phe Met Val Lys Ala Phe Ala Ala Gly Val Ile Leu Cys Thr Gly Phe
                 90                  95                 100 gtt cat atc tta cca gac gcg ttc gag aga ttg agc tct cca tgt ctt       392
Val His Ile Leu Pro Asp Ala Phe Glu Arg Leu Ser Ser Pro Cys Leu
            105                 110                 115 gag gac act aca gct ggg aag ttc ccg ttt gct ggt ttt gta gcg atg       440
Glu Asp Thr Thr Ala Gly Lys Phe Pro Phe Ala Gly Phe Val Ala Met
        120                 125                 130 ctg tcg gcg atg ggg act ctt atg atc gac aca ttc gcg aca ggg tat       488
Leu Ser Ala Met Gly Thr Leu Met Ile Asp Thr Phe Ala Thr Gly Tyr
    135                 140                 145 tac aag agg caa cat ttt agc aat aac cat ggg agc aag caa gtg aac       536
Tyr Lys Arg Gln His Phe Ser Asn Asn His Gly Ser Lys Gln Val Asn
150                 155                 160                 165 gta gta gta gat gaa gaa gag cat gcg ggt cat gtt cac att cac acg       584
Val Val Val Asp Glu Glu Glu His Ala Gly His Val His Ile His Thr
                170                 175                 180 cac gct agt cac gga cac aca cat ggt tcg acc gag ttg atc aga aga       632
His Ala Ser His Gly His Thr His Gly Ser Thr Glu Leu Ile Arg Arg
            185                 190                 195 cgt ata gtg tcg cag gtg ctt gag att ggg ata gtt gtg cat tcg gtt       680
Arg Ile Val Ser Gln Val Leu Glu Ile Gly Ile Val Val His Ser Val
        200                 205                 210 att ata ggg ata tca ctt gga gct tca cag agc ata gac acc ata aag       728
Ile Ile Gly Ile Ser Leu Gly Ala Ser Gln Ser Ile Asp Thr Ile Lys
    215                 220                 225 cca ctc atg gct gca cta tct ttc cat cag ttc ttt gaa ggt ctt ggc       776
Pro Leu Met Ala Ala Leu Ser Phe His Gln Phe Phe Glu Gly Leu Gly
```

```
                230                 235                 240                 245
ctc ggt gga tgc atc tcc ctg gcg gat atg aag tcg aaa tcg aca gtg        824
Leu Gly Gly Cys Ile Ser Leu Ala Asp Met Lys Ser Lys Ser Thr Val
                250                 255                 260 cta atg gcg aca ttt ttc tcg gtg acg gcg cca ctt ggg ata gga ata        872
Leu Met Ala Thr Phe Phe Ser Val Thr Ala Pro Leu Gly Ile Gly Ile
                265                 270                 275 ggg ttg ggg atg tca agt ggt tta ggc tac agg aaa gag agc aaa gag        920
Gly Leu Gly Met Ser Ser Gly Leu Gly Tyr Arg Lys Glu Ser Lys Glu
                280                 285                 290 gca ata atg gtg gaa gga atg ttg aat gct gca tct gct ggg ata ctc        968
Ala Ile Met Val Glu Gly Met Leu Asn Ala Ala Ser Ala Gly Ile Leu
                295                 300                 305 ata tac atg tca ctt gtt gat ctt ctt gct act gat ttt atg aat cca       1016
Ile Tyr Met Ser Leu Val Asp Leu Leu Ala Thr Asp Phe Met Asn Pro
310                 315                 320                 325 aga ttg caa tcc aat ctc tgg ctt cac ttg gct gct tat ctc tct ctc       1064
Arg Leu Gln Ser Asn Leu Trp Leu His Leu Ala Ala Tyr Leu Ser Leu
                330                 335                 340 gtc cta ggc gca ggt tcc atg tct ctc ctc gcc atc tgg gcc               1106
Val Leu Gly Ala Gly Ser Met Ser Leu Leu Ala Ile Trp Ala
                345                 350                 355 tgattcttga tctgaaacta acaaacaaac aaaccaaatg ccgctctttt ttctcaaatc     1166
tgtaatggtg tttctaatct cagaatcaat actattctat cttgaacac                1215

<210> SEQ ID NO 4
<211> LENGTH: 355
<212> TYPE: PRT
<213> ORGANISM: Arabidopsis thaliana

<400> SEQUENCE: 4

Met Ser Glu Cys Gly Cys Phe Ser Ala Thr Thr Met Leu Arg Ile Cys
  1               5                  10                  15

Val Val Leu Ile Ile Cys Leu His Met Cys Cys Ala Ser Ser Asp Cys
                 20                  25                  30

Thr Ser His Asp Asp Pro Val Ser Gln Asp Glu Ala Glu Lys Ala Thr
             35                  40                  45

Lys Leu Lys Leu Gly Ser Ile Ala Leu Leu Leu Val Ala Gly Gly Val
         50                  55                  60

Gly Val Ser Leu Pro Leu Ile Gly Lys Arg Ile Pro Ala Leu Gln Pro
 65                  70                  75                  80

Glu Asn Asp Ile Phe Phe Met Val Lys Ala Phe Ala Ala Gly Val Ile
                 85                  90                  95

Leu Cys Thr Gly Phe Val His Ile Leu Pro Asp Ala Phe Glu Arg Leu
            100                 105                 110

Ser Ser Pro Cys Leu Glu Asp Thr Thr Ala Gly Lys Phe Pro Phe Ala
        115                 120                 125

Gly Phe Val Ala Met Leu Ser Ala Met Gly Thr Leu Met Ile Asp Thr
    130                 135                 140

Phe Ala Thr Gly Tyr Tyr Lys Arg Gln His Phe Ser Asn Asn His Gly
145                 150                 155                 160

Ser Lys Gln Val Asn Val Val Asp Glu Glu His Ala Gly His
                165                 170                 175

Val His Ile His Thr His Ala Ser His Gly His Thr His Gly Ser Thr
            180                 185                 190

Glu Leu Ile Arg Arg Arg Ile Val Ser Gln Val Leu Glu Ile Gly Ile
```

```
                195                 200                 205
Val Val His Ser Val Ile Ile Gly Ile Ser Leu Gly Ala Ser Gln Ser
        210                 215                 220

Ile Asp Thr Ile Lys Pro Leu Met Ala Ala Leu Ser Phe His Gln Phe
225                 230                 235                 240

Phe Glu Gly Leu Gly Leu Gly Gly Cys Ile Ser Leu Ala Asp Met Lys
                245                 250                 255

Ser Lys Ser Thr Val Leu Met Ala Thr Phe Phe Ser Val Thr Ala Pro
                260                 265                 270

Leu Gly Ile Gly Ile Gly Leu Gly Met Ser Ser Gly Leu Gly Tyr Arg
                275                 280                 285

Lys Glu Ser Lys Glu Ala Ile Met Val Glu Gly Met Leu Asn Ala Ala
                290                 295                 300

Ser Ala Gly Ile Leu Ile Tyr Met Ser Leu Val Asp Leu Leu Ala Thr
305                 310                 315                 320

Asp Phe Met Asn Pro Arg Leu Gln Ser Asn Leu Trp Leu His Leu Ala
                325                 330                 335

Ala Tyr Leu Ser Leu Val Leu Gly Ala Gly Ser Met Ser Leu Leu Ala
                340                 345                 350

Ile Trp Ala
        355

<210> SEQ ID NO 5
<211> LENGTH: 1061
<212> TYPE: DNA
<213> ORGANISM: Arabidopsis thaliana
<220> FEATURE:
<221> NAME/KEY: CDS
<222> LOCATION: (1)..(1059)

<400> SEQUENCE: 5 atg gct ttg tct tcc aaa acc cta aag tca act ctc gtc ttc ctc tct       48
Met Ala Leu Ser Ser Lys Thr Leu Lys Ser Thr Leu Val Phe Leu Ser
 1               5                  10                  15 att att ttc ctc tgt ttc tcc ttg atc cta gct cac ggc ggc ata gac       96
Ile Ile Phe Leu Cys Phe Ser Leu Ile Leu Ala His Gly Gly Ile Asp
                20                  25                  30 gac ggc gac gaa gaa gag gag acc aac cag cca cct ccg gcc acc gga      144
Asp Gly Asp Glu Glu Glu Glu Thr Asn Gln Pro Pro Pro Ala Thr Gly
            35                  40                  45 aca acc acc gtc gtg aat ctc cga tcc aaa ggc ttg gtg ctt gtg aag      192
Thr Thr Thr Val Val Asn Leu Arg Ser Lys Gly Leu Val Leu Val Lys
     50                  55                  60 atc tac tgt att ata ata ctc ttc ttt agc aca ttc tta gcc gga att      240
Ile Tyr Cys Ile Ile Ile Leu Phe Phe Ser Thr Phe Leu Ala Gly Ile
 65                  70                  75                  80 tca cct tac ttt tac cga tgg aac gag tcg ttt ctc ctc cta gga act      288
Ser Pro Tyr Phe Tyr Arg Trp Asn Glu Ser Phe Leu Leu Leu Gly Thr
                 85                  90                  95 caa ttc tcc ggt ggt ata ttc ctc gcg acc gct cta atc cat ttc ctc      336
Gln Phe Ser Gly Gly Ile Phe Leu Ala Thr Ala Leu Ile His Phe Leu
                100                 105                 110 agc gac gct aac gag act ttc cga ggg tta aaa cac aaa gag tat cct      384
Ser Asp Ala Asn Glu Thr Phe Arg Gly Leu Lys His Lys Glu Tyr Pro
            115                 120                 125 tac gct ttc atg tta gca gcc gct gga tat tgc ctt aca atg ctg gca      432
Tyr Ala Phe Met Leu Ala Ala Ala Gly Tyr Cys Leu Thr Met Leu Ala
        130                 135                 140
```

-continued

```
gat gtg gcg gtt gcg ttt gta gcg gct ggg agt aat aac aac cac gtc         480
Asp Val Ala Val Ala Phe Val Ala Ala Gly Ser Asn Asn Asn His Val
145                 150                 155                 160 gga gct agc gtc gga gag tcg agg gag gat gat gac gtg gca gtg aaa         528
Gly Ala Ser Val Gly Glu Ser Arg Glu Asp Asp Asp Val Ala Val Lys
            165                 170                 175 gag gaa gga cgt cgt gag ata aag agt ggt gtt gat gtg agt caa gcg         576
Glu Glu Gly Arg Arg Glu Ile Lys Ser Gly Val Asp Val Ser Gln Ala
        180                 185                 190 ctt ata cga act agt gga ttt gga gac aca gct ttg ctg att ttt gct         624
Leu Ile Arg Thr Ser Gly Phe Gly Asp Thr Ala Leu Leu Ile Phe Ala
    195                 200                 205 ctt tgt ttt cac tcc atc ttt gag gga atc gcc att ggt ctc tca gac         672
Leu Cys Phe His Ser Ile Phe Glu Gly Ile Ala Ile Gly Leu Ser Asp
210                 215                 220 act aaa agc gac gct tgg aga aac cta tgg aca ata tcg ttg cac aag         720
Thr Lys Ser Asp Ala Trp Arg Asn Leu Trp Thr Ile Ser Leu His Lys
225                 230                 235                 240 gtc ttt gcg gcc gta gca atg gga ata gct ctt ctc aag cta atc cct         768
Val Phe Ala Ala Val Ala Met Gly Ile Ala Leu Leu Lys Leu Ile Pro
            245                 250                 255 aaa cgt cca ttc ttc ctc act gtc gtc tac tcc ttc gcc ttt ggg ata         816
Lys Arg Pro Phe Phe Leu Thr Val Val Tyr Ser Phe Ala Phe Gly Ile
        260                 265                 270 tcg agt ccc ata ggt gtc ggg att ggc att gga atc aat gcc act agc         864
Ser Ser Pro Ile Gly Val Gly Ile Gly Ile Gly Ile Asn Ala Thr Ser
    275                 280                 285 caa gga gct ggt ggt gac tgg acc tac gcg atc tct atg ggg ctt gcg         912
Gln Gly Ala Gly Gly Asp Trp Thr Tyr Ala Ile Ser Met Gly Leu Ala
290                 295                 300 tgt gga gtt ttt gtg tac gtt gcg gtt aac cat ctc atc tca aaa ggg         960
Cys Gly Val Phe Val Tyr Val Ala Val Asn His Leu Ile Ser Lys Gly
305                 310                 315                 320 tat aag cct ctt gag gaa tgt tac ttc gac aag cca atc tac aag ttt        1008
Tyr Lys Pro Leu Glu Glu Cys Tyr Phe Asp Lys Pro Ile Tyr Lys Phe
            325                 330                 335 att gcc gtc ttc ctc ggt gtt gct ttg ctc tct gtt gta atg att tgg        1056
Ile Ala Val Phe Leu Gly Val Ala Leu Leu Ser Val Val Met Ile Trp
        340                 345                 350 gat tg                                                                  1061
Asp <210> SEQ ID NO 6
<211> LENGTH: 353
<212> TYPE: PRT
<213> ORGANISM: Arabidopsis thaliana

<400> SEQUENCE: 6

Met Ala Leu Ser Ser Lys Thr Leu Lys Ser Thr Leu Val Phe Leu Ser
  1               5                  10                  15

Ile Ile Phe Leu Cys Phe Ser Leu Ile Leu Ala His Gly Gly Ile Asp
             20                  25                  30

Asp Gly Asp Glu Glu Glu Glu Thr Asn Gln Pro Pro Ala Thr Gly
         35                  40                  45

Thr Thr Thr Val Val Asn Leu Arg Ser Lys Gly Leu Val Leu Val Lys
     50                  55                  60

Ile Tyr Cys Ile Ile Ile Leu Phe Phe Ser Thr Phe Leu Ala Gly Ile
 65                  70                  75                  80

Ser Pro Tyr Phe Tyr Arg Trp Asn Glu Ser Phe Leu Leu Leu Gly Thr
```

-continued

```
                    85                  90                  95
Gln Phe Ser Gly Gly Ile Phe Leu Ala Thr Ala Leu Ile His Phe Leu
                100                 105                 110

Ser Asp Ala Asn Glu Thr Phe Arg Gly Leu Lys His Lys Glu Tyr Pro
            115                 120                 125

Tyr Ala Phe Met Leu Ala Ala Gly Tyr Cys Leu Thr Met Leu Ala
        130                 135                 140

Asp Val Ala Val Ala Phe Val Ala Gly Ser Asn Asn His Val
145                 150                 155                 160

Gly Ala Ser Val Gly Glu Ser Arg Glu Asp Asp Val Ala Val Lys
                165                 170                 175

Glu Glu Gly Arg Arg Glu Ile Lys Ser Gly Val Asp Val Ser Gln Ala
            180                 185                 190

Leu Ile Arg Thr Ser Gly Phe Gly Asp Thr Ala Leu Leu Ile Phe Ala
                195                 200                 205

Leu Cys Phe His Ser Ile Phe Glu Gly Ile Ala Ile Gly Leu Ser Asp
    210                 215                 220

Thr Lys Ser Asp Ala Trp Arg Asn Leu Trp Thr Ile Ser Leu His Lys
225                 230                 235                 240

Val Phe Ala Ala Val Ala Met Gly Ile Ala Leu Leu Lys Leu Ile Pro
                245                 250                 255

Lys Arg Pro Phe Phe Leu Thr Val Val Tyr Ser Phe Ala Phe Gly Ile
                260                 265                 270

Ser Ser Pro Ile Gly Val Gly Ile Gly Ile Gly Ile Asn Ala Thr Ser
            275                 280                 285

Gln Gly Ala Gly Gly Asp Trp Thr Tyr Ala Ile Ser Met Gly Leu Ala
        290                 295                 300

Cys Gly Val Phe Val Tyr Val Ala Val Asn His Leu Ile Ser Lys Gly
305                 310                 315                 320

Tyr Lys Pro Leu Glu Glu Cys Tyr Phe Asp Lys Pro Ile Tyr Lys Phe
                325                 330                 335

Ile Ala Val Phe Leu Gly Val Ala Leu Leu Ser Val Val Met Ile Trp
                340                 345                 350

Asp

<210> SEQ ID NO 7
<211> LENGTH: 1374
<212> TYPE: DNA
<213> ORGANISM: Arabidopsis thaliana
<220> FEATURE:
<221> NAME/KEY: CDS
<222> LOCATION: (48)..(1064)

<400> SEQUENCE: 7
gtgtgagtaa tttagaaaag ccctaatttt aaaataagat agagatt atg aag act     56
                                                    Met Lys Thr
                                                      1 aag agc gtg aaa ctc tta ttc ttc ttc tcc gtc tcc ctc ctt ctc       104
Lys Ser Val Lys Leu Leu Phe Phe Phe Ser Val Ser Leu Leu Leu
  5                  10                  15 atc gcc gtc gtc aac gcc gcc gaa ggc cat tca cat ggt gga cca aaa   152
Ile Ala Val Val Asn Ala Ala Glu Gly His Ser His Gly Gly Pro Lys
 20                  25                  30                  35 tgt gaa tgc tca cac gaa gac gac cat gaa aac aaa gcc gga gct cgg   200
Cys Glu Cys Ser His Glu Asp Asp His Glu Asn Lys Ala Gly Ala Arg
                 40                  45                  50
```

-continued

| | |
|---|---|
| aaa tac aag atc gcc gca att cct aca gtt cta ata gcc ggc ata atc<br>Lys Tyr Lys Ile Ala Ala Ile Pro Thr Val Leu Ile Ala Gly Ile Ile<br>55                          60                     65 | 248 |
| gga gtt ctt ttc cct ttg tta ggc aaa gtc ttc cct tct ttg cgt cca<br>Gly Val Leu Phe Pro Leu Leu Gly Lys Val Phe Pro Ser Leu Arg Pro<br>70                         75                      80 | 296 |
| gaa aca tgt ttc ttc ttc gtc acg aaa gct ttc gca gcc gga gtt atc<br>Glu Thr Cys Phe Phe Phe Val Thr Lys Ala Phe Ala Ala Gly Val Ile<br>85                         90                     95 | 344 |
| ttg gct acc gga ttt atg cat gtc ttg cct gag gct tac gag atg ctt<br>Leu Ala Thr Gly Phe Met His Val Leu Pro Glu Ala Tyr Glu Met Leu<br>100                     105                110             115 | 392 |
| aac tct cca tgt ttg ata tct gaa gca tgg gaa ttt ccg ttc acc gga<br>Asn Ser Pro Cys Leu Ile Ser Glu Ala Trp Glu Phe Pro Phe Thr Gly<br>120                   125                130 | 440 |
| ttt att gcg atg att gct gcg atc ttg acg tta tcc gtt gat aca ttt<br>Phe Ile Ala Met Ile Ala Ala Ile Leu Thr Leu Ser Val Asp Thr Phe<br>135                   140                145 | 488 |
| gcc act tcg agt ttc tat aaa tcg cat tgc aaa gcg tct aag agg gtc<br>Ala Thr Ser Ser Phe Tyr Lys Ser His Cys Lys Ala Ser Lys Arg Val<br>150                   155                160 | 536 |
| agt gat gga gaa acc ggc gag tcc tcc gtt gac tcc gag aag gtc caa<br>Ser Asp Gly Glu Thr Gly Glu Ser Ser Val Asp Ser Glu Lys Val Gln<br>165                   170                175 | 584 |
| att ctc cgg act aga gtt att gca cag gta ttg gag ttg gga ata ata<br>Ile Leu Arg Thr Arg Val Ile Ala Gln Val Leu Glu Leu Gly Ile Ile<br>180                   185                190             195 | 632 |
| gta cac tca gtg gta ata gga ata tca cta gga gct tca cag agc cca<br>Val His Ser Val Val Ile Gly Ile Ser Leu Gly Ala Ser Gln Ser Pro<br>200                   205                210 | 680 |
| gat gct gca aaa gct ctg ttt att gcc tta atg ttt cat caa tgc ttc<br>Asp Ala Ala Lys Ala Leu Phe Ile Ala Leu Met Phe His Gln Cys Phe<br>215                   220                225 | 728 |
| gaa ggt cta ggc ctt ggt ggt tgt att gct cag gga aaa ttc aag tgt<br>Glu Gly Leu Gly Leu Gly Gly Cys Ile Ala Gln Gly Lys Phe Lys Cys<br>230                   235                240 | 776 |
| ttg tca gta aca atc atg tcg acg ttc ttc gca ata acg aca ccg ata<br>Leu Ser Val Thr Ile Met Ser Thr Phe Phe Ala Ile Thr Thr Pro Ile<br>245                   250                255 | 824 |
| gga atc gtt gtg gga atg gga ata gca aat tct tac gat gag tct tca<br>Gly Ile Val Val Gly Met Gly Ile Ala Asn Ser Tyr Asp Glu Ser Ser<br>260                   265                270             275 | 872 |
| cca acg gct ctg atc gtt caa gga gtt ttg aac gct gca tcc gca ggc<br>Pro Thr Ala Leu Ile Val Gln Gly Val Leu Asn Ala Ala Ser Ala Gly<br>280                   285                290 | 920 |
| att ctc atc tac atg tct ttg gtt gac ctt ctc gca gca gat ttc acg<br>Ile Leu Ile Tyr Met Ser Leu Val Asp Leu Leu Ala Ala Asp Phe Thr<br>295                   300                305 | 968 |
| cac cct aaa atg caa tcc aat act ggg ctt caa att atg gcc cat att<br>His Pro Lys Met Gln Ser Asn Thr Gly Leu Gln Ile Met Ala His Ile<br>310                   315                320 | 1016 |
| gct ctc ctt ctt ggt gct ggc ctc atg tct cta ttg gct aaa tgg gct<br>Ala Leu Leu Leu Gly Ala Gly Leu Met Ser Leu Leu Ala Lys Trp Ala<br>325                   330                335 | 1064 |
| tgatagctcc ttaattcaac tcttctagtt tttgctcatg gcctttatg gccaccttga | 1124 |
| attcgaatta tttgttctta ttttccccct tttcaatgat attttgaga tctctatttt | 1184 |
| ctgaaacact tcatgtactc atgtttaaca ttattacaat tgtgtatatt gatcagtgtc | 1244 |
| caaggaaaaa aaaaaaaaaa aaaaaaaaaa aaaaaaaact aaattactca cactggcggc | 1304 |

```
cgccaccgcg gtggagctcc agcttttgtt cccttttagtg agggttaatt tcgagcttgg    1364
cgtaatcata                                                             1374
```

<210> SEQ ID NO 8
<211> LENGTH: 339
<212> TYPE: PRT
<213> ORGANISM: Arabidopsis thaliana

<400> SEQUENCE: 8

```
Met Lys Thr Lys Ser Val Lys Leu Leu Phe Phe Phe Ser Val Ser
  1               5                  10                  15

Leu Leu Leu Ile Ala Val Val Asn Ala Ala Glu Gly His Ser His Gly
                 20                  25                  30

Gly Pro Lys Cys Glu Cys Ser His Glu Asp His Glu Asn Lys Ala
             35                  40                  45

Gly Ala Arg Lys Tyr Lys Ile Ala Ala Ile Pro Thr Val Leu Ile Ala
         50                  55                  60

Gly Ile Ile Gly Val Leu Phe Pro Leu Gly Lys Val Phe Pro Ser
 65                  70                  75                  80

Leu Arg Pro Glu Thr Cys Phe Phe Val Thr Lys Ala Phe Ala Ala
                 85                  90                  95

Gly Val Ile Leu Ala Thr Gly Phe Met His Val Leu Pro Glu Ala Tyr
                100                 105                 110

Glu Met Leu Asn Ser Pro Cys Leu Ile Ser Glu Ala Trp Glu Phe Pro
                115                 120                 125

Phe Thr Gly Phe Ile Ala Met Ile Ala Ala Ile Leu Thr Leu Ser Val
        130                 135                 140

Asp Thr Phe Ala Thr Ser Ser Phe Tyr Lys Ser His Cys Lys Ala Ser
145                 150                 155                 160

Lys Arg Val Ser Asp Gly Glu Thr Gly Glu Ser Ser Val Asp Ser Glu
                165                 170                 175

Lys Val Gln Ile Leu Arg Thr Arg Val Ile Ala Gln Val Leu Glu Leu
                180                 185                 190

Gly Ile Ile Val His Ser Val Val Gly Ile Ser Leu Gly Ala Ser
        195                 200                 205

Gln Ser Pro Asp Ala Ala Lys Ala Leu Phe Ile Ala Leu Met Phe His
    210                 215                 220

Gln Cys Phe Glu Gly Leu Gly Leu Gly Gly Cys Ile Ala Gln Gly Lys
225                 230                 235                 240

Phe Lys Cys Leu Ser Val Thr Ile Met Ser Thr Phe Phe Ala Ile Thr
                245                 250                 255

Thr Pro Ile Gly Ile Val Val Gly Met Gly Ile Ala Asn Ser Tyr Asp
                260                 265                 270

Glu Ser Ser Pro Thr Ala Leu Ile Val Gln Gly Val Leu Asn Ala Ala
            275                 280                 285

Ser Ala Gly Ile Leu Ile Tyr Met Ser Leu Val Asp Leu Leu Ala Ala
    290                 295                 300

Asp Phe Thr His Pro Lys Met Gln Ser Asn Thr Gly Leu Gln Ile Met
305                 310                 315                 320

Ala His Ile Ala Leu Leu Leu Gly Ala Gly Leu Met Ser Leu Leu Ala
                325                 330                 335

Lys Trp Ala
```

-continued

```
<210> SEQ ID NO 9
<211> LENGTH: 1131
<212> TYPE: DNA
<213> ORGANISM: Arabidopsis thaliana
<220> FEATURE:
<221> NAME/KEY: CDS
<222> LOCATION: (1)..(1128)

<400> SEQUENCE: 9 atg agc aac gtt act acg ccg tgg tgg aaa caa tgg gac cct tct gaa      48
Met Ser Asn Val Thr Thr Pro Trp Trp Lys Gln Trp Asp Pro Ser Glu
 1               5                  10                  15 gtt aca ctt gcc gat aaa acc cct gat gat gtg tgg aag acc tgt gtt      96
Val Thr Leu Ala Asp Lys Thr Pro Asp Asp Val Trp Lys Thr Cys Val
                20                  25                  30 ttg caa ggt gtt tac ttt ggt gga aac gag tac aat ggt aac tta ggt     144
Leu Gln Gly Val Tyr Phe Gly Gly Asn Glu Tyr Asn Gly Asn Leu Gly
         35                  40                  45 gcc aga ata tct tcc gtc ttt gtt att ctt ttc gtg agt act ttt ttc     192
Ala Arg Ile Ser Ser Val Phe Val Ile Leu Phe Val Ser Thr Phe Phe
     50                  55                  60 acc atg ttc cca tta atc tca aca aaa gtg aaa aga ttg aga att cct     240
Thr Met Phe Pro Leu Ile Ser Thr Lys Val Lys Arg Leu Arg Ile Pro
 65                  70                  75                  80 cta tat gtt tac ctt ttc gca aag tat ttt ggt tcc ggt gtt att gtt     288
Leu Tyr Val Tyr Leu Phe Ala Lys Tyr Phe Gly Ser Gly Val Ile Val
                 85                  90                  95 gca acc gca ttt atc cac tta atg gac cct gct tat ggt gcg att ggt     336
Ala Thr Ala Phe Ile His Leu Met Asp Pro Ala Tyr Gly Ala Ile Gly
            100                 105                 110 ggt acc act tgt gta gga caa acc ggt aac tgg ggt ctt tat tca tgg     384
Gly Thr Thr Cys Val Gly Gln Thr Gly Asn Trp Gly Leu Tyr Ser Trp
        115                 120                 125 tgt cct gcc att atg cta acg agt ttg acc ttc act ttc ctt act gat     432
Cys Pro Ala Ile Met Leu Thr Ser Leu Thr Phe Thr Phe Leu Thr Asp
    130                 135                 140 cta ttc agt agc gtc tgg gtt gaa aga aag tat ggt ctt tcc cat gac     480
Leu Phe Ser Ser Val Trp Val Glu Arg Lys Tyr Gly Leu Ser His Asp
145                 150                 155                 160 cat acc cac gat gaa att aaa gac act gtt gtg aga aac act gca gct     528
His Thr His Asp Glu Ile Lys Asp Thr Val Val Arg Asn Thr Ala Ala
                165                 170                 175 gtt tca agt gag aat gac aat gag aat ggt act gca aat gga tct cat     576
Val Ser Ser Glu Asn Asp Asn Glu Asn Gly Thr Ala Asn Gly Ser His
            180                 185                 190 gac acc aag aac gga gta gag tat tat gaa gat tca gac gct aca tcc     624
Asp Thr Lys Asn Gly Val Glu Tyr Tyr Glu Asp Ser Asp Ala Thr Ser
        195                 200                 205 atg gat gtt gtt caa tca ttt caa gca caa ttt tat gcc ttt tta att     672
Met Asp Val Val Gln Ser Phe Gln Ala Gln Phe Tyr Ala Phe Leu Ile
    210                 215                 220 tta gaa ttc ggt gtg att ttc cac tcc gtt atg atc ggt cta aac ctg     720
Leu Glu Phe Gly Val Ile Phe His Ser Val Met Ile Gly Leu Asn Leu
225                 230                 235                 240 gga agt gtt ggt gat gag ttc tcc tcc cta tac cct gtc tta gtg ttc     768
Gly Ser Val Gly Asp Glu Phe Ser Ser Leu Tyr Pro Val Leu Val Phe
                245                 250                 255 cat caa tca ttt gaa ggt tta ggt att ggt gca aga ttg tca gcc att     816
His Gln Ser Phe Glu Gly Leu Gly Ile Gly Ala Arg Leu Ser Ala Ile
            260                 265                 270 gaa ttc cct aga tca aag aga tgg tgg cca tgg gcc cta tgt gtt gcg     864
```

```
Glu Phe Pro Arg Ser Lys Arg Trp Trp Pro Trp Ala Leu Cys Val Ala
            275                 280                 285 tat ggg tta acc aca cca atc tgt gtg gcc atc ggt ttg ggt gtt cgt      912
Tyr Gly Leu Thr Thr Pro Ile Cys Val Ala Ile Gly Leu Gly Val Arg
        290                 295                 300 acc aga tac gtc agc ggt tct tac act gcg ctt gtt atc tct ggt gtt      960
Thr Arg Tyr Val Ser Gly Ser Tyr Thr Ala Leu Val Ile Ser Gly Val
305                 310                 315                 320 ttg gat gcc att tct gct ggt atc tta ttg tac act ggt ttg gtt gaa     1008
Leu Asp Ala Ile Ser Ala Gly Ile Leu Leu Tyr Thr Gly Leu Val Glu
                325                 330                 335 cta cta gca aga gac ttt ata ttc aat cct caa aga aca aag gat cta     1056
Leu Leu Ala Arg Asp Phe Ile Phe Asn Pro Gln Arg Thr Lys Asp Leu
            340                 345                 350 aga gaa ttg tcc ttc aac gtt ata tgc act ctt ttc ggt gct ggt atc     1104
Arg Glu Leu Ser Phe Asn Val Ile Cys Thr Leu Phe Gly Ala Gly Ile
        355                 360                 365 atg gct ttg atc ggt aag tgg gct taa                                 1131
Met Ala Leu Ile Gly Lys Trp Ala
    370                 375

<210> SEQ ID NO 10
<211> LENGTH: 376
<212> TYPE: PRT
<213> ORGANISM: Arabidopsis thaliana

<400> SEQUENCE: 10

Met Ser Asn Val Thr Thr Pro Trp Trp Lys Gln Trp Asp Pro Ser Glu
 1               5                  10                  15

Val Thr Leu Ala Asp Lys Thr Pro Asp Asp Val Trp Lys Thr Cys Val
            20                  25                  30

Leu Gln Gly Val Tyr Phe Gly Gly Asn Glu Tyr Asn Gly Asn Leu Gly
        35                  40                  45

Ala Arg Ile Ser Ser Val Phe Ile Leu Phe Val Ser Thr Phe Phe
    50                  55                  60

Thr Met Phe Pro Leu Ile Ser Thr Lys Val Lys Arg Leu Arg Ile Pro
65                  70                  75                  80

Leu Tyr Val Tyr Leu Phe Ala Lys Tyr Phe Gly Ser Gly Val Ile Val
                85                  90                  95

Ala Thr Ala Phe Ile His Leu Met Asp Pro Ala Tyr Gly Ala Ile Gly
            100                 105                 110

Gly Thr Thr Cys Val Gly Gln Thr Gly Asn Trp Gly Leu Tyr Ser Trp
        115                 120                 125

Cys Pro Ala Ile Met Leu Thr Ser Leu Thr Phe Thr Phe Leu Thr Asp
    130                 135                 140

Leu Phe Ser Ser Val Trp Val Glu Arg Lys Tyr Gly Leu Ser His Asp
145                 150                 155                 160

His Thr His Asp Glu Ile Lys Asp Thr Val Val Arg Asn Thr Ala Ala
                165                 170                 175

Val Ser Ser Glu Asn Asp Asn Glu Asn Gly Thr Ala Asn Gly Ser His
            180                 185                 190

Asp Thr Lys Asn Gly Val Glu Tyr Tyr Glu Asp Ser Asp Ala Thr Ser
        195                 200                 205

Met Asp Val Val Gln Ser Phe Gln Ala Gln Phe Tyr Ala Phe Leu Ile
    210                 215                 220

Leu Glu Phe Gly Val Ile Phe His Ser Val Met Ile Gly Leu Asn Leu
225                 230                 235                 240
```

```
Gly Ser Val Gly Asp Glu Phe Ser Ser Leu Tyr Pro Val Leu Val Phe
            245                 250                 255

His Gln Ser Phe Glu Gly Leu Gly Ile Gly Ala Arg Leu Ser Ala Ile
            260                 265                 270

Glu Phe Pro Arg Ser Lys Arg Trp Trp Pro Trp Ala Leu Cys Val Ala
            275                 280                 285

Tyr Gly Leu Thr Thr Pro Ile Cys Val Ala Ile Gly Leu Gly Val Arg
            290                 295                 300

Thr Arg Tyr Val Ser Gly Ser Tyr Thr Ala Leu Val Ile Ser Gly Val
305                 310                 315                 320

Leu Asp Ala Ile Ser Ala Gly Ile Leu Leu Tyr Thr Gly Leu Val Glu
            325                 330                 335

Leu Leu Ala Arg Asp Phe Ile Phe Asn Pro Gln Arg Thr Lys Asp Leu
            340                 345                 350

Arg Glu Leu Ser Phe Asn Val Ile Cys Thr Leu Phe Gly Ala Gly Ile
            355                 360                 365

Met Ala Leu Ile Gly Lys Trp Ala
            370                 375

<210> SEQ ID NO 11
<211> LENGTH: 1269
<212> TYPE: DNA
<213> ORGANISM: Arabidopsis thaliana
<220> FEATURE:
<221> NAME/KEY: CDS
<222> LOCATION: (1)..(1266)

<400> SEQUENCE: 11 atg gtt gat ctt ata gcg agg gat gac tcc gta gat act tgc caa gct      48
Met Val Asp Leu Ile Ala Arg Asp Asp Ser Val Asp Thr Cys Gln Ala
  1               5                  10                  15 tct aac ggc tac aat ggg cac gca ggt ctt aga att ctg gca gta ttc      96
Ser Asn Gly Tyr Asn Gly His Ala Gly Leu Arg Ile Leu Ala Val Phe
             20                  25                  30 att ata ctg ata tcg tca gga ttg gga gtt tat ttc cca att ttg tca     144
Ile Ile Leu Ile Ser Ser Gly Leu Gly Val Tyr Phe Pro Ile Leu Ser
         35                  40                  45 tca cgg tat tcg ttt ata agg cta cca aat tgg tgc ttt ttc ata gcg     192
Ser Arg Tyr Ser Phe Ile Arg Leu Pro Asn Trp Cys Phe Phe Ile Ala
     50                  55                  60 aag ttc ttc ggt tct ggt gtc att gtt gcc aca gcg ttc gtt cat ctt     240
Lys Phe Phe Gly Ser Gly Val Ile Val Ala Thr Ala Phe Val His Leu
 65                  70                  75                  80 cta cag ccc gca gcc gaa gct ctg gga gat gaa tgt ctt ggt ggc aca     288
Leu Gln Pro Ala Ala Glu Ala Leu Gly Asp Glu Cys Leu Gly Gly Thr
             85                  90                  95 ttt gcc gaa tat cca tgg gct ttt ggg atc tgt tta atg tcg ctt ttc     336
Phe Ala Glu Tyr Pro Trp Ala Phe Gly Ile Cys Leu Met Ser Leu Phe
            100                 105                 110 tta ctt ttc ttc act gaa atc atc acg cat tat ttt gta gcg aaa acg     384
Leu Leu Phe Phe Thr Glu Ile Ile Thr His Tyr Phe Val Ala Lys Thr
        115                 120                 125 ctg gga cac gat cat ggg gac cat ggg gaa gtt acc agt att gat gtt     432
Leu Gly His Asp His Gly Asp His Gly Glu Val Thr Ser Ile Asp Val
    130                 135                 140 gat gct ccc agt tcg gga ttt gtc atc aga aat atg gac tcg gat cct     480
Asp Ala Pro Ser Ser Gly Phe Val Ile Arg Asn Met Asp Ser Asp Pro
145                 150                 155                 160
```

```
gta tct ttc aat aac gaa gct gcc tac tcc atc cat aat gac aaa act     528
Val Ser Phe Asn Asn Glu Ala Ala Tyr Ser Ile His Asn Asp Lys Thr
            165                 170                 175 ccg tac act act aga aat gaa gag att gtc gct act cct ata aag gaa     576
Pro Tyr Thr Thr Arg Asn Glu Glu Ile Val Ala Thr Pro Ile Lys Glu
        180                 185                 190 aaa gaa ccc ggc tca aat gtt act aat tat gat ctg gaa ccg gga aaa     624
Lys Glu Pro Gly Ser Asn Val Thr Asn Tyr Asp Leu Glu Pro Gly Lys
    195                 200                 205 aca gag tca cta gct aat gaa cta gtt cca acc agt tcc cat gcg aca     672
Thr Glu Ser Leu Ala Asn Glu Leu Val Pro Thr Ser Ser His Ala Thr
210                 215                 220 aat ctc gct tct gta cct gga aaa gat cat tat tct cac gaa aat gac     720
Asn Leu Ala Ser Val Pro Gly Lys Asp His Tyr Ser His Glu Asn Asp
225                 230                 235                 240 cat caa gat gtc tcc cag ttg gcc aca cgt atc gag gag gaa gat aaa     768
His Gln Asp Val Ser Gln Leu Ala Thr Arg Ile Glu Glu Glu Asp Lys
            245                 250                 255 gag cag tat ctc aat cag ata cta gct gtt ttt att cta gaa ttt ggc     816
Glu Gln Tyr Leu Asn Gln Ile Leu Ala Val Phe Ile Leu Glu Phe Gly
        260                 265                 270 atc atc ttt cac tct gta ttt gtg ggt ctt tcg cta tct gtc gcg ggt     864
Ile Ile Phe His Ser Val Phe Val Gly Leu Ser Leu Ser Val Ala Gly
    275                 280                 285 gaa gaa ttc gaa acc tta ttt atc gtt tta act ttc cac caa atg ttc     912
Glu Glu Phe Glu Thr Leu Phe Ile Val Leu Thr Phe His Gln Met Phe
290                 295                 300 gaa ggt ttg ggt cta ggc aca aga gtt gcc gaa acg aat tgg cca gaa     960
Glu Gly Leu Gly Leu Gly Thr Arg Val Ala Glu Thr Asn Trp Pro Glu
305                 310                 315                 320 agt aag aag tac atg cct tgg tta atg gga tta gcc ttc act tta acg    1008
Ser Lys Lys Tyr Met Pro Trp Leu Met Gly Leu Ala Phe Thr Leu Thr
            325                 330                 335 tca ccc ata gca gtc gcg gta ggt att ggt gtc aga cac tct tgg ata    1056
Ser Pro Ile Ala Val Ala Val Gly Ile Gly Val Arg His Ser Trp Ile
        340                 345                 350 cct ggc tct aga aga gca tta att gct aat ggt gtt ttt gac tcg ata    1104
Pro Gly Ser Arg Arg Ala Leu Ile Ala Asn Gly Val Phe Asp Ser Ile
    355                 360                 365 tca tca gga att ctt att tat act gga cta gtc gaa tta atg gct cat    1152
Ser Ser Gly Ile Leu Ile Tyr Thr Gly Leu Val Glu Leu Met Ala His
370                 375                 380 gaa ttc tta tac tct aat caa ttc aaa gga cct gat ggc ctc aaa aaa    1200
Glu Phe Leu Tyr Ser Asn Gln Phe Lys Gly Pro Asp Gly Leu Lys Lys
385                 390                 395                 400 atg ctt agt gca tat ctc atc atg tgt tgt gga gct gct tta atg gct    1248
Met Leu Ser Ala Tyr Leu Ile Met Cys Cys Gly Ala Ala Leu Met Ala
            405                 410                 415 ctt cta ggg aaa tgg gca tag                                        1269
Leu Leu Gly Lys Trp Ala
            420
```

<210> SEQ ID NO 12
<211> LENGTH: 422
<212> TYPE: PRT
<213> ORGANISM: Arabidopsis thaliana

<400> SEQUENCE: 12

```
Met Val Asp Leu Ile Ala Arg Asp Asp Ser Val Asp Thr Cys Gln Ala
 1               5                  10                  15
```

-continued

```
Ser Asn Gly Tyr Asn Gly His Ala Gly Leu Arg Ile Leu Ala Val Phe
            20                  25                  30

Ile Ile Leu Ile Ser Ser Gly Leu Gly Val Tyr Phe Pro Ile Leu Ser
        35                  40                  45

Ser Arg Tyr Ser Phe Ile Arg Leu Pro Asn Trp Cys Phe Phe Ile Ala
    50                  55                  60

Lys Phe Phe Gly Ser Gly Val Ile Val Ala Thr Ala Phe Val His Leu
 65                  70                  75                  80

Leu Gln Pro Ala Ala Glu Ala Leu Gly Asp Glu Cys Leu Gly Gly Thr
                85                  90                  95

Phe Ala Glu Tyr Pro Trp Ala Phe Gly Ile Cys Leu Met Ser Leu Phe
            100                 105                 110

Leu Leu Phe Phe Thr Glu Ile Ile Thr His Tyr Phe Val Ala Lys Thr
        115                 120                 125

Leu Gly His Asp His Gly Asp His Gly Glu Val Thr Ser Ile Asp Val
    130                 135                 140

Asp Ala Pro Ser Ser Gly Phe Val Ile Arg Asn Met Asp Ser Asp Pro
145                 150                 155                 160

Val Ser Phe Asn Asn Glu Ala Ala Tyr Ser Ile His Asn Asp Lys Thr
                165                 170                 175

Pro Tyr Thr Thr Arg Asn Glu Glu Ile Val Ala Thr Pro Ile Lys Glu
            180                 185                 190

Lys Glu Pro Gly Ser Asn Val Thr Asn Tyr Asp Leu Glu Pro Gly Lys
        195                 200                 205

Thr Glu Ser Leu Ala Asn Glu Leu Val Pro Thr Ser Ser His Ala Thr
    210                 215                 220

Asn Leu Ala Ser Val Pro Gly Lys Asp His Tyr Ser His Glu Asn Asp
225                 230                 235                 240

His Gln Asp Val Ser Gln Leu Ala Thr Arg Ile Glu Glu Asp Lys
                245                 250                 255

Glu Gln Tyr Leu Asn Gln Ile Leu Ala Val Phe Ile Leu Glu Phe Gly
            260                 265                 270

Ile Ile Phe His Ser Val Phe Val Gly Leu Ser Leu Ser Val Ala Gly
        275                 280                 285

Glu Glu Phe Glu Thr Leu Phe Ile Val Leu Thr Phe His Gln Met Phe
    290                 295                 300

Glu Gly Leu Gly Leu Gly Thr Arg Val Ala Glu Thr Asn Trp Pro Glu
305                 310                 315                 320

Ser Lys Lys Tyr Met Pro Trp Leu Met Gly Leu Ala Phe Thr Leu Thr
                325                 330                 335

Ser Pro Ile Ala Val Ala Val Gly Ile Gly Val Arg His Ser Trp Ile
            340                 345                 350

Pro Gly Ser Arg Arg Ala Leu Ile Ala Asn Gly Val Phe Asp Ser Ile
        355                 360                 365

Ser Ser Gly Ile Leu Ile Tyr Thr Gly Leu Val Glu Leu Met Ala His
    370                 375                 380

Glu Phe Leu Tyr Ser Asn Gln Phe Lys Gly Pro Asp Gly Leu Lys Lys
385                 390                 395                 400

Met Leu Ser Ala Tyr Leu Ile Met Cys Cys Gly Ala Ala Leu Met Ala
                405                 410                 415

Leu Leu Gly Lys Trp Ala
            420
```

-continued

```
<210> SEQ ID NO 13
<211> LENGTH: 1264
<212> TYPE: DNA
<213> ORGANISM: Arabidopsis thaliana
<220> FEATURE:
<221> NAME/KEY: CDS
<222> LOCATION: (3)..(1037)

<400> SEQUENCE: 13 tc gac cca cgc gtc cgc ctc atc cta ttc acc ttc acc gta tct ccg        47
   Asp Pro Arg Val Arg Leu Ile Leu Phe Thr Phe Thr Val Ser Pro
    1               5                  10                  15 gcg atc tca acg gcc ccg gaa cat tgt gat agc ggc ttt gat aac ccg        95
Ala Ile Ser Thr Ala Pro Glu His Cys Asp Ser Gly Phe Asp Asn Pro
             20                  25                  30 tgc atc aac aaa gct aag gct tta cca ctc aaa atc gta gcc att gtt       143
Cys Ile Asn Lys Ala Lys Ala Leu Pro Leu Lys Ile Val Ala Ile Val
 35                  40                  45 gcc ata ctt aca aca agc ttg ata ggc gtg acc tct cct ctt ttc agc       191
Ala Ile Leu Thr Thr Ser Leu Ile Gly Val Thr Ser Pro Leu Phe Ser
         50                  55                  60 cgt tac att tcg ttc ctc cgt ccc gat ggc aat ggt ttc atg atc gtc       239
Arg Tyr Ile Ser Phe Leu Arg Pro Asp Gly Asn Gly Phe Met Ile Val
 65                  70                  75 aaa tgt ttt tct tct gga atc atc ctt gga acc ggt ttc atg cac gtc       287
Lys Cys Phe Ser Ser Gly Ile Ile Leu Gly Thr Gly Phe Met His Val
 80                  85                  90                  95 ttg cct gac tct ttc gag atg ttg tca tcg aaa tgt ctt agt gat aat       335
Leu Pro Asp Ser Phe Glu Met Leu Ser Ser Lys Cys Leu Ser Asp Asn
                100                 105                 110 ccg cgg cat aag ttc cct tct ggg ggt tta gtc gct atg atg tcc ggt       383
Pro Arg His Lys Phe Pro Ser Gly Gly Leu Val Ala Met Met Ser Gly
            115                 120                 125 cta gtc act cta gcc att gac tcc att acc acc agc ctt tat acc ggt       431
Leu Val Thr Leu Ala Ile Asp Ser Ile Thr Thr Ser Leu Tyr Thr Gly
        130                 135                 140 aag aac tca gtc gga cca gtg cct gat gaa gag tat ggc att gat caa       479
Lys Asn Ser Val Gly Pro Val Pro Asp Glu Glu Tyr Gly Ile Asp Gln
    145                 150                 155 gag aaa gcg att cac atg gta ggc cac aat cat agt cac ggt cat ggt       527
Glu Lys Ala Ile His Met Val Gly His Asn His Ser His Gly His Gly
160                 165                 170                 175 gta gtg cta gca act aaa gat gat gga cag ctt ttg cgc tac caa gtc       575
Val Val Leu Ala Thr Lys Asp Asp Gly Gln Leu Leu Arg Tyr Gln Val
                180                 185                 190 att gcc atg gta ttg gag gtt ggg att tta ttt cat tct gtg gtc att       623
Ile Ala Met Val Leu Glu Val Gly Ile Leu Phe His Ser Val Val Ile
            195                 200                 205 gga cta tct cta gga gca act aat gat tca tgt acc att aaa gga ctc       671
Gly Leu Ser Leu Gly Ala Thr Asn Asp Ser Cys Thr Ile Lys Gly Leu
        210                 215                 220 atc ata gct ctt tgc ttc cat cac ttg ttc gaa ggc ata ggt ctt ggt       719
Ile Ile Ala Leu Cys Phe His His Leu Phe Glu Gly Ile Gly Leu Gly
    225                 230                 235 ggc tgc atc ctc cag gca gat ttt aca aat gtg aag aag ttc ttg atg       767
Gly Cys Ile Leu Gln Ala Asp Phe Thr Asn Val Lys Lys Phe Leu Met
240                 245                 250                 255 gca ttc ttt ttc act gga aca aca cct tgt ggt atc ttt ctt gga atc       815
Ala Phe Phe Phe Thr Gly Thr Thr Pro Cys Gly Ile Phe Leu Gly Ile
                260                 265                 270 gca ttg tcg agt atc tat aga gat aac agt cca acc gcg ttg att acg       863
Ala Leu Ser Ser Ile Tyr Arg Asp Asn Ser Pro Thr Ala Leu Ile Thr
```

```
Ala Leu Ser Ser Ile Tyr Arg Asp Asn Ser Pro Thr Ala Leu Ile Thr
            275                 280                 285 att gga ctg tta aat gct tgc tcg gcc gga atg ctc atc tac atg gcc      911
Ile Gly Leu Leu Asn Ala Cys Ser Ala Gly Met Leu Ile Tyr Met Ala
        290                 295                 300 ctc gtc gac ctt cta gct acc gag ttc atg ggg tca atg ctc caa ggt      959
Leu Val Asp Leu Leu Ala Thr Glu Phe Met Gly Ser Met Leu Gln Gly
305                 310                 315 agc atc aaa ctt cag atc aag tgc ttc acg gcg gct ttg ctt ggc tgc     1007
Ser Ile Lys Leu Gln Ile Lys Cys Phe Thr Ala Ala Leu Leu Gly Cys
320                 325                 330                 335 gcc gta atg tcg gtc gtc gcc gtg tgg gct taaacactct ttcaacataa       1057
Ala Val Met Ser Val Val Ala Val Trp Ala
                340                 345 tcaataaatt atttgattta ttaatccagg cgaccaatac tttcgccttt ggaaaattga   1117 gttttttgttt ttaagtttga atcatttatt agtttgtata gtgcatgtaa gcgtttgaaa  1177
gaaatttctt tttatgacat tgtaaattta tttttatgga tgcgatgttt actttcttaa   1237
aaaaaaaaaa aaaaaaaaaa aaaaaaa                                       1264

<210> SEQ ID NO 14
<211> LENGTH: 345
<212> TYPE: PRT
<213> ORGANISM: Arabidopsis thaliana

<400> SEQUENCE: 14

Asp Pro Arg Val Arg Leu Ile Leu Phe Thr Phe Thr Val Ser Pro Ala
  1               5                  10                  15

Ile Ser Thr Ala Pro Glu His Cys Asp Ser Gly Phe Asp Asn Pro Cys
             20                  25                  30

Ile Asn Lys Ala Lys Ala Leu Pro Leu Lys Ile Val Ala Ile Val Ala
         35                  40                  45

Ile Leu Thr Thr Ser Leu Ile Gly Val Thr Ser Pro Leu Phe Ser Arg
     50                  55                  60

Tyr Ile Ser Phe Leu Arg Pro Asp Gly Asn Gly Phe Met Ile Val Lys
 65                  70                  75                  80

Cys Phe Ser Ser Gly Ile Ile Leu Gly Thr Gly Phe Met His Val Leu
                 85                  90                  95

Pro Asp Ser Phe Glu Met Leu Ser Ser Lys Cys Leu Ser Asp Asn Pro
            100                 105                 110

Arg His Lys Phe Pro Ser Gly Gly Leu Val Ala Met Met Ser Gly Leu
        115                 120                 125

Val Thr Leu Ala Ile Asp Ser Ile Thr Thr Ser Leu Tyr Thr Gly Lys
    130                 135                 140

Asn Ser Val Gly Pro Val Pro Asp Glu Glu Tyr Gly Ile Asp Gln Glu
145                 150                 155                 160

Lys Ala Ile His Met Val Gly His Asn His Ser His Gly His Gly Val
                165                 170                 175

Val Leu Ala Thr Lys Asp Asp Gly Gln Leu Leu Arg Tyr Gln Val Ile
            180                 185                 190

Ala Met Val Leu Glu Val Gly Ile Leu Phe His Ser Val Val Ile Gly
        195                 200                 205

Leu Ser Leu Gly Ala Thr Asn Asp Ser Cys Thr Ile Lys Gly Leu Ile
    210                 215                 220

Ile Ala Leu Cys Phe His His Leu Phe Glu Gly Ile Gly Leu Gly Gly
225                 230                 235                 240
```

```
Cys Ile Leu Gln Ala Asp Phe Thr Asn Val Lys Lys Phe Leu Met Ala
            245                 250                 255

Phe Phe Phe Thr Gly Thr Thr Pro Cys Gly Ile Phe Leu Gly Ile Ala
            260                 265                 270

Leu Ser Ser Ile Tyr Arg Asp Asn Ser Pro Thr Ala Leu Ile Thr Ile
            275                 280                 285

Gly Leu Leu Asn Ala Cys Ser Ala Gly Met Leu Ile Tyr Met Ala Leu
            290                 295                 300

Val Asp Leu Leu Ala Thr Glu Phe Met Gly Ser Met Leu Gln Gly Ser
305                 310                 315                 320

Ile Lys Leu Gln Ile Lys Cys Phe Thr Ala Ala Leu Leu Gly Cys Ala
            325                 330                 335

Val Met Ser Val Val Ala Val Trp Ala
            340                 345
```

<210> SEQ ID NO 15
<211> LENGTH: 25
<212> TYPE: DNA
<213> ORGANISM: Arabidopsis thaliana

<400> SEQUENCE: 15
cggatccatg agcaacgtta ctacg                                    25

<210> SEQ ID NO 16
<211> LENGTH: 29
<212> TYPE: DNA
<213> ORGANISM: Arabidopsis thaliana

<400> SEQUENCE: 16
tacgcgtcga cttaagccca cttaccgat                                29

<210> SEQ ID NO 17
<211> LENGTH: 28
<212> TYPE: DNA
<213> ORGANISM: Arabidopsis thaliana

<400> SEQUENCE: 17
ggaattcgaa ggcaagagta tttcagac                                 28

<210> SEQ ID NO 18
<211> LENGTH: 30
<212> TYPE: DNA
<213> ORGANISM: Arabidopsis thaliana

<400> SEQUENCE: 18
cgggatccat aattcctttt ttgatatttg                               30

<210> SEQ ID NO 19
<211> LENGTH: 30
<212> TYPE: DNA
<213> ORGANISM: Arabidopsis thaliana

<400> SEQUENCE: 19
acgcgtcgac atggttgatc ttatagcgag                               30

<210> SEQ ID NO 20
<211> LENGTH: 27
<212> TYPE: DNA
<213> ORGANISM: Arabidopsis thaliana

<400> SEQUENCE: 20

```
cccgagctcc tatgcccatt tccctag                                              27
```

<210> SEQ ID NO 21
<211> LENGTH: 16
<212> TYPE: PRT
<213> ORGANISM: Arabidopsis thaliana

<400> SEQUENCE: 21

```
Pro Ala Asn Asp Val Thr Leu Pro Ile Lys Glu Asp Ser Ser Asn
 1               5                  10                  15
```

<210> SEQ ID NO 22
<211> LENGTH: 120
<212> TYPE: PRT
<213> ORGANISM: Arabidopsis thaliana

<400> SEQUENCE: 22

```
Leu Ile Phe Val Ser Phe Ala Ile Ser Pro Ala Thr Ser Thr Ala Pro
 1               5                  10                  15

Glu Glu Cys Gly Ser Glu Ser Ala Asn Pro Cys Val Asn Lys Ala Lys
                20                  25                  30

Ala Leu Pro Leu Lys Val Ile Ala Ile Phe Val Ile Leu Ile Ala Ser
            35                  40                  45

Met Ile Gly Val Gly Ala Pro Leu Phe Ser Arg Asn Val Ser Phe Leu
        50                  55                  60

Gln Pro Asp Gly Asn Ile Phe Thr Ile Ile Lys Cys Phe Ala Ser Gly
 65                 70                  75                  80

Ile Ile Leu Gly Thr Gly Phe Met His Val Leu Pro Asp Ser Phe Glu
                85                  90                  95

Met Leu Ser Ser Ile Cys Leu Glu Glu Asn Pro Trp His Lys Phe Pro
            100                 105                 110

Phe Ser Gly Phe Leu Ala Met Leu
        115                 120
```

<210> SEQ ID NO 23
<211> LENGTH: 120
<212> TYPE: PRT
<213> ORGANISM: Arabidopsis thaliana

<400> SEQUENCE: 23

```
Leu Ile Leu Phe Thr Phe Thr Val Ser Pro Ala Ile Ser Thr Ala Pro
 1               5                  10                  15

Glu His Cys Asp Ser Gly Phe Asp Asn Pro Cys Ile Asn Lys Ala Lys
                20                  25                  30

Ala Leu Pro Leu Lys Ile Val Ala Ile Val Ala Ile Leu Thr Thr Ser
            35                  40                  45

Leu Ile Gly Val Thr Ser Pro Leu Phe Ser Arg Tyr Ile Ser Phe Leu
        50                  55                  60

Arg Pro Asp Gly Asn Gly Phe Met Ile Val Lys Cys Phe Ser Ser Gly
 65                 70                  75                  80

Ile Ile Leu Gly Thr Gly Phe Met His Val Leu Pro Asp Ser Phe Glu
                85                  90                  95

Met Leu Ser Ser Lys Cys Leu Ser Asp Asn Pro Trp His Lys Phe Pro
            100                 105                 110

Phe Ala Gly Phe Val Ala Met Met
        115                 120
```

```
<210> SEQ ID NO 24
<211> LENGTH: 48
<212> TYPE: PRT
<213> ORGANISM: Arabidopsis thaliana

<400> SEQUENCE: 24

Leu Leu Ile Tyr Met Ala Leu Val Asp Leu Ala Ala Glu Phe Met
 1               5                  10                  15

Gly Pro Lys Leu Gln Gly Ser Ile Lys Met Gln Phe Lys Cys Leu Ile
                20                  25                  30

Ala Ala Leu Leu Gly Cys Gly Gly Met Ser Ile Ile Ala Lys Trp Ala
            35                  40                  45

<210> SEQ ID NO 25
<211> LENGTH: 48
<212> TYPE: PRT
<213> ORGANISM: Arabidopsis thaliana

<400> SEQUENCE: 25

Ile Leu Val Tyr Met Ala Leu Val Asp Leu Ile Ala Ala Asp Phe Leu
 1               5                  10                  15

Ser Thr Lys Met Arg Cys Asn Phe Arg Leu Gln Ile Val Ser Tyr Val
                20                  25                  30

Met Leu Phe Leu Gly Ala Gly Leu Met Ser Ser Leu Ala Ile Trp Ala
            35                  40                  45

<210> SEQ ID NO 26
<211> LENGTH: 85
<212> TYPE: PRT
<213> ORGANISM: Arabidopsis thaliana

<400> SEQUENCE: 26

Glu Leu Gly Ile Ile Val His Ser Val Val Ile Gly Leu Ser Leu Gly
 1               5                  10                  15

Ala Thr Ser Asp Thr Cys Thr Ile Lys Gly Leu Ile Ala Ala Leu Cys
                20                  25                  30

Phe His Gln Met Phe Glu Gly Met Gly Leu Gly Gly Cys Ile Leu Gln
            35                  40                  45

Ala Glu Tyr Thr Asn Met Lys Lys Phe Val Met Ala Phe Phe Ala
         50                  55                  60

Val Thr Thr Pro Phe Gly Ile Ala Leu Gly Ile Ala Leu Ser Thr Val
 65                  70                  75                  80

Tyr Gln Asp Asn Ser
                85

<210> SEQ ID NO 27
<211> LENGTH: 84
<212> TYPE: PRT
<213> ORGANISM: Arabidopsis thaliana

<400> SEQUENCE: 27

Lys Met Gly Ile Val Val His Ser Val Val Ile Gly Leu Gly Met Gly
 1               5                  10                  15

Ala Ser Gln Asn Val Cys Thr Ile Arg Pro Leu Val Ala Ala Leu Cys
                20                  25                  30

Phe His Met Phe Glu Gly Met Gly Leu Gly Gly Cys Ile Leu Gln Ala
            35                  40                  45
```

```
Gly Tyr Gly Gly Arg Thr Arg Ser Ala Leu Val Phe Phe Phe Ser Thr
    50                  55                  60

Thr Thr Pro Phe Gly Ile Ala Leu Gly Leu Ala Leu Thr Arg Val Tyr
65                      70                  75                  80

Ser Asp Thr Ala
```